(12) United States Patent  
Morgan et al.

(10) Patent No.: US 7,700,329 B2
(45) Date of Patent: Apr. 20, 2010

(54) METHODS FOR MAKING SIMVASTATIN AND INTERMEDIATES

(76) Inventors: Brian Morgan, 4849 Riding Ridge Rd., San Diego, CA (US) 92130; Mark Burk, 12634 Intermezzo Way, San Diego, CA (US) 92130; Michael Levin, 7565 Tupelo Cove, San Diego, CA (US) 92126; Zuolin Zhu, 13718 Sorbonne Ct., San Diego, CA (US) 92128; Jennifer Chaplin, 12537 El Camino Real #C, San Diego, CA (US) 92130; Karen Kustedjo, 4955 Directors Pl., San Diego, CA (US) 92121; Zilin Huang, 13750 NE. 12th St., #I-201, Bellevue, WA (US) 98005; William Greenberg, 3709 Ruette de Ville, San Diego, CA (US) 92130

(*) Notice: Subject to any disclaimer, the term of this patent is extended or adjusted under 35 U.S.C. 154(b) by 540 days.

(21) Appl. No.: 10/576,122

(22) PCT Filed: Oct. 20, 2004

(86) PCT No.: PCT/US2004/034913

§ 371 (c)(1),
(2), (4) Date: Aug. 27, 2007

(87) PCT Pub. No.: WO2005/040107

PCT Pub. Date: May 6, 2005

(65) Prior Publication Data

US 2008/0182303 A1    Jul. 31, 2008

Related U.S. Application Data

(60) Provisional application No. 60/542,100, filed on Feb. 4, 2004, provisional application No. 60/513,237, filed on Oct. 21, 2003.

(51) Int. Cl.
*C12P 17/06* (2006.01)
*C12P 17/12* (2006.01)
*C12P 17/18* (2006.01)

(52) U.S. Cl. ........................ 435/125; 435/123; 435/158

(58) Field of Classification Search .................. 435/123, 435/125, 158
See application file for complete search history.

(56) References Cited

U.S. PATENT DOCUMENTS

| 5,159,104 | A | | 10/1992 | Dabora et al. |
| 5,223,415 | A | * | 6/1993 | Conder et al. ................ 435/125 |
| 5,420,024 | A | * | 5/1995 | Carta et al. .................. 435/125 |
| 5,620,876 | A | | 4/1997 | Davis et al. |
| 6,002,021 | A | | 12/1999 | Yang et al. |
| 6,384,238 | B1 | | 5/2002 | Zlicar |

FOREIGN PATENT DOCUMENTS

| EP | 0 486 153 | | 1/1996 |
| EP | 0 625 208 | | 4/1998 |
| EP | 0625208 | * | 4/1998 |
| GB | 2 255 974 | | 11/1992 |

\* cited by examiner

*Primary Examiner*—D. Margaret Seaman
*Assistant Examiner*—Nizal S Chandrakumar
(74) *Attorney, Agent, or Firm*—Verenium Corporation; Jennifer Risser

(57) ABSTRACT

The invention provides synthetic chemical and chemoenzymatic methods of producing simvastatin and various intermediates. In one aspect, enzymes such as hydrolases, e.g., esterases, are used in the methods of the invention.

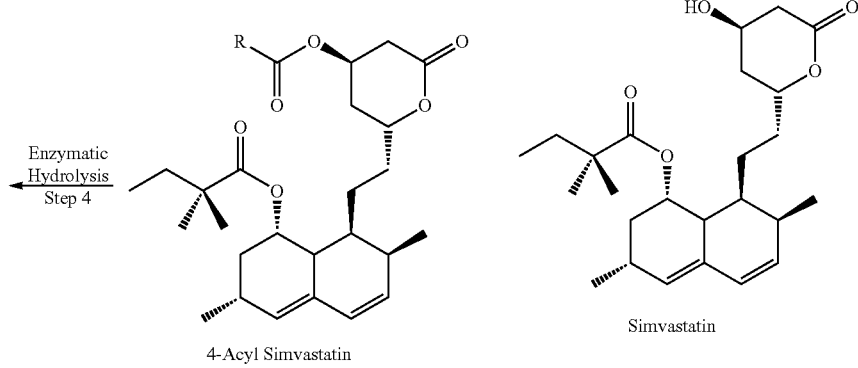
22 Claims, 43 Drawing Sheets

Figure 2

Table 3. Survey of conditions for the acylation of 4-acetyllactone

| Run | BF$_3$·OEt$_2$ mol% | DCM:MeCN | Time h | Mass[1] balance % | 4-Ac Sim % | SM % | DiOAc % | 4-Ac Lova % | Elimin % | 4-Sim-Lova % | BisSim[3] % |
|---|---|---|---|---|---|---|---|---|---|---|---|
| 1 | 8 | 1:1 | 0.5 | 94.8 | 90.8 | 1.2 | 2.8 | 1.1 | 0.5 | 2.7 | 0.9 |
| 2 | 8 (Old) | 1:1 | 5.3 | 85.3 | 90.7 | 0.6 | 3.3 | 1.2 | 0.9 | 2.5 | 0.8 |
| 3 | 8 | 9:1 | 6.5 | 89.7 | 91.1 | 0.6 | 2.7 | 1.1 | 0.8 | 2.7 | 1.0 |
| 4 | 4 | 1:1 | 17.5 | 78.9 | 36.3 | 55.9 | 3.9 | 1.0 | 1.3 | 1.0 | 0.6 |
| 5 | 8 | 5:1 | 1.1 | 92.8 | 96.9 | 0.3 | 0.9 | 0.5 | 0.4 |  | 1.0 |
| 6 | 8 (Stock) | 5:1 | 4.5 | 87.1 | 96.1 | 0.5 | 1.0 | 0.5 | 0.7 |  | 1.2 |

[1]Crude weight yield. [2]Lovastatin with 2,2-dimethylbutyrate at the 4-position. [3]2,2-Dimethylbutyrate at the 4,8-positions.

Figure 3

Table 4. Purification of 4-Acetylsimvastatin by precipitation from MeOH

| | DCE:MeCN | Wt yield % | 4-AcSim % | SM % | DiOA c % | 4-Ac Lova % | Elimi n % | BisSim % |
|---|---|---|---|---|---|---|---|---|
| Crude product | 5:1 | 112[†] | 96.4 | 1.0 | 0.9 | 0.3 | 0.7 | 0.7 |
| After precipitation | | 93 | 98.5 | 0.2 | 0.9 | 0.2 | 0.2 | |

[†] Contaminated with 2,2-dimethylbutyic acid

Figure 4

Table 8. Isolation of Simvastatin

| Run | Scale g | Batch | Theoret Yield g | Isolated Yield g | Yield % | Acid % | Simva % | 4-Acsim % | Elimin % | Lova % |
|---|---|---|---|---|---|---|---|---|---|---|
| 1 | 50 | Pooled: various | 45.4 | 33.8 | 74.4 | 0.2 | 96.7 | 1.7 | 1.2 | 0.2 |
| 2 | 45 | Pooled same batch | 40.9 | 27.7 | 67.7 | 0.3 | 97.8 | 1.3 | 0.3 | 0.4 |
| 3 | 25 | Pooled Same batch | 22.7 | 17.2 | 75.7 | 0.3 | 97.7 | 1.3 | 0.3 | 0.4 |
| 4 | 96.6 | Single batch | 87.8 | 73.4 | 83.6 | 0.7 | 97.5 | 1.0 | 0.6 | 0.2 |

Figure 6
Figure 6A
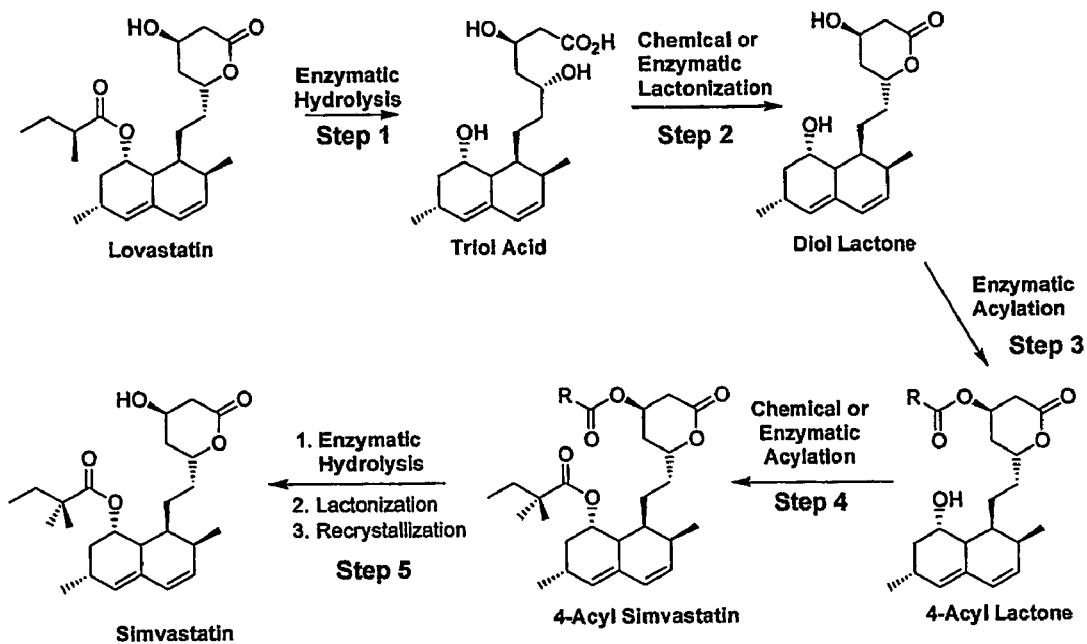
Figure 6B
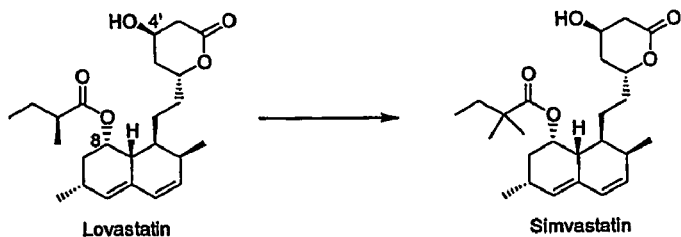

Figure 9
Figure 9A
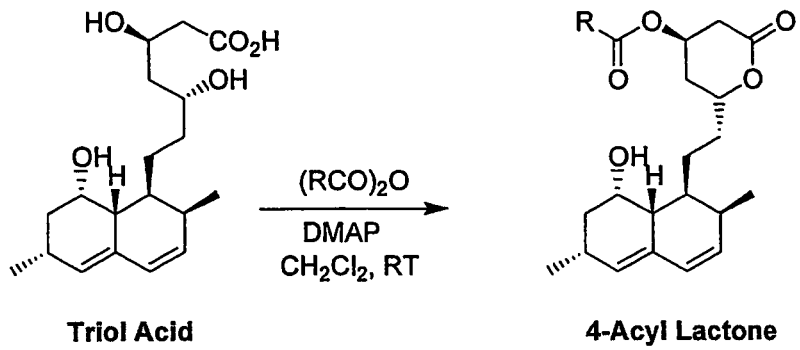
Triol Acid → 4-Acyl Lactone
Figure 9B
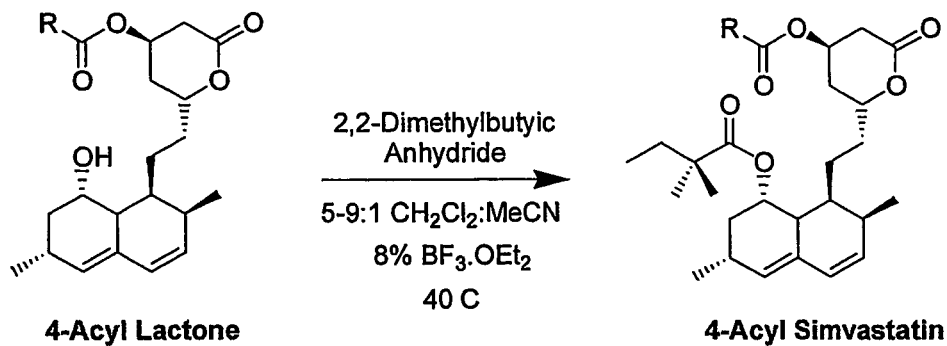
4-Acyl Lactone → 4-Acyl Simvastatin
Figure 9C
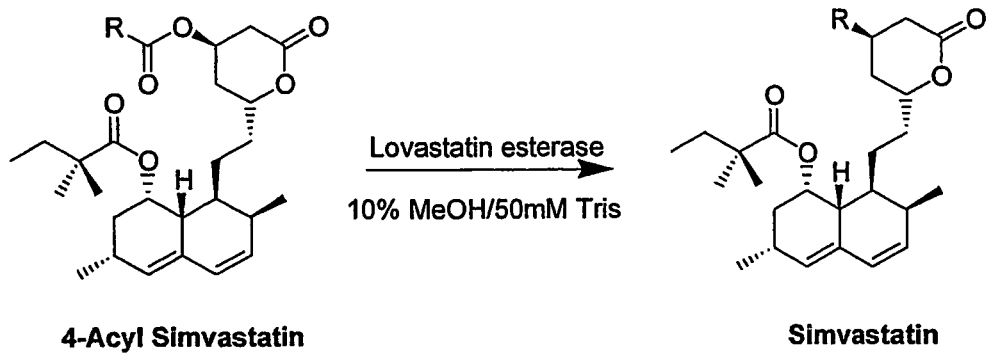
4-Acyl Simvastatin → Simvastatin

4-Acyl Simvastatin     Simvastatin

Figure 14

| Run | Starting Material | Diol lactone (%) | Diacetyl lactone (%) | Elimination or Diacetyl Acid (%) | 4-Acetyl Lactone (%) | Yield % | Mass Balance (%) |
|---|---|---|---|---|---|---|---|
| 1 | Triol acid | 0.5 | 1.7 | 5.1 | 91.1 | 87.4 | 94.2 |
| 2 | Triol acid | 0.5 | 1.7 | 6.4 | 91.0 | 83.2 | 93.0 |
| 3 | Triol acid | 2.3 | 1.3 | 8.1 | 88.3 | 88.8 | 100.9 |
| 4 | Triol acid | 2.4 | 1.3 | 8.1 | 88.2 | 90.9 | 103.1 |

Conditions: DMAP 15 mol%; Anhydride: 3 eq; 0°-RT, $CH_2Cl_2$

4-Acetyl Lactone        Diacetate        Elimination Product

Figure 21

| | Triol Acid | Diol Lactone | 1.66 | Lovastatin | Simvastatin | 2.85 | AcLov | AcSimv | Elimi | HPLC Assay % | CHN |
|---|---|---|---|---|---|---|---|---|---|---|---|
| M-31 | | 0.11 | | 0.34 | 99.5 | | | | | | √ |
| 2645-82/83 | 0.47 | 0.15 | 0.08 | 0.31 | 97.0 | 0.47 | | 0.92 | 0.19 | 84.5 | X |
| 2645-84 | | 0.96 | 0.73 | 0.48 | 95.2 | 0.39 | | 0.93 | 1.35 | 86.3 | √ |
| ML 38 g | | 0.43 | 0.62 | 0.45 | 96.8 | 0.55 | 0.25 | 0.52 | 0.36 | 93.5 | n/d |

Figure 24

| Run no | Block | pH | | Temp °C | | MeOH % | | Tris-HCl mM | | Enzyme mUMB U[1] | | NaCl mM | | Rate[2] | Conversion[3] |
|---|---|---|---|---|---|---|---|---|---|---|---|---|---|---|---|
| | | | | | | | | | | | | | | Responses | |
| | | | | | | | Parameter levels | | | | | | | | |
| 1 | Block 1 | +1 | 9.5 | -1 | 35 | +1 | 20 | -1 | 25 | -1 | 8.4 | +1 | 500 | 3.69 | 45.07 |
| 2 | Block 1 | +1 | 9.5 | +1 | 45 | +1 | 20 | -1 | 25 | +1 | 20 | -1 | 0 | 2.15 | 41.35 |
| 3 | Block 1 | -1 | 8 | -1 | 35 | +1 | 20 | +1 | 200 | +1 | 20 | +1 | 500 | 4.62 | 52.33 |
| 4 | Block 1 | -1 | 8 | +1 | 45 | +1 | 20 | +1 | 200 | -1 | 8.4 | -1 | 0 | 5.43 | 54.22 |
| 5 | Block 1 | +1 | 9.5 | -1 | 35 | -1 | 0 | +1 | 200 | +1 | 20 | -1 | 0 | 14.84 | 94.86 |
| 6 | Block 1 | -1 | 8 | +1 | 45 | -1 | 0 | -1 | 25 | +1 | 20 | +1 | 500 | 13.89 | 65.62 |
| 7 | Block 1 | -1 | 8 | -1 | 35 | -1 | 0 | +1 | 200 | -1 | 8.4 | -1 | 0 | 5.43 | 63.11 |
| 8 | Block 1 | +1 | 9.5 | +1 | 45 | -1 | 0 | -1 | 25 | -1 | 8.4 | +1 | 500 | 13.27 | 54.38 |
| 9 | Block 2 | +1 | 9.5 | -1 | 35 | +1 | 20 | +1 | 200 | +1 | 20 | +1 | 500 | 19.48 | 60.37 |
| 10 | Block 2 | -1 | 8 | +1 | 45 | -1 | 0 | +1 | 200 | -1 | 8.4 | +1 | 500 | 4.90 | 32.87 |
| 11 | Block 2 | -1 | 8 | -1 | 35 | +1 | 20 | -1 | 25 | +1 | 20 | +1 | 500 | 6.86 | 59.52 |
| 12 | Block 2 | -1 | 8 | +1 | 45 | -1 | 0 | -1 | 25 | +1 | 20 | +1 | 500 | 6.46 | 59.84 |
| 13 | Block 2 | -1 | 8 | -1 | 35 | +1 | 20 | +1 | 200 | -1 | 8.4 | -1 | 0 | 20.75 | 96.06 |
| 14 | Block 2 | +1 | 9.5 | +1 | 45 | -1 | 0 | +1 | 200 | +1 | 20 | -1 | 0 | 11.22 | 66.58 |
| 15 | Block 2 | +1 | 9.5 | +1 | 45 | +1 | 20 | -1 | 25 | -1 | 8.4 | +1 | 500 | 12.38 | 61.76 |
| 16 | Block 2 | +1 | 9.5 | -1 | 35 | +1 | 20 | +1 | 200 | -1 | 8.4 | -1 | 0 | 4.66 | 64.27 |

X = C: MeOH
Y = D: Buffer conc
Z = E: Enz conc

Actual Factors
A: pH = 8.00
B: Temp = 35.00
F: NaCl = 0.00

| Parameter | Level | Effect on triol acid production |
|---|---|---|
| MeOH | High | Negative |
| Tris-HCl conc. | High | Positive |
| Enzyme conc. | High | Positive |
| NaCl conc. | High | Negative |
| pH | | No significant effect |
| Temperature | | No significant effect |

Figure 26

| Run no | Block | Parameter levels | | | | | Responses | |
|---|---|---|---|---|---|---|---|---|
| | | Methanol | | Tris-HCl | | Enzyme | | |
| | | | % | | mM | | mUMB U [1] | Rate [2] | Conversion [3] |
| 1 | Block 1 | -1 | 7.50 | -1 | 50 | -1 | 11.1 | 6.58 | 85.00 |
| 2 | Block 1 | +1 | 15.00 | +1 | 200 | -1 | 11.1 | 4.50 | 62.52 |
| 3 | Block 1 | 0 | 11.25 | 0 | 125 | 0 | 15.3 | 7.71 | 88.23 |
| 4 | Block 1 | +1 | 15.00 | -1 | 50 | +1 | 19.5 | 7.55 | 87.55 |
| 5 | Block 1 | -1 | 7.50 | +1 | 200 | +1 | 19.5 | 11.30 | 98.23 |
| 6 | Block 1 | +1 | 11.25 | 0 | 125 | 0 | 15.3 | 7.40 | 88.24 |
| 7 | Block 2 | -1 | 7.50 | -1 | 50 | +1 | 19.5 | 11.88 | 99.60 |
| 8 | Block 2 | +1 | 11.25 | 0 | 125 | 0 | 15.3 | 7.53 | 88.85 |
| 9 | Block 2 | -1 | 7.50 | +1 | 200 | -1 | 11.1 | 6.84 | 84.19 |
| 10 | Block 2 | 0 | 15.00 | +1 | 200 | +1 | 19.5 | 7.73 | 88.84 |
| 11 | Block 2 | 0 | 15.00 | -1 | 50 | -1 | 11.1 | 5.33 | 73.40 |
| 12 | Block 2 | +1 | 11.25 | 0 | 125 | 0 | 15.3 | 8.20 | 93.89 |
| 13 | Block 3 | +1 | 11.25 | 0 | 125 | 0 | 15.3 | 7.18 | 87.79 |
| 14 | Block 3 | +1 | 11.25 | -1.4 | 20 | 0 | 15.3 | 7.30 | 89.24 |
| 15 | Block 3 | +1 | 11.25 | 1.4 | 230 | 0 | 15.3 | 7.73 | 90.75 |
| 16 | Block 3 | +1.4 | 16.50 | 0 | 125 | 0 | 15.3 | 5.64 | 76.20 |
| 17 | Block 3 | +1 | 11.25 | 0 | 125 | 1.4 | 21.18 | 10.43 | 98.03 |
| 18 | Block 3 | +1 | 11.25 | 0 | 125 | 0 | 15.3 | 7.35 | 89.94 |
| 19 | Block 3 | -1.4 | 6.00 | 0 | 125 | 0 | 15.3 | 10.33 | 98.20 |
| 20 | Block 3 | +1 | 11.25 | 0 | 125 | -1.4 | 9.42 | 4.53 | 68.85 |

| Reactions: Scale/mM | Workup | Theoretical Yield g | Product g | Yield % | |
|---|---|---|---|---|---|
| 350 mM pooled | Continuous Liquid/Liquid Dean Stark | 5 | 4.19 | 83.8 | 90% accounted |
| 12 g 500 mM | Centrifugation MeOH | 9.58 | 7.85 Two crops | 81.9 | 91.9% accounted |
| 10.8 g 500 mM | Warm extraction Centrifugation | 8.62 | 6.63 | 76.9 | 85% accounted |
| 50 g 500 mM | Centrifugation | 39.6 | 39.2 evaporated | 99 | 0.6 g in washes |
| 100 g 500 mM | Filtration | 79.2 | 61.6 | 77.8 | 90.8% accounted |

Figure 34
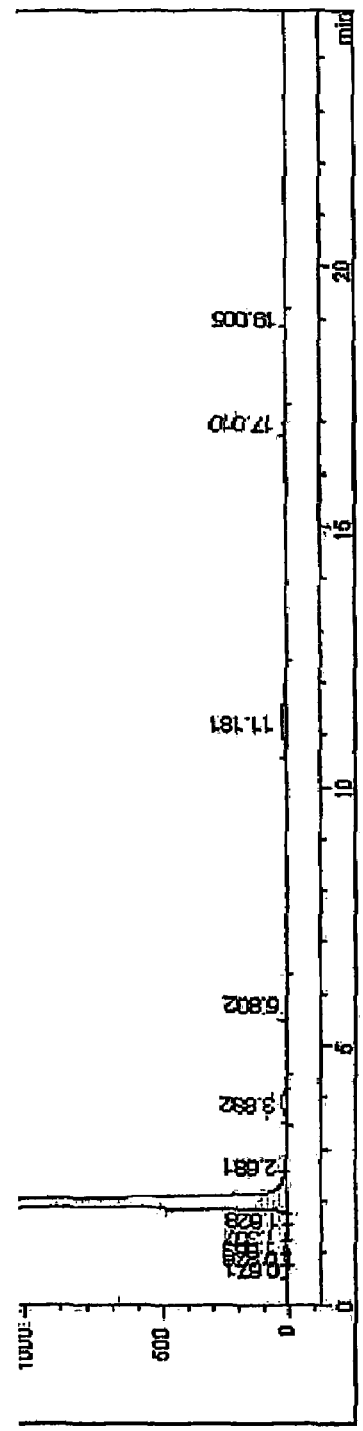
Figure 34A
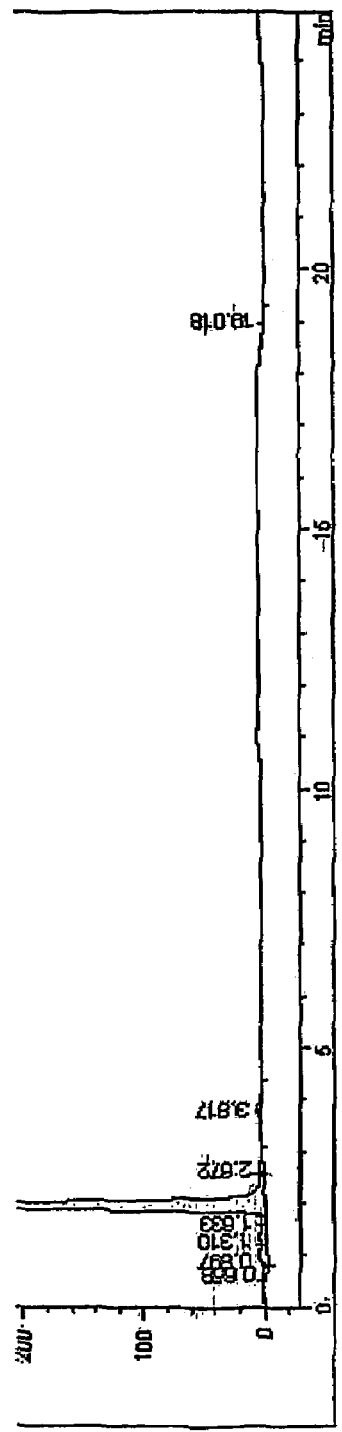
Figure 34B

Figure 35
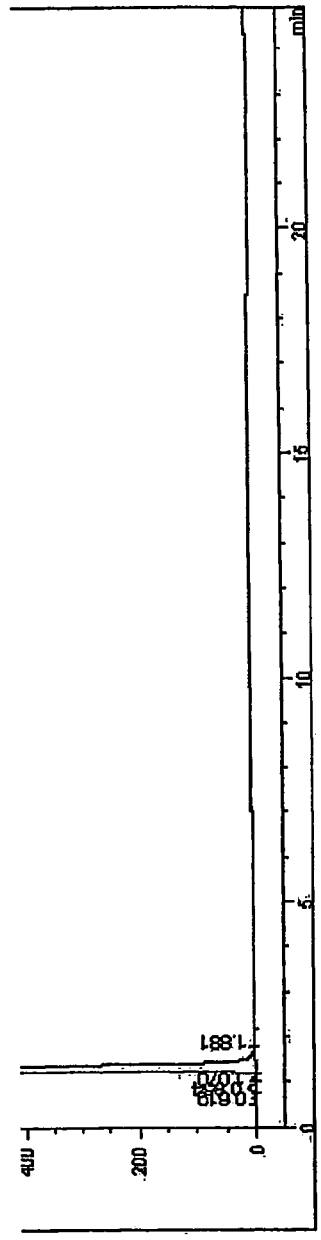
Figure 35A
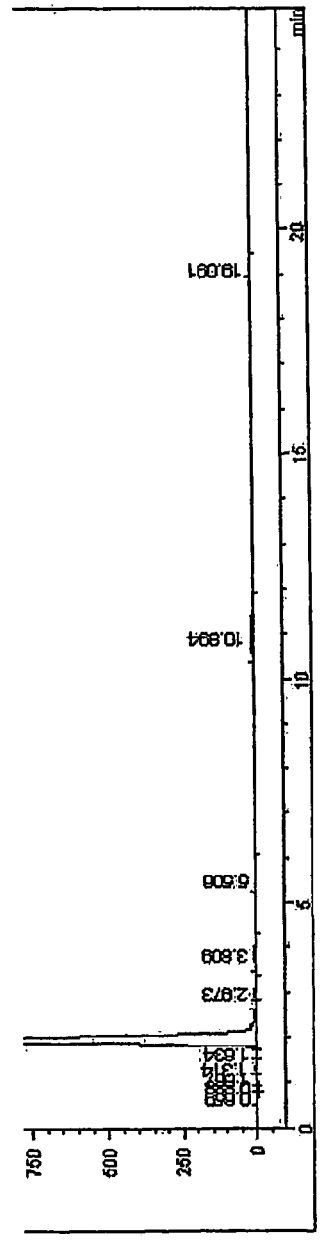
Figure 35B

SEQUENCE LISTING

```
<160> NUMBER OF SEQ ID NOS: 6

<210> SEQ ID NO 1
<211> LENGTH: 1629
<212> TYPE: DNA
<213> ORGANISM: Unknown
<220> FEATURE:
<223> OTHER INFORMATION: Soil sample

<400> SEQUENCE: 1
atgagccttt gcgtcattcg attcatcgcc ggaactttgg tacttgtggc gtcagtggaa      60
tcggcagttg ctcaacaagc gtgtgctgac ctgatgggcc tcgagctgcc gtatacaacg     120
ataacgtccg ctgcagtggc taccgagggc ccaatcccac agccggcgat ctttggaagc     180
actgacccca ttgtggctcc agagcgatgt gaagtgcggg cggtcacgcg ccctacgaag     240
gactccgaga ttcgaatcga gctctggctg ccgctctccg gatggaacgg aaagtatcta     300
caaattggta gcggtggctg ggctggttcg atcaatcgaa cggggctgat aggccctctt     360
```

-continued

```
cagcgcggtt atgccgtagc cgcaaccgac aatggccata tcagcgaagg tttggtgcct    420
gacgcctcct gggctatcgg ccatccgcaa aagctgatcg atttcggtta tcgcgccgtg    480
cacgaaacaa gtgttcaggc caaagctatc ctgcgcgcct actttggccg cggtcaggat    540
ctgagctact tcagcggttg ttctaatggc ggacgcgagg ctctcatgga ggcgcagcgc    600
tatccggaag atttcgaagg catcatcgcc ggagcgcccg cgaacaattg gtcgcgcctg    660
tttacggggt tgtgtggaa tgaacgcgcg ttggcggacg atccaattcc tcctgccaag    720
ttgacagcga ttcaggcggc ggcaattgct gcgtgtgata cgctggacgg tgttgaggac    780
gggctcatcg aaaacccacg agcgtgtagc ttcgatccgc gttcaatggt ctgtacagcc    840
gatgatgcct ctgactgtct gacagaagga caggtcgcga cgctacacag gatatatagc    900
ggcccaacca atcctcggac cggtgagcga atctttccag gctatccgat gggcaccgaa    960
gccgtgccgg cggatgggt accgtggatc gtgtccgcga gctccgaagt tccgagcata   1020
caagcaagct ttggcaactc ctattacggg cacgcggtct tcgagcaatc gaactgggat   1080
ttcaggacgt tggatttcga ccaggacgtt gcgtttggcg atgcgaaggc ggggccggtg   1140
ctcaatgcca cgaaccccga tctgcgttcg tttcgcgcga atggcggcaa actgattcag   1200
tatcatggct ggggcgatgc agccattacg gcttttagtt cgatcgacta ctacgagaac   1260
gtgcgcgcct cctcgatcg cttccccgac ccccgaagcg agaacacgga tatcgacggt   1320
ttctatcgcc tgttcctggt tccgggcatg ggacattgct ccggcgggat cggcccaagt   1380
agctttggca atggcttccg ttccgcacgt acgatgccg agcacgacct actctccgcc   1440
cttgaggcat gggtggagcg agacacggcc ccggagagat tgatcggaac ggggacggcc   1500
gtaggcgacc caaccgcgac tctgacgcgt ccgctatgcc catatccgcg gacgcacgg   1560 tatctcggaa gcggcaactc aaatgatgcg gccaacttcg agtgcgccct gcccgctggc   1620
gtgcagtag                                                          1629
```

<210> SEQ ID NO 2
<211> LENGTH: 542
<212> TYPE: PRT
<213> ORGANISM: Unkown
<220> FEATURE:
<223> OTHER INFORMATION: Soil sample
<220> FEATURE:
<221> NAME/KEY: SIGNAL
<222> LOCATION: (1)...(24)

<400> SEQUENCE: 2

```
Met Ser Leu Cys Val Ile Arg Phe Ile Ala Gly Thr Leu Val Leu Val
1               5                   10                  15

Ala Ser Val Glu Ser Ala Val Ala Gln Gln Ala Cys Ala Asp Leu Met
                20                  25                  30

Gly Leu Glu Leu Pro Tyr Thr Thr Ile Thr Ser Ala Ala Val Ala Thr
            35                  40                  45

Glu Gly Pro Ile Pro Gln Pro Ala Ile Phe Gly Ser Thr Asp Pro Ile
        50                  55                  60

Val Ala Pro Glu Arg Cys Glu Val Arg Ala Val Thr Arg Pro Thr Lys
65                  70                  75                  80

Asp Ser Glu Ile Arg Ile Glu Leu Trp Leu Pro Leu Ser Gly Trp Asn
                85                  90                  95

Gly Lys Tyr Leu Gln Ile Gly Ser Gly Gly Trp Ala Gly Ser Ile Asn
                100                 105                 110
```

```
Arg Thr Gly Leu Ile Gly Pro Leu Gln Arg Gly Tyr Ala Val Ala Ala
        115                 120                 125

Thr Asp Asn Gly His Ile Ser Glu Gly Leu Val Pro Asp Ala Ser Trp
    130                 135                 140

Ala Ile Gly His Pro Gln Lys Leu Ile Asp Phe Gly Tyr Arg Ala Val
145                 150                 155                 160

His Glu Thr Ser Val Gln Ala Lys Ala Ile Leu Arg Ala Tyr Phe Gly
                165                 170                 175

Arg Gly Gln Asp Leu Ser Tyr Phe Ser Gly Cys Ser Asn Gly Gly Arg
            180                 185                 190

Glu Ala Leu Met Glu Ala Gln Arg Tyr Pro Glu Asp Phe Glu Gly Ile
        195                 200                 205

Ile Ala Gly Ala Pro Ala Asn Asn Trp Ser Arg Leu Phe Thr Gly Phe
210                 215                 220

Val Trp Asn Glu Arg Ala Leu Ala Asp Asp Pro Ile Pro Pro Ala Lys
225                 230                 235                 240

Leu Thr Ala Ile Gln Ala Ala Ile Ala Ala Cys Asp Thr Leu Asp
                245                 250                 255

Gly Val Glu Asp Gly Leu Ile Glu Asn Pro Arg Ala Cys Ser Phe Asp
            260                 265                 270

Pro Arg Ser Met Val Cys Thr Ala Asp Ala Ser Asp Cys Leu Thr
        275                 280                 285

Glu Gly Gln Val Ala Thr Leu His Arg Ile Tyr Ser Gly Pro Thr Asn
290                 295                 300

Pro Arg Thr Gly Glu Arg Ile Phe Pro Gly Tyr Pro Met Gly Thr Glu
305                 310                 315                 320

Ala Val Pro Gly Gly Trp Val Pro Trp Ile Val Ser Ala Ser Ser Glu
                325                 330                 335

Val Pro Ser Ile Gln Ala Ser Phe Gly Asn Ser Tyr Tyr Gly His Ala
            340                 345                 350

Val Phe Glu Gln Ser Asn Trp Asp Phe Arg Thr Leu Asp Phe Asp Gln
        355                 360                 365

Asp Val Ala Phe Gly Asp Ala Lys Ala Gly Pro Val Leu Asn Ala Thr
370                 375                 380

Asn Pro Asp Leu Arg Ser Phe Arg Ala Asn Gly Gly Lys Leu Ile Gln
385                 390                 395                 400

Tyr His Gly Trp Gly Asp Ala Ala Ile Thr Ala Phe Ser Ser Ile Asp
                405                 410                 415

Tyr Tyr Glu Asn Val Arg Ala Phe Leu Asp Arg Phe Pro Asp Pro Arg
            420                 425                 430

Ser Glu Asn Thr Asp Ile Asp Gly Phe Tyr Arg Leu Phe Leu Val Pro
        435                 440                 445

Gly Met Gly His Cys Ser Gly Gly Ile Gly Pro Ser Ser Phe Gly Asn
450                 455                 460

Gly Phe Arg Ser Ala Arg Thr Asp Ala Glu His Asp Leu Leu Ser Ala
465                 470                 475                 480

Leu Glu Ala Trp Val Glu Arg Asp Thr Ala Pro Glu Arg Leu Ile Gly
                485                 490                 495

Thr Gly Thr Ala Val Gly Asp Pro Thr Ala Thr Leu Arg Pro Leu
            500                 505                 510
```

-continued

```
Cys Pro Tyr Pro Arg Thr Ala Arg Tyr Leu Gly Ser Gly Asn Ser Asn
        515                 520                 525

Asp Ala Ala Asn Phe Glu Cys Ala Leu Pro Ala Gly Val Gln
    530                 535                 540
```

<210> SEQ ID NO 3
<211> LENGTH: 1209
<212> TYPE: DNA
<213> ORGANISM: Unknown
<220> FEATURE:
<223> OTHER INFORMATION: Soil sample

<400> SEQUENCE: 3

```
atggaaatcc atggtacatg cgacccaaag tttcacttgg tgcggcagga gtttgaacga    60
aatttgcgtg agcgcggcga agtaggagcg tccgtttgcg tcacgttgca cggcgaaacc   120
gtagtggact tgtggggcgg catggcgcgt gccgacactc agacgccatg acggcggag    180
acggtcagta ttgttttttc ctccaccaaa ggcgcaacgg cactctgcgc ccatatgctg   240
gcgtcacgcg gccaactgga tcttgatgca ccagtcgcca cctactggcc ggaatttgcc   300
caagccggca agctcgcat cccggtgaaa atgctcttga accatcaagc tggtctccct    360
gccgtacgga caccgctgcc ccagggtgcc tacgctgact gggaactgat ggtcaatacg   420
ttggccaagg aagagccgtt tgggaacct ggcacccgca acggctatca tgcgctcacc     480
atgggtggc tggtgggaga agtggtgcga cgtgtctctg gtaagtcgct tgggacattc    540
ttccaagagg agatcgccag gccgttgggg ttagatttct ggattggctt accagcagag   600
caagaggcac gggtcgcgcc gatgatcgcg gcggagcctg atccgcaaag cctcttcttc   660
caagaggtcg cgaagcctgg ggccttacag tcgctcgtac tccttaactc cggcggctat   720
atgggtgctc agcctgagta tgactcgcgg gcggcgcatg cggccgagat tggtgcagcc   780
ggtggtatca ccaacgcacg cggcctggca ggcatgtacg caccactggc ctgcggaggc   840
aaactcaaag gggtggagtt ggtcagtcct gacatgctgg cccgaatgtc cagagtggcc   900
tctgcgactg ggagagatgc cgtgctcatg atgccaaccc ggtttgccct gggcttcatg   960
aagtccatgg acaaccgccg ggagcctgct ggcgtgcagg acagcgcgct ctttggggag  1020
gaggcttttg ccatgtgggg ggccgggggt tcgtttggtt ttgccgatcc caaagcagga  1080
atgtcctttg ctataccat gaaccgaatg gggctgggag ccgggctcaa cccgcgggg    1140
caaagcctgg tggatgcaac ctaccgctcg ttagggtatc agtcggatgc ctctggagcc  1200
tggacctga                                                          1209
```

<210> SEQ ID NO 4
<211> LENGTH: 402
<212> TYPE: PRT
<213> ORGANISM: Unknown
<220> FEATURE:
<223> OTHER INFORMATION: Soil sample
<220> FEATURE:
<221> NAME/KEY: DOMAIN
<222> LOCATION: (18)...(386)
<223> OTHER INFORMATION: Beta-lactamase

<400> SEQUENCE: 4

```
Met Glu Ile His Gly Thr Cys Asp Pro Lys Phe His Leu Val Arg Gln
1               5                  10                  15

Glu Phe Glu Arg Asn Leu Arg Glu Arg Gly Glu Val Gly Ala Ser Val
            20                  25                  30
```

Cys Val Thr Leu His Gly Glu Thr Val Val Asp Leu Trp Gly Gly Met
     35                  40                  45

Ala Arg Ala Asp Thr Gln Thr Pro Trp Thr Ala Glu Thr Val Ser Ile
 50                  55                  60

Val Phe Ser Ser Thr Lys Gly Ala Thr Ala Leu Cys Ala His Met Leu
 65                  70                  75                  80

Ala Ser Arg Gly Gln Leu Asp Leu Asp Ala Pro Val Ala Thr Tyr Trp
                 85                  90                  95

Pro Glu Phe Ala Gln Ala Gly Lys Ala Arg Ile Pro Val Lys Met Leu
            100                 105                 110

Leu Asn His Gln Ala Gly Leu Pro Ala Val Arg Thr Pro Leu Pro Gln
        115                 120                 125

Gly Ala Tyr Ala Asp Trp Glu Leu Met Val Asn Thr Leu Ala Lys Glu
    130                 135                 140

Glu Pro Phe Trp Glu Pro Gly Thr Arg Asn Gly Tyr His Ala Leu Thr
145                 150                 155                 160

Met Gly Trp Leu Val Gly Val Val Arg Val Ser Gly Lys Ser
                165                 170                 175

Leu Gly Thr Phe Phe Gln Glu Glu Ile Ala Arg Pro Leu Gly Leu Asp
                180                 185                 190

Phe Trp Ile Gly Leu Pro Ala Glu Gln Glu Ala Arg Val Ala Pro Met
        195                 200                 205

Ile Ala Ala Glu Pro Asp Pro Gln Ser Leu Phe Phe Gln Glu Val Ala
    210                 215                 220

Lys Pro Gly Ala Leu Gln Ser Leu Val Leu Leu Asn Ser Gly Gly Tyr
225                 230                 235                 240

Met Gly Ala Gln Pro Glu Tyr Asp Ser Arg Ala Ala His Ala Ala Glu
                245                 250                 255

Ile Gly Ala Ala Gly Gly Ile Thr Asn Ala Arg Gly Leu Ala Gly Met
                260                 265                 270

Tyr Ala Pro Leu Ala Cys Gly Gly Lys Leu Lys Gly Val Glu Leu Val
        275                 280                 285

Ser Pro Asp Met Leu Ala Arg Met Ser Arg Val Ala Ser Ala Thr Gly
    290                 295                 300

Arg Asp Ala Val Leu Met Met Pro Thr Arg Phe Ala Leu Gly Phe Met
305                 310                 315                 320

Lys Ser Met Asp Asn Arg Arg Glu Pro Ala Gly Val Gln Asp Ser Ala
                325                 330                 335

Leu Phe Gly Glu Glu Ala Phe Gly His Val Gly Ala Gly Ser Phe
                340                 345                 350

Gly Phe Ala Asp Pro Lys Ala Gly Met Ser Phe Gly Tyr Thr Met Asn
        355                 360                 365

Arg Met Gly Leu Gly Ala Gly Leu Asn Pro Arg Gly Gln Ser Leu Val
370                 375                 380

Asp Ala Thr Tyr Arg Ser Leu Gly Tyr Gln Ser Asp Ala Ser Gly Ala
385                 390                 395                 400

Trp Thr

<210> SEQ ID NO 5
<211> LENGTH: 1578
<212> TYPE: DNA
<213> ORGANISM: Unknown
<220> FEATURE:
<223> OTHER INFORMATION: Soil sample -continued

```
<400> SEQUENCE: 5
atgagatcag cagctcgcat cagcgtggcg gcagttgcct ttctttgcct gctcttgacg      60
actcgggttt ccgcccagat cgtgccggcg atggaatgtg cggatctggc gaatcagcag     120
cttcccaaca cgacgatcac ctcggcccag accgtcacca ccgatcgtt aacgccccg       180
ggctcgacga atccgatcac cgacctgcct cctttctgcc gtgtcacagg cgccatcgcc     240
ccgacgagcg agtcgcacat cctcttcgag gtctggctgc cgctggataa atggaacggc     300
aagttcgccg gcgtgggcaa cggcggctgg gccggcatca tctccttcgg cgccctcgga     360
agccagctca agcgcggcta cgcgaccgcc tccacgaata cgggtcacga agcggcgccg     420
gggatgaacg cagccaggtt tgcgttcgag aagccggagc agcttatcga cttcgcctat     480
cgctcccagc acgagacggc cctgaaagcg aaggcgctgg ttcaggcttt ctacgggaag     540
ccgccggaac actcctattt catcgggtgc tcatcgggtg gtaccaggg cctgatggag      600
gcccaacgat ttccggccga ctacgacggg atcgtcgccg gtatgccggc gaacaactgg     660
acacggctga tggccggcga cttggacgcg atccttgccg tctccgtaga tcctgccagc     720
caccttcccg tctccgcatt gggtctgttg tatcgctcgg tgctcgctgc ctgcgacggc     780
atcgacggtg ttgtagacgg tgttctggag gatccgcgcc gatgccggtt cgacccggcc     840
gtgttgatgt gcaaggcgga tcagaatccc gatggctgcc ttacgccggc tcaggtggaa     900
gcggcacggc gcatatacgg cggtctgaag gatcccaaga ccggcgctca gctctatccg     960
gggctggcgc cgggaagcga gccgttctgg ccgcaccgca atccggcgaa tccgttccct    1020
attccgatcg cgcactacaa gtggctcgtc tttgccgatc aaactggga ttggagaaca     1080
ttcaagttca cggatccggc ggactaccag gctttcctca atgcggaagc cacgtatgcc    1140
cctactctca atgcgaccaa tccggacctc cgggagttca gccggcgcgg cggcaggttg    1200
attcagtacc atggctggaa cgatcagctg attgccccgc aaaacagcat cgactattac    1260
gagagcgtcc tttcgttctt cgggtccggc aaacaggatc gagcgcagac cgtgcgcgag    1320
gttcagagct tctaccggct gttcatggcg ccgggtatgg ctcactgtgg aggcggtaca    1380
ggtccgaact catttgacat gctggatgcc ctcgagaagt gggtggaagg cgggatagcg    1440
ccggaacgag tccttgcgac gcgttccata aacggcgtag tcgaccggct gcgcccgctc    1500
tgtccatatc cgcaggtcgc cgtgtacaag ggtcatgggg atacaaacga cgccgcgaac    1560
ttcgtctgtc gcgattag                                                  1578
```

<210> SEQ ID NO 6
<211> LENGTH: 525
<212> TYPE: PRT
<213> ORGANISM: Unkown
<220> FEATURE:
<223> OTHER INFORMATION: Soil sample
<220> FEATURE:
<221> NAME/KEY: SIGNAL
<222> LOCATION: (1)...(25)

<400> SEQUENCE: 6

Met Arg Ser Ala Ala Arg Ile Ser Val Ala Ala Val Ala Phe Leu Cys
1               5                   10                  15

Leu Leu Leu Thr Thr Arg Val Ser Ala Gln Ile Val Pro Ala Met Glu
            20                  25                  30

Cys Ala Asp Leu Ala Asn Gln Gln Leu Pro Asn Thr Thr Ile Thr Ser
        35                  40                  45

-continued

```
Ala Gln Thr Val Thr Thr Gly Ser Leu Thr Pro Pro Gly Ser Thr Asn
 50                  55                  60

Pro Ile Thr Asp Leu Pro Pro Phe Cys Arg Val Thr Gly Ala Ile Ala
 65                  70                  75                  80

Pro Thr Ser Glu Ser His Ile Leu Phe Glu Val Trp Leu Pro Leu Asp
                 85                  90                  95

Lys Trp Asn Gly Lys Phe Ala Gly Val Gly Asn Gly Gly Trp Ala Gly
            100                 105                 110

Ile Ile Ser Phe Gly Ala Leu Gly Ser Gln Leu Lys Arg Gly Tyr Ala
            115                 120                 125

Thr Ala Ser Thr Asn Thr Gly His Glu Ala Ala Pro Gly Met Asn Ala
130                 135                 140

Ala Arg Phe Ala Phe Glu Lys Pro Glu Gln Leu Ile Asp Phe Ala Tyr
145                 150                 155                 160

Arg Ser Gln His Glu Thr Ala Leu Lys Ala Lys Ala Leu Val Gln Ala
                165                 170                 175

Phe Tyr Gly Lys Pro Glu His Ser Tyr Phe Ile Gly Cys Ser Ser
            180                 185                 190

Gly Gly Tyr Gln Gly Leu Met Glu Ala Gln Arg Phe Pro Ala Asp Tyr
            195                 200                 205

Asp Gly Ile Val Ala Gly Met Pro Ala Asn Asn Trp Thr Arg Leu Met
210                 215                 220

Ala Gly Asp Leu Asp Ala Ile Leu Ala Val Ser Val Asp Pro Ala Ser
225                 230                 235                 240

His Leu Pro Val Ser Ala Leu Gly Leu Leu Tyr Arg Ser Val Leu Ala
                245                 250                 255

Ala Cys Asp Gly Ile Asp Gly Val Val Asp Gly Val Leu Glu Asp Pro
            260                 265                 270

Arg Arg Cys Arg Phe Asp Pro Ala Val Leu Met Cys Lys Ala Asp Gln
            275                 280                 285

Asn Pro Asp Gly Cys Leu Thr Pro Ala Gln Val Glu Ala Ala Arg Arg
290                 295                 300

Ile Tyr Gly Gly Leu Lys Asp Pro Lys Thr Gly Ala Gln Leu Tyr Pro
305                 310                 315                 320

Gly Leu Ala Pro Gly Ser Glu Pro Phe Trp Pro His Arg Asn Pro Ala
                325                 330                 335

Asn Pro Phe Pro Ile Pro Ile Ala His Tyr Lys Trp Leu Val Phe Ala
            340                 345                 350

Asp Pro Asn Trp Asp Trp Arg Thr Phe Lys Phe Thr Asp Pro Ala Asp
            355                 360                 365

Tyr Gln Ala Phe Leu Asn Ala Glu Ala Thr Tyr Ala Pro Thr Leu Asn
370                 375                 380

Ala Thr Asn Pro Asp Leu Arg Glu Phe Ser Arg Arg Gly Gly Arg Leu
385                 390                 395                 400

Ile Gln Tyr His Gly Trp Asn Asp Gln Leu Ile Ala Pro Gln Asn Ser
                405                 410                 415

Ile Asp Tyr Tyr Glu Ser Val Leu Ser Phe Gly Ser Gly Lys Gln
            420                 425                 430

Asp Arg Ala Gln Thr Val Arg Glu Val Gln Ser Phe Tyr Arg Leu Phe
            435                 440                 445

Met Ala Pro Gly Met Ala His Cys Gly Gly Thr Gly Pro Asn Ser
450                 455                 460
```

-continued

```
Phe Asp Met Leu Asp Ala Leu Glu Lys Trp Val Glu Gly Gly Ile Ala
465                 470                 475                 480

Pro Glu Arg Val Leu Ala Thr Arg Ser Ile Asn Gly Val Val Asp Arg
                485                 490                 495

Leu Arg Pro Leu Cys Pro Tyr Pro Gln Val Ala Val Tyr Lys Gly His
            500             505                 510

Gly Asp Thr Asn Asp Ala Ala Asn Phe Val Cys Arg Asp
        515             520                 525
```

US 7,700,329 B2

METHODS FOR MAKING SIMVASTATIN AND INTERMEDIATES

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 564462012800seqlist.txt | Nov. 7, 2007 | 19,343 bytes |

TECHNICAL FIELD

This invention generally relates to the field of synthetic organic and medicinal chemistry. In one aspect, the invention provides synthetic chemical and chemoenzymatic methods of producing simvastatin and various intermediates and related compounds. In one aspect, enzymes such as hydrolases, e.g., esterases, are used in the methods of the invention.

BACKGROUND

Simvastatin is a potent antihypercholesterolemic agent. It is marketed under the name ZOCOR® (Merck). Simvastatin, Mevastatin, Lovastatin and Pravastatin are hexahydronaphthalene derivatives used as inhibitors of the enzyme HMG-CoA reductase, the rate-controlling enzyme in the biosynthetic pathway for formation of cholesterol in the human body. After oral ingestion, simvastatin, which is an inactive lactone, is hydrolyzed to the corresponding β-hydroxyacid form. This is an inhibitor of 3-hydroxy-3-methylglutaryl-coenzyme A (HMG-CoA) reductase. This enzyme catalyzes the conversion of HMG-CoA to mevalonate, which is an early and rate-limiting step in the biosynthesis of cholesterol.

Mevastatin, Lovastatin and Pravastatin are natural fermentation products which possess a 2-methylbutyrate side chain at C-8 of their hexahydronaphthalene ring system. Simvastatin can be derived synthetically from a fermentation product of *Aspergillus terreus*.

Compounds possessing a C-8 2,2-dimethylbutyrate side chain, including Simvastatin, can be better inhibitors of HMG-CoA reductase than their 2-methylbutyrate counterparts. Thus 2,2-dimethylbutyrate derivatives may have greater promise for the treatment of atherosclerosis, hyperlipemia, familial hypercholesterolemia and similar disorders. However, these derivatives, including Simvastatin, are not naturally occurring and have to be produced synthetically. As a result, the introduction on the market of the more potent HMG-CoA reductase inhibitor Simvastatin has prompted the need for efficient, high yielding processes for manufacturing it.

SUMMARY

In one aspect, the invention provides a novel process comprising (i) the use of an enzyme of the invention (e.g., exemplary enzyme having a sequence as set forth in SEQ ID NO:4, encoded by SEQ ID NO:3) to remove the lovastatin side-chain under mild conditions, (ii) the use of the same enzyme to selectively remove an ester protecting group in the final step, and (iii) the application of novel conditions for the introduction of the simvastatin side-chain.

The invention provides a novel four-step method for preparing simvastatin comprising following steps: (a) enzymatic hydrolysis (e.g., using a polypeptide having esterase activity) of lovastatin, lovastatin acid or a salt of lovastatin acid to form a triol acid or a salt of a triol acid; (b) forming in one step a 4-acyl lactone by chemical and/or enzymatic lactonization and acylation (including acylating the 4-position (4'-OH) on the lactone ring, where the ring is acylated with an R— group as described, below); (c) acylating the 8-position (8'-OH) of the 4-acetyl lactone by chemical and/or enzymatic acylation to form a 4-acyl simvastatin; and (d) removing selectively the acyl group at the 4' position by chemical and/or enzymatic hydrolysis (e.g., using a polypeptide having esterase activity), thereby making simvastatin.

In one aspect, a four-step method for preparing simvastatin of the invention comprises a scheme as set forth in FIG. 5. Thus, in one aspect the invention provides a chemoenzymatic transformation of lovastatin to simvastatin carried out in four steps, as outlined in FIG. 5.

In alternative aspects, the four-step method for preparing simvastatin of the invention (e.g., the process outlined in FIG. 5) gives an overall yield of lovastatin to simvastatin of at least 50%, 55%, 60%, 65%, 70%, 75%, 80%, 85% or 90% or more. Exemplary protocols, and studies identifying where yield loss is occurring and where process improvements could be effected, are discussed, e.g., in Examples 5, 6, 7 and 8, below.

In one aspect, the invention provides a four-step route to synthesize simvastatin from lovastatin, as illustrated in FIG. 5, wherein the synthesis scheme comprises the following steps:

Step 1: Enzymatic hydrolysis of lovastatin, lovastatin acid and/or a salt of lovastatin acid to form the triol acid using an enzyme capable of catalyzing the hydrolysis of lovastatin acid, e.g., a hydrolase as described herein or a commercially available hydrolase. For example, exemplary hydrolase enzymes that can be used in the enzymatic hydrolysis of the (S)-2-methylbutyrate sidechain are the esterase enzymes: SEQ ID NO:4 (encoded by, e.g., SEQ ID NO:3), SEQ ID NO:6 (encoded by, e.g., SEQ ID NO:5), and SEQ ID NO:2 (encoded by, e.g., SEQ ID NO:1). SEQ ID NO:4 (encoded by, e.g., SEQ ID NO:3).

Step 2: Stirring the triol acid in the presence of an acylating agent to form the 4-acyl lactone.

Step 3: Acylation of the hydroxyl at the 8-position; can be carried out chemically, or enzymatically using a hydrolase as described herein or a commercially available hydrolase.

Step 4: Selective removal of the acyl protecting group at the 4' position, either chemically or enzymatically (enzymatic hydrolysis using a hydrolase, e.g., an esterase, as described herein or a commercially available hydrolase) to yield simvastatin (see, e.g., FIG. 6, step 5, noting that in alternative aspects, the methyl (Me) group can be any alkyl, or equivalent, R— group). In one aspect, the esterase SEQ ID NO:4, encoded, e.g., by SEQ ID NO:3, is used to catalyze the selective hydrolysis of acyl groups at the lactone 4'-position. If desired, or necessary, in one aspect this step also comprises formation of the ammonium salt of simvastatin, and recrystallization of simvastatin, followed by re-lactonization. This provides simvastatin with the desired purity.

Alternatively, Step 2 can be performed by stirring the triol acid in the presence of an enzyme (e.g. a hydrolase or an esterase) and a suitable acylating agent.

In one aspect, the invention provides methods for preparing simvastatin comprising a method as set forth in FIG. 6A. The invention provides methods for preparing a triol acid from a lovastatin comprising a method as set forth in FIG. 15A or 16A. The invention provides methods for preparing a lovastatin acid from a lovastatin comprising a method as set forth in FIG. 16A. The invention provides methods for preparing a triol acid from lovastatin acid comprising a method as set forth in FIG. 16A. The invention provides methods for preparing a diol lactone from a triol acid comprising a method as set forth in FIG. 8 or FIG. 16B. The invention provides an enzymatic method for preparing an acyl lactone from a diol lactone comprising a method as set forth in FIG. 16C. The invention provides methods for preparing an acyl lactone from a triol lactone comprising a method as set forth in FIG. 16D. The invention provides methods for preparing a 4-acetyllactone from a triol acid comprising a method as set forth in FIG. 9A. The invention provides methods for preparing an acyl simvastatin from an acyl lactone comprising a method as set forth in FIG. 16E. The invention provides methods for preparing a 4-acetylsimvastatin from a 4-acetyllactone comprising a method as set forth in FIG. 9B. In one aspect, invention provides a chemical method for preparing a 4-acetylsimvastatin from a 4-acetyllactone using boron trifluoride as a catalyst, e.g., using conditions as illustrated in FIG. 9B, or a variation thereof.

The invention provides methods for preparing a simvastatin from a 4-acetylsimvastatin comprising a method as set forth in FIG. 9C or FIG. 11. The invention provides methods for preparing a simvastatin ammonium salt from an acyl simvastatin comprising a method as set forth in FIG. 16F. The invention provides methods for preparing simvastatin from a simvastatin ammonium salt comprising a method as set forth in FIG. 16F. The invention provides methods for preparing simvastatin from lovastatin via a homodiacylation route, as illustrated in FIG. 38.

Exemplary enzymes that can be used in the enzymatic hydrolysis of one, several or all of these steps include SEQ ID NO:4 (encoded by, e.g., SEQ ID NO:3), SEQ ID NO:6 (encoded by, e.g., SEQ ID NO:5), and SEQ ID NO:2 (encoded by, e.g., SEQ ID NO:1). SEQ ID NO:4 (encoded by, e.g., SEQ ID NO:3), or enzymes having 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to SEQ ID NO:2, SEQ ID NO:4, or SEQ ID NO:6.

The invention provides methods for preparing simvastatin comprising a five-step heterodiacylation method having the following steps: (a) enzymatic hydrolysis (e.g., using a polypeptide having esterase activity) of lovastatin, lovastatin acid or a salt of lovastatin acid to form a triol acid; (b) heating the triol acid or stirring in the presence of acid to form a diol lactone; (c) protecting the hydroxyl at the 4-position (4'-OH) on the lactone ring of the diol lactone by enzymatic regioselective acylation of the 4'-OH to form a 4-acyl lactone; (d) acylating the hydroxyl at the 8-position (8'-OH) of the 4-acyl lactone by chemical and/or enzymatic regioselective acylation of the 8-position to form a 4-acyl simvastatin; and (e) removing selectively the acyl protecting group at the 4' position either chemically or enzymatically, thereby, yielding simvastatin.

In alternative aspects, a method of the invention can be carried out in at least two containers, i.e., as a 2-pot, 3-pot, etc. process. A method of the invention can be carried out in any container form, e.g., a capillary array, such as GIGAMATRIX™, Diversa Corporation, San Diego, Calif.

The invention provides a homodiacylation process for the preparation of simvastatin comprising a method having the following steps: (a) enzymatic hydrolysis (e.g., using a polypeptide having esterase activity) of lovastatin, lovastatin acid or a salt of lovastatin acid to form a triol acid or a salt of a triol acid; (b) forming a diol lactone from the triol acid by lactonization; (c) acylating the 4-position (4'-OH) and 8-position (8'-OH) on the lactone ring of the diol lactone by chemical or enzymatic acylation to form a 4,8-diacyl lactone; and (d) removing selectively the acyl group at the 4' position by enzymatic hydrolysis, thereby making simvastatin.

In other aspects of the invention, other compositions can be synthesized from the diol lactone by adding alternative protecting groups at the 4- and 8-positions, e.g., where the R— group is selected from the group consisting of (i) —H, a formyl derivative; (ii) a C1-n alkyl, e.g., methyl, ethyl, propyl, butyl, etc., both straight chain and branched, wherein in one aspect n is an integer between 1 and 20; (iii) substituted alkyl groups, e.g., chloroacetyl, trichloroacetyl, trifluoroacetyl, methoxyacetyl, phenylacetyl, 4-oxopentyl (levulinate); (iv) phenyl and substituted phenyl: e.g., phenyl, p-nitrophenyl; and (v) an R'O— group, forming a carbonate protecting group, exemplified but not limited to: tBuOCO, PhOCO, PhCH$_2$OCO, where, in one aspect, the R'O— group forms a carbonate protecting group wherein R' is any group of (i), (ii), (iii) or (iv). In these alternative synthetic reactions of the invention, the protecting group (the R— group) can be regioselectively removed either chemically or enzymatically to generate the desired final product. These R— groups, or equivalent R-groups, can be used as "protecting groups" in any step of any method of the invention. For example, these R— groups, or equivalent R— groups, are used as the R— group in the exemplary processes of the invention as illustrated in FIG. 5, FIG. 6A, FIG. 9, FIG. 10, FIG. 11, FIG. 16C, FIG. 16D, FIG. 16E or FIG. 16F, or equivalent processes of the invention.

In one aspect, the invention provides a five-step route to synthesize simvastatin from lovastatin, as illustrated in FIG. 6, wherein the synthesis scheme comprises the following steps:

Step 1: Enzymatic hydrolysis of lovastatin, lovastatin acid and/or a salt of lovastatin acid to form the triol acid using an enzyme capable of catalyzing the hydrolysis of lovastatin acid, e.g., a hydrolase as described herein or a commercially available hydrolase. For example, exemplary hydrolase enzymes that can be used in the enzymatic hydrolysis of the (S)-2-methylbutyrate sidechain are the esterase enzymes: SEQ ID NO:4 (encoded by, e.g., SEQ ID NO:3), SEQ ID NO:6 (encoded by, e.g., SEQ ID NO:5), and SEQ ID NO:2 (encoded by, e.g., SEQ ID NO:1). SEQ ID NO:4 (encoded by, e.g., SEQ ID NO:3).

Step 2: Heating the triol acid or stirring in the presence of acid to form the diol lactone.

Step 3: Protection of the 4'-OH on the lactone ring by enzymatic regioselective acylation using a hydrolase as described herein or a commercially available hydrolase. See, e.g., FIG. 6, step 3, noting that in alternative aspects, the methyl (Me) group can be any alkyl, or equivalent (e.g., methoxy, alkoxy, phenyl, etc) R— group.

Step 4: Acylation of the hydroxyl at the 8-position; can be carried out chemically, or enzymatically using a hydrolase as described herein or a commercially available hydrolase.

Step 5: Selective removal of the acyl protecting group at the 4' position, either chemically or enzymatically (enzymatic hydrolysis using a hydrolase, e.g., an esterase, as described herein or a commercially available hydrolase) to yield simvastatin (see, e.g., FIG. 6, step 5, noting that in alternative aspects, the methyl (Me) group can be any allyl, or equivalent, R— group). In one aspect, the esterase SEQ ID NO:4, encoded, e.g., by SEQ ID NO:3, is used to catalyze the selective hydrolysis of acyl groups at the lactone 4'-position. If desired, or necessary, in one aspect this step also comprises formation of the ammonium salt of simvastatin, and recrystallization of simvastatin, followed by re-lactonization. This provides simvastatin with the desired purity.

The invention also provides a method to form lovastatin acid from lovastatin using an enzyme capable of catalyzing the hydrolysis of lovastatin acid, e.g., a hydrolase as described herein or a commercially available hydrolase (see step 1, Example 6, below). The invention also provides a method to form the triol acid comprising enzymatic hydrolysis of lovastatin, lovastatin acid and/or a salt of lovastatin acid to form the triol acid using an enzyme capable of catalyzing the hydrolysis of lovastatin acid, e.g., a hydrolase as described herein or a commercially available hydrolase. The invention provides a method to protect a hydroxyl on a lactone, e.g., the 4'-OH on a lactone ring (e.g., of a diol lactone, as shown in FIG. 6) by regioselective acylation, by using a hydrolase as described herein or a commercially available hydrolase. The invention provides a method for acylation of the hydroxyl at the 8-position of a 4-acyl lactone (as shown in FIG. 6), which can be carried out chemically, or enzymatically using a hydrolase as described herein or a commercially available hydrolase. The invention provides a method for selective removal of an acyl group on a lactone, e.g., a protecting acyl group on a lactone, such as the protecting acyl group at the 4' position of the lactone as shown in FIG. 6, either chemically or enzymatically. The invention also provides a method comprising two or more, or all, of these methods, e.g., to chemoenzymatically produce simvastatin from lovastatin, a triol acid, a diol lactone, a 4-acetyl lactone or 4-acetyl simvastatin. For exemplary protocols of the invention for practicing these methods, see, e.g., Examples 5, 6, 7 and 8, below.

In one aspect, diol lactone is regioselectively acylated at the 8-position using a derivative of dimethylbutyric acid and a Lewis acid catalyst.

In one aspect, the processes of the invention generate simvastatin with <1% lovastatin present, since, in some circumstances, the separation of lovastatin from simvastatin may be inefficient. In alternative aspects, the processes of the invention generate simvastatin wherein the overall yield of the process is great than or equal to (=) 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90% or more. In one aspect, the processes of the invention generate simvastatin wherein the initial enzymatic hydrolysis of lovastatin runs at about 20% w/v.

In one aspect, the invention provides a process to generate simvastatin comprising a scheme, or, variations thereof, as illustrated in FIG. 5 ("scheme 1"), which is a heterodiacylation route to synthesize simvastatin. In alternative aspects of scheme 1 (FIG. 5), step 1 can comprise a chemical or an enzymatic hydrolysis; step 2 can comprise a chemical or an enzymatic lactonization and acylation; step 3 can comprise a chemical or an enzymatic acylation, step 4 can comprise a chemical or an enzymatic hydrolysis or, any combination thereof. In one aspect, at least one of these hydrolysis reactions is regiospecific.

In alternative aspects of any of the methods of the invention, at least one step is performed in a reaction vessel. In alternative aspects of any of the methods of the invention, at least one step is performed with a cell extract. In alternative aspects of any of the methods of the invention, at least one step is performed in a whole cell. The cell can be of any source, e.g., a plant cell, a bacterial cell, a fungal cell, a mammalian cell or a yeast cell.

In one aspect of any of the methods of the invention, an ammonium salt of simvastatin is formed. In one aspect, the methods further comprise re-crystallization of the simvastatin. In one aspect, the methods comprise relactonization to provide simvastatin with a desired purity.

In one aspect of any of the methods of the invention, at least one enzymatic reaction is carried out by a hydrolase (e.g., an esterase or a lipase) encoded by a nucleic acid having at least 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:1, or enzymatically active fragments thereof. In one aspect of any of the methods of the invention, at least one enzymatic reaction is carried out by a hydrolase encoded by a nucleic acid having at least 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:3, or enzymatically active fragments thereof. In one aspect of any of the methods of the invention, at least one enzymatic reaction is carried out by a hydrolase encoded by a nucleic acid having at least 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:5, or enzymatically active fragments thereof.

In one aspect of any of the methods of the invention, at least one enzymatic reaction is carried out by a hydrolase (e.g., an esterase) having a sequence at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:2, SEQ ID NO:4 or SEQ ID NO:6, or enzymatically active fragments thereof.

The invention provides kits comprising reagents and hydrolase enzymes for practicing the methods of the invention. In one aspect, the kit comprises at least one hydrolase having a sequence at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:2, SEQ ID NO:4 or SEQ ID NO:6, or enzymatically active fragments thereof. In one aspect, the kit comprises instructions for practicing the methods of the invention.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

FIG. 2 is an illustration the results of several $BF_3.OEt_2$ catalyzed acylations, as Table 3, as discussed in detail in Example 5, below.

FIG. 3 is an illustration of Table 4, showing the impurity profile for the product of a 12 g acylation reaction, before and after precipitation, as discussed in detail in Example 5, below.

FIG. 4 is an illustration of Table 8, showing data for the isolation of simvastatin, as discussed in detail in Example 5, below.

FIG. 6A and FIG. 6B illustrate an exemplary process of the invention, a five-step route to synthesize simvastatin from lovastatin (FIG. 6A), and a summary of the conversion of lovastatin to simvastatin (FIG. 6B).

FIG. 9A illustrates an exemplary lactonization/acetylation protocol of the invention comprising generating 4-acetyllactone from triol acid, as discussed in detail in Example 7, below. FIG. 9B illustrates an exemplary method of the invention comprising generating 4-acetylsimvastatin from 4-acetyllactone, as discussed in detail in Example 5, below. FIG. 9C illustrates an exemplary method of the invention comprising the conversion of acetylsimvastatin to simvastatin, as discussed in detail in Example 5, below.

FIG. 14 illustrates a table showing a comparison of an exemplary protocol of the invention, a one step lactonization/acetylation using triol acid as the starting material, as discussed in detail in Example 7, below.

FIG. 21 illustrates a Table showing impurity profile data, HPLC assay data and elemental analysis results for selected simvastatin samples, as discussed in detail in Example 8, below.

FIG. 24 is an illustration of optimization of enzymatic hydrolysis of lovastatin by fractional factorial design using DESIGN EXPERT™ software, as described in detail in Example 10, below.

FIG. 26 illustrates results of a Response Surface Analysis (RSA) performed using central composite design for hydrolysis of Lovastatin using DESIGN EXPERT® software, as described in detail in Example 10, below.

FIG. 34 illustrates a graphic summary of data from: a 50 g reaction (a) after lactonization and concentration (FIG. 34A) and (b) the crude product (FIG. 34B).

FIG. 35 illustrates a graphic summary of data from: a 100 g reaction (a) triol acid (FIG. 35A) and (b) after lactonization (FIG. 35B).

DETAILED DESCRIPTION

The present invention provides novel synthetic chemical and biochemical processes for the production of simvastatin (e.g., ZOCOR™) and its intermediates. These methods can be efficient and cost-effective.

In various aspects of the invention, the methods catalyze reactions biocatalytically using various enzymes, including hydrolases, e.g., acylases and esterases. In one aspect, the invention provides methods for the enzymatic hydrolysis of lovastatin to lovastatin acid using hydrolases. In one aspect, the invention provides methods for enzymatic hydrolysis of lovastatin acid or salts thereof to triol acid or salts thereof. In one aspect, the invention provides methods for the enzymatic acylation of diol lactone to an acyl lactone using hydrolases. In one aspect, the invention provides methods for the enzymatic acylation of an acyl lactone to an acyl simvastatin using hydrolases. In one aspect, the invention provides methods for hydrolyzing a lactone ring using hydrolases.

The invention includes methods for producing simvastatin and various intermediates via in vitro or in vivo techniques, e.g., whole cells protocols, such as fermentation or other biocatalytic processes.

Figure 5:
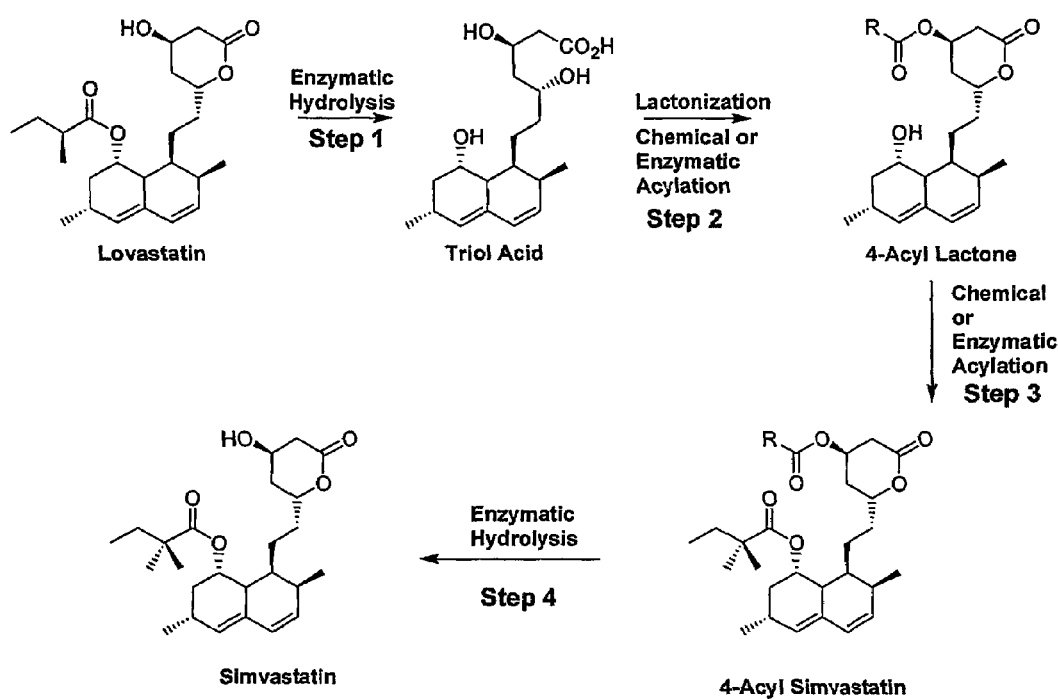
FIG. 5 illustrates an exemplary process of the invention, a four-step heterodiacylation route to synthesize simvastatin from lovastatin.

In alternative aspects, the invention provides novel processes for the conversion of lovastatin into simvastatin, as illustrated in FIG. 5, or, FIGS. 6A and 6B. In one aspect diol lactone made from lovastatin via hydrolysis is regioselectively acylated at the 8-position using a derivative of dimethylbutyric acid and a Lewis acid catalyst. Diol lactone can be made from lovastatin using chemoenzymatic processes described herein.

Figure 17A:
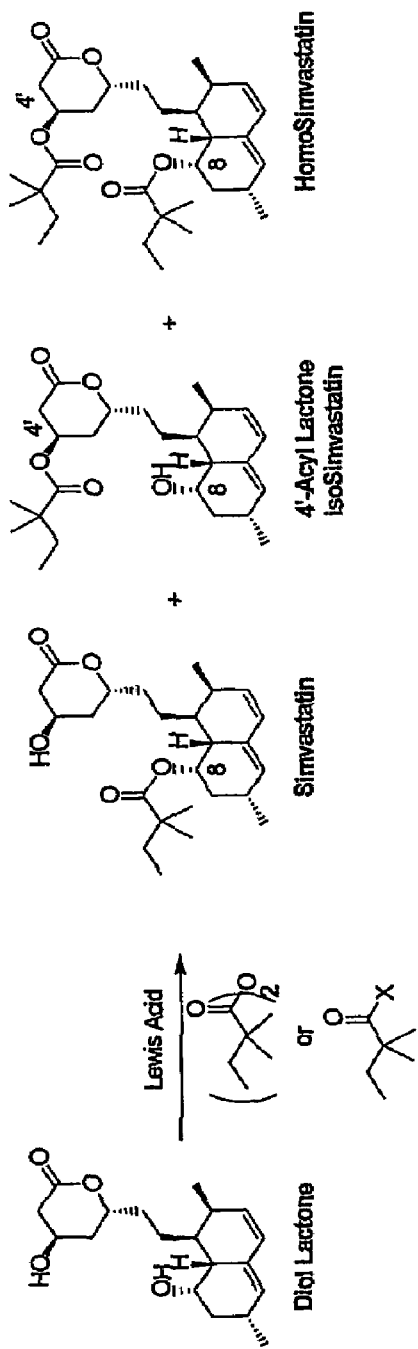
FIG. 17A illustrates an exemplary reaction of the invention comprising a process for making simvastatin, 4'-acyl lactone (also called isosimvastatin) and homosimvastatin (also called bissimvastatin) from diol lactone using a Lewis acid, as discussed in detail, below.

In one aspect, the invention provides a process comprising making simvastatin, 4'-acyl simvastatin and homosimvastatin from diol lactone using a Lewis acid, as illustrated in FIG. 17A. The inventors have found that the treatment of diol lactone with a carboxylic acid derivative in the presence of a Lewis acid catalyst results in predominant acylation at the 8-position. When excess vinyl acetate is used in the presence of a metal triflate, the 8-acetyl derivate is formed almost exclusively at low conversion. Results to date show that the treatment of diol lactone with a combination of dimethylbutyric anhydride, and $Bi(OTf)_3$ or $Cu(OTf)_2$ in dichloromethane at room temperature results in a rapid reaction in which the simvastatin: 4'-acyl lactone ratio is >4:1.

In one aspect, the isolation and purification of simvastatin is by crystallization. In one aspect, the invention provides methods for screening Lewis acid catalysts and/or acylation agents to provide alternative reaction conditions to maximize the yield of simvastatin and minimize the side products. Maximizing the yield of simvastatin and minimizing the side products helps in crystallization protocols. Use of crystallization to isolate/purify simvastatin results in an exemplary 2-step process from lovastatin to simvastatin.

Figure 17B:
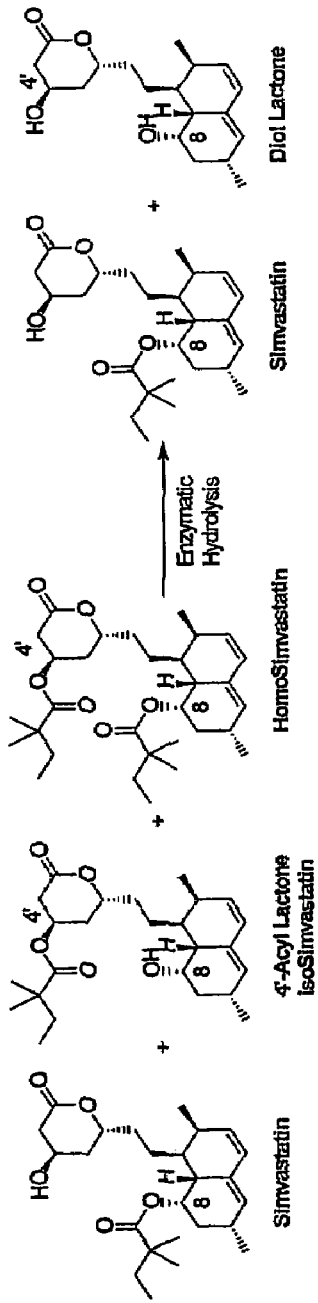
FIG. 17B illustrates an exemplary reaction of the invention comprising making simvastatin and diol lactone from simvastatin, 4'-acyl lactone (isosimvastatin) and homosimvastatin (also called bissimvastatin) by enzymatic hydrolysis, as discussed in detail, below.

In one aspect, the invention provides a process comprising making simvastatin and diol lactone from simvastatin, 4'-acyl lactone simvastatin and homosimvastatin by enzymatic hydrolysis, as illustrated in FIG. 17B.

In one aspect, if isosimvastatin and homosimvastatin cannot be reduced to levels that can be purged by crystallization, a final enzymatic hydrolysis step is employed to facilitate the recovery of product. In one aspect, the treatment of mixtures of simvastatin, isosimvastatin and homosimvastatin with an esterase (e.g., enzyme having a sequence as set forth in SEQ ID NO:4, encoded by SEQ ID NO:3), results in the regioselective hydrolysis of the acyl group at the 4'-position, resulting in a mixture of simvastatin and diol lactone. In one aspect, the simvastatin is separated by crystallization.

Alternatively, the use of excess anhydride can be used to push the reaction towards the formation of simvastatin and homosimvastatin. This can minimize the amount of isosimvastatin. Enzymatic hydrolysis of such mixtures results in the formation and ready isolation of simvastatin.

In one aspect of the preparation of simvastatin by regioselective acylation of diol lactone in the presence of Lewis acids, Diol lactone was treated with dimethylbutyric anhydride (0.5 equivalents (eq)) in dichloromethane at room temperature (RT) in the presence of 5 mol % $Cu(OTf)_2$ as catalyst. HPLC analysis indicated 50% conversion of diol lactone within 10 minutes. The ratio of simvastatin (acylation at the 8-position) to isosimvastatin (acylation at the 4-position), was 4:1, with ~4% homosimvastatin being formed.

In one aspect, the invention provides processes comprising steps as set forth in the novel four-step process of FIG. 5 or the five-step process of FIG. 6A, or a combination thereof. In alternative aspects, the invention provides processes comprising at least one, several or all, of the following steps:

Step 1: Enzymatic hydrolysis of lovastatin, lovastatin acid or a salt of lovastatin acid to form the triol acid or a salt of a triol acid using a hydrolase enzyme, e.g., an enzyme described herein, e.g., SEQ ID NO:4, encoded by, e.g., SEQ ID NO:3, or a commercially available hydrolase.

Step 2: Converting the triol acid to a 4-acetyl lactone, e.g., in one step as in step 2 of FIG. 5, or, in two steps as in steps 2 and 3 of FIG. 6A (in one aspect, the triol acid is heated or stirred in the presence of acid to form a diol lactone).

Step 3: Protection of the 4'-OH on the lactone ring of a diol lactone to form a 4-acetyl lactone by regioselective enzymatic acylation using, e.g., an enzyme as described herein or a commercially available hydrolase Step 4: Acylation of the hydroxyl at the 8-position; can be carried out chemically, or enzymatically using, e.g., an enzyme described herein or a commercially available hydrolase.

Step 5: Selective removal of the acyl protecting group at the 4' position, either chemically or enzymatically, yields simvastatin. If necessary, formation of the ammonium salt of simvastatin, and recrystallization of simvastatin, followed by re-lactonization, provides simvastatin with the desired purity.

Figure 16A:
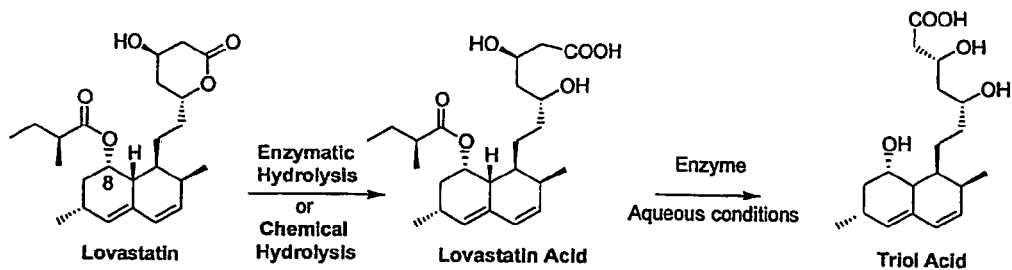
FIG. 16A illustrates an exemplary method for making lovastatin acid from lovastatin, and triol acid from lovastatin acid, as discussed in detail in Example 6, below.

In one aspect, referring to step 1, as described above, the invention provides a process comprising making lovastatin acid from lovastatin by enzymatic or chemical hydrolysis, as illustrated in FIG. 16A. The invention provides a process comprising making triol acid or a triol salt from lovastatin acid by enzymatic or chemical hydrolysis, as illustrated in FIG. 16A.

Complete, or substantially complete (in alternative aspects, >99%, >98%, >97% or >96%) removal of the methylbutyrate sidechain may be essential for a process because of the difficulty in separating lovastatin and simvastatin, and the low allowable levels of lovastatin in simvastatin API. Reported procedures for the hydrolysis of lovastatin require the use of high temperatures and long reaction times for complete reaction.

In one aspect, Lovastatin is hydrolyzed under mild conditions using a hydrolase enzyme (e.g., enzyme having a sequence as set forth in SEQ ID NO:2, SEQ ID NO:4, or SEQ ID NO:6, encoded by SEQ ID NO:1, SEQ ID NO:3 or SEQ ID NO:5, respectively). This results in hydrolysis of the lactone ring and complete removal of the side-chain in the 8-position. The enzymes having a sequence as set forth in SEQ ID NO:1, SEQ ID NO:3 and SEQ ID NO:5 have been demonstrated to be particularly effective for the enzymatic hydrolysis of the methylbutyrate sidechain: SEQ ID NO:2, SEQ ID NO:4, SEQ ID NO:6. The enzyme having a sequence as set forth in SEQ ID NO:4 has been subcloned and expressed in hosts such as E. coli.

Lovastatin can show poor solubility under the aqueous conditions necessary for enzymatic activity. Thus, in one alternative aspect, a suspension of lovastatin in water is raised to pH>12 to effect a rapid hydrolysis of the lactone ring. This results in the in-situ formation of the more soluble lovastatin acid salt. In one aspect, the pH of the reaction mixture is then readjusted downward to a range suitable for the enzymatic reaction; and the enzyme is added.

The enzymatic hydrolysis conditions may also be applied to mixtures of lovastatin and lovastatin acid extracted directly from fermentation broth. Alternatively, the enzyme may be added to the fermentation broth and the triol acid isolated directly.

In one aspect, after hydrolysis, the reaction mixture is acidified. The triol acid can be isolated by extraction and/or filtration and used directly in the next step. Alternatively, the triol acid is isolated as a solid after a suitable crystallization/precipitation step.

Figure 16B:
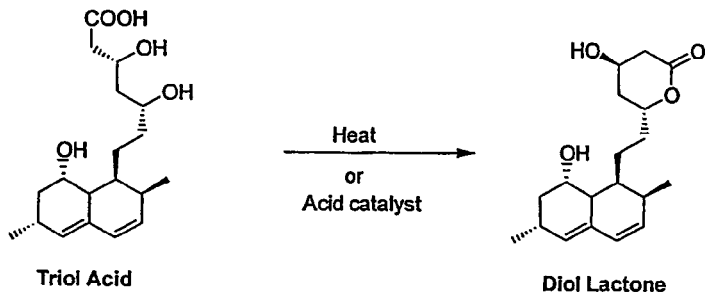
FIG. 16B illustrates an exemplary method for making diol lactone from triol acid, as discussed in detail in Example 6, below.

In one aspect, referring to step 2, as described above, the invention provides a process comprising steps as illustrated in FIG. 16B. In one aspect, the triol acid is re-lactonized by heating in a suitable solvent and driving the equilibrium to the lactone form by removal of water by conventional means. Alternatively, stirring in the presence of a suitable acid will effect closure of the lactone ring.

In one aspect, referring to step 3, as described above, the invention provides a process comprising acylation of the hydroxyl group in the 4'-position enzymatically using an enzyme with the desired activity and selectivity, e.g., a hydrolase, such as an esterase. In one aspect, hydrolases (e.g., esterases) are used to acylate diol lactones. The nature of the acyl group can be varied to impart suitable properties, e.g., acetate for ease of removal, benzoate for enhanced crystallinity, formate for enhanced water solubility.

In alternative aspects of the exemplified methods described herein (e.g., FIGS. 5 and 6A, FIG. 38), including the reactions and reagents as illustrated in Steps 3 (supra), 4 and 5 (infra), the acyl can be substituted for any appropriate R— group (i.e., the "protecting" group can be any R— group), wherein "R" can be:

(i) —H, a formyl derivative;
(ii) a C1-n allyl, both straight chain and branched;
(iii) substituted alkyl groups, e.g., chloroacetyl, trichloroacetyl, trifluoroacetyl, methoxyacetyl, phenylacetyl, 4-oxopentyl (levulinate);
(iv) phenyl and substituted phenyl: e.g., phenyl, p-nitrophenyl;
(v) an R'O— group, forming a carbonate protecting group, exemplified but not limited to: tBuOCO, PhOCO, PhCH$_2$OCO.

In one aspect, the R'O— group forms a carbonate protecting group and R' is any group of (i), (ii), (iii) or (iv). In one aspect, an enzyme with enhanced reactivity on long-chain alkyl esters is used when R is a long-chain alkyl group. Solubility may be a problem when R is a long-chain alkyl group. In one aspect, R is an acetate, which can be advantageous due to (i) ease of installation, (ii) good enzyme activity for hydrolysis, (iii) solubility, (iv) cost of reagents.

Figure 16C:
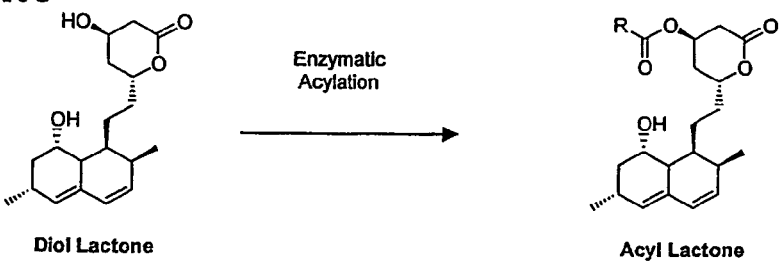
FIG. 16C illustrates an exemplary method for making acyl lactone from diol lactone, as discussed in detail in Example 6, below.
Figure 16D:
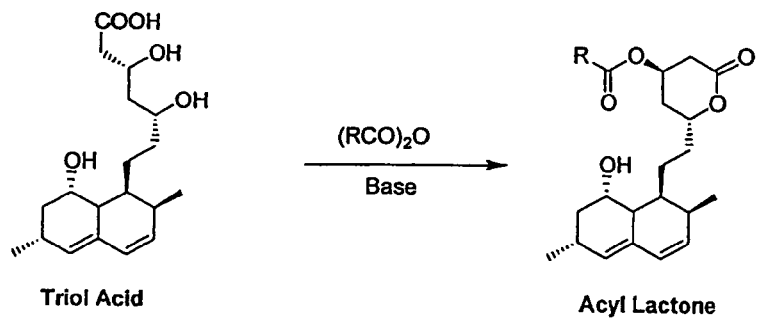
FIG. 16D illustrates an exemplary protocol of the invention comprising lactonization and acylation at the lactone 4-position, as discussed in detail in Example 6, below.
Figure 16E:
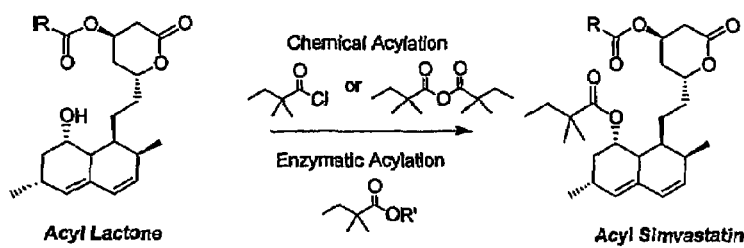
FIG. 16E illustrates an exemplary protocol of the invention comprising making acyl simvastatin from acyl lactone, as discussed in detail in Example 6, below.

In one aspect, referring to step 4, as described above, the invention provides a process comprising steps, and, in alternative embodiments, the reagents, as illustrated in FIG. 16E. In one aspect, a combination of a dimethylbutyric acid derivative with a suitable acylation catalyst (by chemical acylation or enzymatic acylation) is used to install the desired simvastatin side-chain. The combination of dimethylbutyric anhydride/Lewis acid (e.g., Bi(triflate)$_3$, Cu(triflate)$_2$), results in rapid reaction at room temperature (RT).

In one aspect, the invention provides methods for screening suitable Lewis acids and reaction conditions, including temperature, solvents etc. Optimum conditions for this acylation for alternative protocols or reagents can be determined using routing screening methods.

In one aspect, enzyme catalyzed acylation of the acyl lactone is used to install the dimethylbutyrate group at the 8-position under very mild conditions (for example, in one aspect, at RT, e.g., about 40° C., using organic solvent), without formation of side products.

The invention provides methods for screening for alternative enzymes that have the desired activity in the methods of the invention. Enzymes can be screened for their effectiveness in various protocols of the invention using routine methods.

Figure 16F:
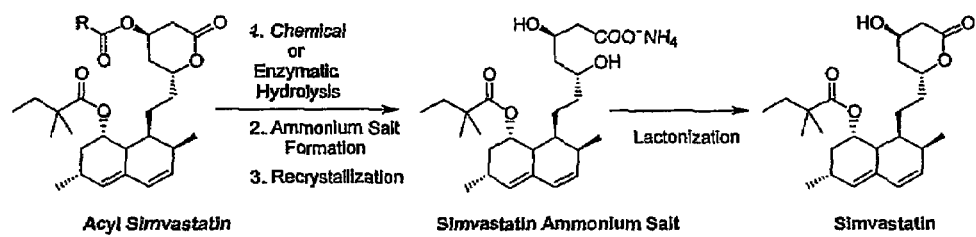
FIG. 16F illustrates an exemplary protocol of the invention comprising making simvastatin ammonium salt from acyl simvastatin, and simvastatin from simvastatin ammonium salt, as discussed in detail in Example 6, below.

In one aspect, referring to step 5, as described above, the invention provides a process comprising steps, and, in alternative embodiments, the reagents, as illustrated in FIG. 16F.

In one aspect, the final steps require the selective removal of the acyl group at the 4'-position. The acyl group at the 4'-position can be highly susceptible to base-catalyzed elimination, even under only slightly basic conditions. Consequently, the enzymatic hydrolysis has been the most convenient method for regioselective removal of this acyl group. It has been demonstrated that the same enzyme that hydrolyzes lovastatin (SEQ ID NO:4 (encoded by SEQ ID NO:3), in step 1, above) is also an effective catalyst for the selective hydrolysis of acyl groups at the lactone 4'-position. When carried out at pH 7, this enzymatic hydrolysis yields simvastatin with the lactone ring substantially intact.

General Methods

The present invention provides novel biochemical processes for the production of simvastatin and various intermediates. The skilled artisan will recognize that the starting and intermediate compounds used in the methods of the invention can be synthesized using a variety of procedures and methodologies, which are well described in the scientific and patent literature, e.g., Organic Syntheses Collective Volumes, Gilman et al. (Eds) John Wiley & Sons, Inc., NY; Venuti (1989) *Pharm Res.* 6:867-873. The invention can be practiced in conjunction with any method or protocol known in the art, which are well described in the scientific and patent literature.

The discussion of the general methods given herein is intended for illustrative purposes only. Other alternative methods and embodiments will be apparent to those of skill in the art upon review of this disclosure.

Enzymes

In one aspect of any of the methods of the invention, at least one enzymatic reaction is carried out by a polypeptide having hydrolase activity (e.g., an esterase activity), for example, a hydrolase having a sequence at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:2, SEQ ID NO:4 or SEQ ID NO:6, or enzymatically active fragments thereof. The polypeptide having hydrolase activity can also be a peptide comprising a catalytic site, a catalytic antibody, and the like.

The polypeptide having a sequence as set forth in SEQ ID NO:4 is a family VII esterase, having homology to beta-lactamases and shares the SXXK motif. Thus, enzymes that can be used in one, several or all steps of a method of the invention can have esterase activity and have a sequence at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:4 and an SXXK motif.

The polypeptide having a sequence as set forth in SEQ ID NO:2 or SEQ ID NO:6 are feruloyl esterases. Thus, enzymes that can be used in one, several or all steps of a method of the invention can have feruloyl esterase activity.

Enzymes used in the methods of the invention can be produced by any synthetic or recombinant method, or, they may be isolated from a natural source, or, a combination thereof. Nucleic acids encoding enzymes used to practice the methods of the invention, whether RNA, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems. Nucleic acids used to practice the methods of the invention can be generated using amplification methods, which are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario).

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440 3444; Frenkel (1995) Free Radic. Biol. Med. 19:373 380; Blommers (1994) Biochemistry 33:7886 7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993). Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

The nucleic acids and proteins of the invention can be detected, confirmed and quantified by any of a number of means well known to those of skill in the art. General methods for detecting both nucleic acids and corresponding proteins include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. The detection of nucleic acids and polypeptides can be by well known methods such as Southern analysis, northern analysis, gel electrophoresis, PCR, radiolabeling, scintillation counting, and affinity chromatography.

In various steps of exemplary methods of the invention, a polypeptide having esterase activity, e.g., an esterase enzyme, is used. Any esterase, or enzyme (e.g., a hydrolase) or other polypeptide having a similar activity (e.g., a catalytic antibody or a peptide comprising an active site) can be used.

Any method for screening for enzymes for use in the methods of the invention, e.g., enzymes for the hydrolysis of lovastatin, lovastatin acid, 4-acetyl simvastatin or simvastatin, can be used, and, these methods are well known in the art. For example, in one exemplary set of screen conditions used to determine an enzyme(s) to be used in a method of the invention comprises use of 2.5 mM substrate, 100 mM phosphate buffer/co-solvent pH 7 to pH 8, 30° C., 48 h, with the following composition: (i) lovastatin or simvastatin in MTBE/buffer, (ii) lovastatin or simvastatin in toluene/buffer, (iii) lovastatin acid or simvastatin acid in 10% methanol/buffer. Screen results were confirmed at 1 mM substrate.

Using this exemplary assay, it was determined that three enzymes having sequences as set forth in SEQ ID NO:2, SEQ ID NO:4 and SEQ ID NO:6, were active for the hydrolysis of lovastatin or lovastatin acid. Only an enzyme having a sequence as set forth in SEQ ID NO:4 showed activity for the hydrolysis of simvastatin. SEQ ID NO:4 and SEQ ID NO:2 were further evaluated at 25, 50 and 100 mM lovastatin acid in 10% MeOH/buffer, pH 9, the more soluble lovastatin acid being used as substrate for convenience. SEQ ID NO:4 showed high conversion of substrate in many cases, with solution yields of 12-60% triol acid.

Genomic clones comprising sequences encoding enzymes having sequences as set forth in SEQ ID NO:4, SEQ ID NO:2, SEQ ID NO:6 (e.g., encoded by exemplary SEQ ID NO:3, SEQ ID NO:1, and SEQ ID NO:5, respectively), were compared for the hydrolysis of lovastatin acid under standard conditions (the same total protein concentration, or the same enzyme activity normalized against the fluorescent substrate, methylumbelliferyl butyrate (MUB)). Enzymes having a sequence comprising SEQ ID NO:4 showed the best activity under the reaction conditions.

The genomic clones comprising sequences encoding enzymes having sequences as set forth in SEQ ID NO:4 and SEQ ID NO:2 (e.g., encoded by exemplary SEQ ID NO:3 and SEQ ID NO:1, respectively), were subcloned. SEQ ID NO:2 has a leader sequence which is believed to be required for secretion/localization, and was subcloned with and without the leader sequence. The subclones were assayed against MUB and lovastatin acid; only the SEQ ID NO:2—encoding subclone with the leader sequence showed activity against MUB. Furthermore, none of the subclones showed activity on lovastatin acid.

Transposon insertion experiments with the genomic clone comprising a nucleic acid encoding SEQ ID NO:4 identified the gene responsible for the lovastatin esterase activity. This gene encoded an esterase with a predicted 43 kD molecular weight; the identity was further confirmed by isolating the 43 kD band from a native gel and confirming activity on lovastatin acid and by MS analysis. The E. coli construct comprising a nucleic acid encoding SEQ ID NO:4 was capable of hydrolyzing lovastatin to give a 93-98% conversion to triol acid in 21 h at 35° C. at 350 mM substrate.

Capillary Arrays

The methods of the invention, and/or, screening protocols used to determine enzyme(s) to be used in a method of the invention, can be practiced in whole or in part by capillary arrays, such as the GIGAMATRIX™, Diversa Corporation, San Diego, Calif. See, e.g., WO0138583. Reagents or polypeptides (e.g., enzymes) can be immobilized to or applied to an array, including capillary arrays. Capillary arrays provide another system for holding and screening reagents, catalysts (e.g., enzymes) and products. The apparatus can further include interstitial material disposed between adjacent capillaries in the array, and one or more reference indicia formed within of the interstitial material. High throughput screening apparatus can also be adapted and used to practice the methods of the invention, see, e.g., U.S. Patent Application No. 20020001809.

Whole Cell-Based Methods

The methods of the invention can be practiced in whole or in part in a whole cell environment. The invention also provides for whole cell evolution, or whole cell engineering, of a cell to develop a new cell strain having a new phenotype to be used in the methods of the invention, e.g., a new cell line comprising one, several or all enzymes used in a method of the invention. This can be done by modifying the genetic composition of the cell, where the genetic composition is modified by addition to the cell of a nucleic acid, e.g., a coding sequence for an enzyme used in the methods of the invention. See, e.g., WO0229032; WO0196551.

The host cell for the "whole-cell process" may be any cell known to one skilled in the art, including prokaryotic cells, eukaryotic cells, such as bacterial cells, fungal cells, yeast cells, mammalian cells, insect cells, or plant cells.

To detect the production of an intermediate or product of the methods of the invention, or a new phenotype, at least one metabolic parameter of a cell (or a genetically modified cell) is monitored in the cell in a "real time" or "on-line" time frame by Metabolic Flux Analysis (MFA). In one aspect, a plurality of cells, such as a cell culture, is monitored in "real time" or "on-line." In one aspect, a plurality of metabolic parameters is monitored in "real time" or "on-line."

Metabolic flux analysis (MFA) is based on a known biochemistry framework. A linearly independent metabolic matrix is constructed based on the law of mass conservation and on the pseudo-steady state hypothesis (PSSH) on the intracellular metabolites. In practicing the methods of the invention, metabolic networks are established, including the:

identity of all pathway substrates, products and intermediary metabolites identity of all the chemical reactions interconverting the pathway metabolites, the stoichiometry of the pathway reactions, identity of all the enzymes catalyzing the reactions, the enzyme reaction kinetics, the regulatory interactions between pathway components, e.g. allosteric interactions, enzyme-enzyme interactions etc, intracellular compartmentalization of enzymes or any other supramolecular organization of the enzymes, and, the presence of any concentration gradients of metabolites, enzymes or effector molecules or diffusion barriers to their movement.

Once the metabolic network for a given strain is built, mathematic presentation by matrix notion can be introduced to estimate the intracellular metabolic fluxes if the on-line metabolome data is available. Metabolic phenotype relies on the changes of the whole metabolic network within a cell. Metabolic phenotype relies on the change of pathway utilization with respect to environmental conditions, genetic regulation, developmental state and the genotype, etc. In one aspect of the methods of the invention, after the on-line MFA calculation, the dynamic behavior of the cells, their phenotype and other properties are analyzed by investigating the pathway utilization.

Control of physiological state of cell cultures will become possible after the pathway analysis. The methods of the invention can help determine how to manipulate the fermentation by determining how to change the substrate supply, temperature, use of inducers, etc. to control the physiological state of cells to move along desirable direction. In practicing the methods of the invention, the MFA results can also be compared with transcriptome and proteome data to design experiments and protocols for metabolic engineering or gene shuffling, etc. Any aspect of metabolism or growth can be monitored.

Monitoring Expression of an mRNA Transcript

In one aspect of the invention, the engineered phenotype comprises increasing or decreasing the expression of an mRNA transcript or generating new transcripts in a cell. This increased or decreased expression can be traced by use of a fluorescent polypeptide, e.g., a chimeric protein comprising an enzyme used in the methods of the invention. mRNA transcripts, or messages, also can be detected and quantified by any method known in the art, including, e.g., Northern blots, quantitative amplification reactions, hybridization to arrays, and the like. Quantitative amplification reactions include, e.g., quantitative PCR, including, e.g., quantitative reverse transcription polymerase chain reaction, or RT-PCR; quantitative real time RT-PCR, or "real-time kinetic RT-PCR" (see, e.g., Kreuzer (2001) Br. J. Haematol. 114: 313-318; Xia (2001) Transplantation 72:907-914).

In one aspect of the invention, the engineered phenotype is generated by knocking out expression of a homologous gene. The gene's coding sequence or one or more transcriptional control elements can be knocked out, e.g., promoters enhancers. Thus, the expression of a transcript can be completely ablated or only decreased.

In one aspect of the invention, the engineered phenotype comprises increasing the expression of a homologous gene. This can be effected by knocking out of a negative control element, including a transcriptional regulatory element acting in cis- or trans-, or, mutagenizing a positive control element. One or more, or, all the transcripts of a cell can be measured by hybridization of a sample comprising transcripts of the cell, or, nucleic acids representative of or complementary to transcripts of a cell, by hybridization to immobilized nucleic acids on an array.

Monitoring Expression of a Polypeptides, Peptides and Amino Acids

In one aspect of the invention, the engineered phenotype comprises increasing or decreasing the expression of a polypeptide or generating new polypeptides in a cell. This increased or decreased expression can be traced by use of a fluorescent polypeptide, e.g., a chimeric protein comprising an enzyme used in the methods of the invention. Polypeptides, reagents and end products (e.g., simvastatin) also can be detected and quantified by any method known in the art, including, e.g., nuclear magnetic resonance (NMR), spectrophotometry, radiography (protein radiolabeling), electrophoresis, capillary electrophoresis, high performance liquid chromatography (HPLC), thin layer chromatography (TLC), hyperdiffusion chromatography, various immunological methods, e.g. immunoprecipitation, immunodiffusion, immuno-electrophoresis, radioimmunoassays (RIAs), enzyme-linked immunosorbent assays (ELISAs), immunofluorescent assays, gel electrophoresis (e.g., SDS-PAGE), staining with antibodies, fluorescent activated cell sorter (FACS), pyrolysis mass spectrometry, Fourier-Transform Infrared Spectrometry, Raman spectrometry, GC-MS, and LC-Electrospray and cap-LC-tandem-electrospray mass spectrometries, and the like. Novel bioactivities can also be screened using methods, or variations thereof, described in U.S. Pat. No. 6,057,103. Polypeptides of a cell can be measured using a protein array.

Determining the Degree of Sequence Identity

In one aspect of any of the methods of the invention, at least one step of the process comprises an enzymatic reaction (e.g., an acylation) carried out by a hydrolase (e.g., an esterase, or acylase) encoded by a nucleic acid having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:1, SEQ ID NO:3 and/or SEQ ID NO:5, or enzymatically active fragments thereof (or, alternatively, commercially available hydrolase enzymes). In one aspect of any of the methods of the invention, at least one enzymatic reaction is carried out by a hydrolase, e.g., an esterase, or acylase, having a sequence at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:2, SEQ ID NO:4 or SEQ ID NO:6, or enzymatically active fragments thereof (or, alternatively, commercially available hydrolase enzymes).

Enzymatic activity can be determined by routine screening using known protocols, or, the methods of the invention, as described herein. For example, enzymatic activity can be determined by testing whether a polypeptide or peptide can hydrolyze a lactone ring, or, enzymatically acylate a diol lactone, as described herein.

Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (see, e.g., Pearson (1988) Proc. Natl. Acad. Sci. USA 85(8): 2444-2448; Altschul (1990) J. Mol. Biol. 215(3):403-410; Thompson (1994) Nucleic Acids Res. 22(2):4673-4680; Higgins et al., Methods Enzymol. 266:383-402, 1996; Altschul et al., J. Mol. Biol. 215(3):403-410, 1990; Altschul et al., Nature Genetics 3:266-272, 1993).

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the numbers of contiguous residues. For example, in alternative aspects of the invention, contiguous residues ranging anywhere from about 20 to the full length of an exemplary polypeptide or nucleic acid sequence of the invention are compared to a reference sequence of the same number of contiguous positions after the two sequences are optimally aligned. If the reference sequence has the requisite sequence identity to an exemplary polypeptide or nucleic acid sequence of the invention, e.g., 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to SEQ ID NO:1, SEQ ID NO:2, SEQ ID NO:3, SEQ ID NO:4, SEQ ID NO:5 or SEQ ID NO:6, and the sequence is or encodes a hydrolase, that sequence can be used in at least one step of a method of the invention. In alternative embodiments, subsequences ranging from about 20 to 600, about 50 to 200, and about 100 to 150 are compared to a reference sequence of the same number of contiguous positions after the two sequences are optimally aligned. Methods of alignment of sequence for comparison are well known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. Databases containing genomic information annotated with some functional information are maintained by different organization, and are accessible via the internet.

BLAST, BLAST 2.0 and BLAST 2.2.2 algorithms are also used to practice the invention. They are described, e.g., in Altschul (1977) Nuc. Acids Res. 25:3389-3402; Altschul (1990) J. Mol. Biol. 215:403-410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASIN program (for nucleotide sequences) uses as defaults a wordlength (W) of 11, an expectation (E) of 10, M=5, N=4 and a comparison of both strands. For arnino acid sequences, the BLASTP program uses as defaults a wordlength of 3, and expectations (E) of 10, and the BLOSUM62 scoring matrix (see Henikoff & Henikoff (1989) Proc. Natl. Acad. Sci. USA 89:10915) alignments (B) of 50, expectation (E) of 10, M=5, N=4, and a comparison of both strands. The BLAST algorithm also performs a statistical analysis of the similarity between two sequences (see, e.g., Karlin & Altschul (1993) Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001. In one aspect, protein and nucleic acid sequence homologies are evaluated using the Basic Local Alignment Search Tool ("BLAST"). For example, five specific BLAST programs can be used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands)

against a protein sequence database; (4) TBLASTN compares a query protein sequence against a nucleotide sequence database translated in all six reading frames (both strands); and, (5) TBLASTX compares the six-frame translations of a nucleotide query sequence against the six-flame translations of a nucleotide sequence database. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation).

In one aspect of the invention, the NCBI BLAST 2.2.2 programs is used, default options to blastp. There are about 38 setting options in the BLAST 2.2.2 program. In this exemplary aspect of the invention, all default values are used except for the default filtering setting (i.e., all parameters set to default except filtering which is set to OFF); in its place a "—F F" setting is used, which disables filtering. Use of default filtering often results in Karlin-Altschul violations due to short length of sequence.

The default values used in this exemplary aspect of the invention include:
"Filter for low complexity: ON
Word Size: 3
Matrix: Blosum62
Gap Costs: Existence: 11
Extension: 1"

Other default settings can be: filter for low complexity OFF, word size of 3 for protein, BLOSUM62 matrix, gap existence penalty of −11 and a gap extension penalty of −1. An exemplary NCBI BLAST 2.2.2 program setting has the "—W" option default to 0. This means that, if not set, the word size defaults to 3 for proteins and 11 for nucleotides.

The invention will be further described with reference to the following examples; however, it is to be understood that the invention is not limited to such examples.

EXAMPLES

Example 1

Chemoenzymatic Production of Simvastatin

The following example describes an exemplary protocol of the invention, e.g., for the chemoenzymatic production of Simvastatin.

Enzymatic Hydrolysis of Lovastatin

The enzyme having a sequence as set forth in SEQ ID NO:4 (encoded by SEQ ID NO:3) was evaluated at 0.1 to 0.5 M concentrations of lovastatin or lovastatin acid in 7-10% MeOH/buffer, with the reaction being maintained at pH 9-9.5 by automatic addition of base. For example, at 0.5M lovastatin on a 500 mL scale using a lyophilized preparation of enzyme SEQ ID NO:4 (centrifuged supernatant from lysed cells) containing 14 mg/mL total protein, complete conversion of substrate was observed after 48 h.

The reaction mixture was acidified (pH 2), and the precipitate collected by centrifugation and dried. The filtrate was extracted with iPrOAc and the organic extract was added to the dried filter cake. The resulting suspension was heat to reflux in a Dean-Stark apparatus until lactonization was complete. The resulting solution was filtered through a Celite pad, and the filtrate was washed with satd. $NaHCO_3$. The resulting iPrOAc solution was concentrated until (×0.5), diluted with hexanes and cooled to 0° C. The precipitated solid was filtered and air-dried to yield diol lactone (63 g, 79.5% isolated yield; another 10.3 g of product was identified in various washes and mother liquors). The product contained <1% lovastatin.

Enzymatic Acylation of Diol Lactone

A mixture of diol lactone (25 mM), vinyl acetate (250 mM) and *Candida antarctica* lipase B (33 mg) in TBME (1 mL) was shaken at RT. After 44 h HPLC indicated the formation of the monoacetate with 60% conversion.

Preparation of Acetyl Simvastatin

4-Acetyl lactone was dried under vacuum overnight at room temperature, stored under nitrogen, then dissolved in anhydrous methylene chloride (1 g/2.5-3 ml ratio) at room temperature under nitrogen. Meanwhile, $Cu(OTf)_2$ (5 mol %) was dissolved in the minimum amount of acetonitrile at room temperature, then 1.05-1.2 eq of dimethylbutyric anhydride was added to the solution, stirring at room temperature for 30 min to hour. This $Cu(OTf)_2$/anhydride solution was transferred into the 4-Acetyl lactone solution through syringe at room temperature under nitrogen with stirring. When complete (monitored by HPLC), the reaction was quenched by addition of water, and washed with satd., $NaHCO_3$ The isolated organic layer was dried over $Na_2SO_4$, filtered and evaporated to obtain crude 4-acetyl simvastatin (>99%).

Enzymatic Hydrolysis of Acetyl Simvastatin 3.22 g Acetylsimvastatin (final concentration 350 mM);
2 ml MeOH; 100 µl 4M Tris; 9.9 ml water;
8 ml esterase (SEQ ID NO:4, encoded, e.g., by SEQ ID NO:3), 125 mg/ml lyophilized lysate in water.

The reaction is performed in a 25 ml vessel with overhead stirring and a magnetic stirrer bar. pH-stat conditions are maintained by a DasGip STIRRER-PRO® system; a pH of 7 is maintained by addition of 10% $NH_4OH$. As the conversion approaches ~75%, 4 ml of toluene are added to solubilize the material. The reaction is allowed to proceed overnight, at which time further solvent (toluene or methylene chloride) is added to ensure that all insoluble material is dissolved. Final composition of the reaction: Simvastatin acid 4.7%, Simvastatin 90.9%, Acetyl simvastatin 0.9%, Putative elimination product of simvastatin 3.5%. Final conversion 95.6%.

Example 2

Lovastatin Esterase Assay

In one aspect, the invention provides methods comprising the enzymatic hydrolysis of lovastatin, lovastatin acid or a salt of lovastatin acid to form the triol acid using a hydrolase enzyme, e.g., an enzyme of the invention, e.g., SEQ ID NO:4, encoded by SEQ ID NO:3. In one aspect, the invention provides methods comprising the enzymatic hydrolysis of lovastatin, lovastatin acid or a salt of lovastatin acid to form simvastatin.

The following example describes an exemplary lovastatin esterase assay which can be used to practice the methods of the invention For example, this exemplary assay can be used to determine if a hydrolase enzyme, e.g., an esterase, can be used to practice a method of the invention.

(a) Cell Lysis (Assay Scale):

An ice-cold lysis solution (enough for 9 samples) was prepared from B-PER (4.5 µL) (Pierce, #78248), lysozyme (200 μL) (Sigma, L-6876; stock solution 10 mg/ml), and DNase I (40 μL) (Sigma, DN-25; stock solution 5 mg/mL).

Meanwhile 50 μL of culture was resuspended by vortex in 950 μL water and centrifuged for 15 min at 4° C. at 16,000 g. The resulting cell pellet was resuspended in 50 μL lysis solution by pipet. The sample was incubated on ice for 45 min before proceeding with activity analysis.

(b) Total Protein Quantitation

The protein quantitation can be done by any Coomassie dye based assay using the Bradford method; the lit used in this instance was the Coomassie Plus Protein Assay Kit (Pierce, #23236). This was used according to the manufacturer's guidelines (available from Pierce, Doc #0229).

The protein solution of interest was diluted to within the linear range of a standard (albumin) of known protein concentration measured simultaneously. Once the protein concentration was known, an appropriate dilution was calculated to permit reasonable pipetting of 0.1 micrograms of total protein (i.e. within the range of 2 to 20 μL).

(c) Enzyme Activity: Methyl Umbelliferyl butyrate (MUB) Hydrolysis

The volume required for 0.1 μg total protein is brought to 25 μL with 50 mM Tris-HCl pH 9 buffer (buffer type/pH are flexible) in a 96 well plate. Meanwhile a stock of 4 mM MUB (9.8 mg in 10 mL DMSO) is made and apportioned in 400 μL aliquots to be stored at −20° C. The stock is diluted to a working concentration of 200 μM: 400 μL in 7.6 mL 10 mM HEPES buffer pH 7.0. To the 25 μL sample is added 25 μL of the working MUB solution immediately before reading kinetically over a 300 s period on a fluorescent plate reader (SPECTRAMAX GEMINI XS: $?_{ex}$=360 nm; $?_{em}$=465 nm). The working solution can be stored at 4° C. for several days before degradation occurs. It is preferable to thaw an aliquot of DMSO stock and make fresh working solution before each assay.

Hydrolysis of Lovastatin by SEQ ID NO:4 (100 g Scale)

Figure 18A:
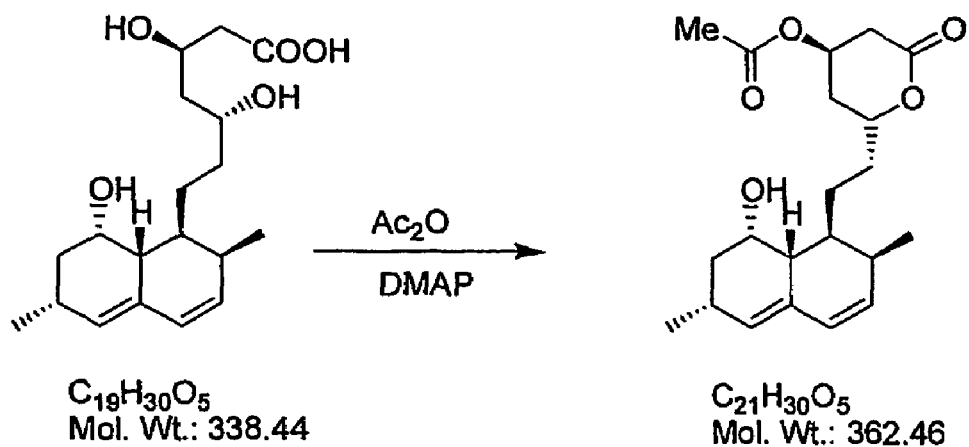
FIG. 18A illustrates an exemplary reaction of the invention comprising a method for the synthesis of 4-acetyl diol lactone, as discussed in detail in Example 3, below.
Figure 18B:
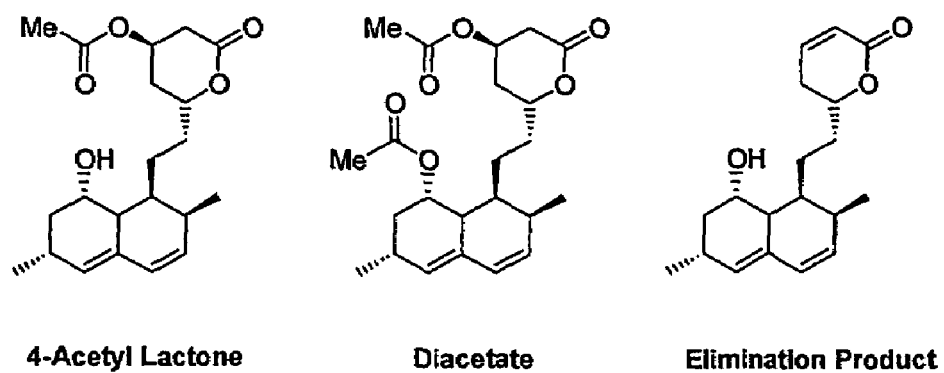
FIG. 18B illustrates the structure of 4-acetyl lactone, the corresponding diacetate structure and the elimination product, as discussed in detail in Example 3, below.
Figure 18C:
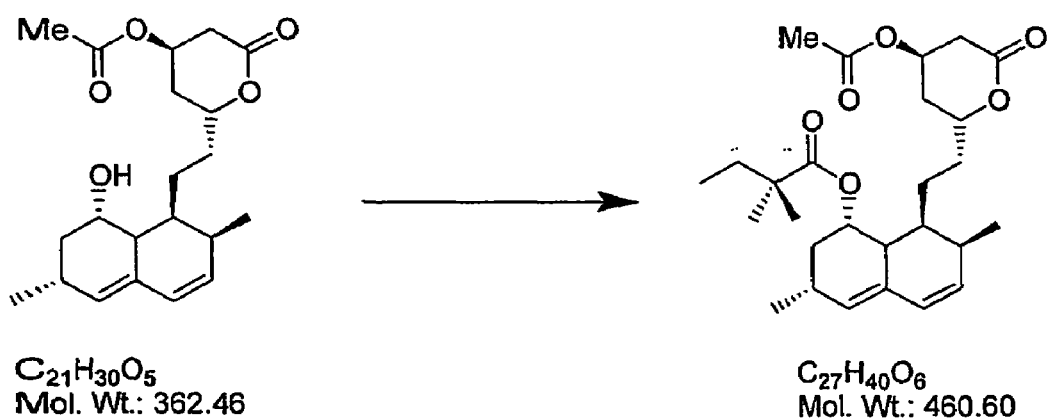
FIG. 18C illustrates an exemplary reaction of the invention comprising synthesis of 4-acetyl-simvastatin, as discussed in detail in Example 4, below.
Figure 18D:
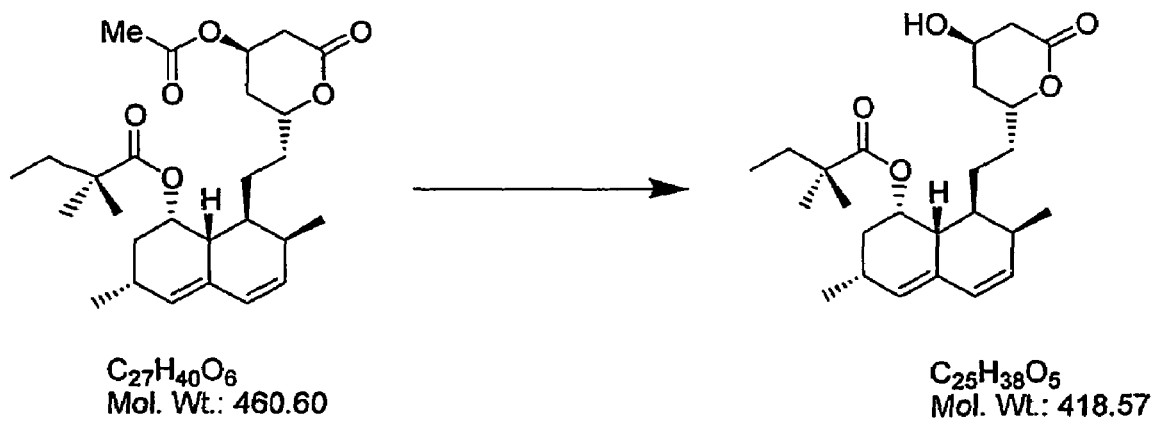
FIG. 18D illustrates an exemplary reaction of the invention comprising the hydrolysis of 4-acetylsimvastatin by an hydrolase, as discussed in detail in Example 4, below.
Figure 18E:
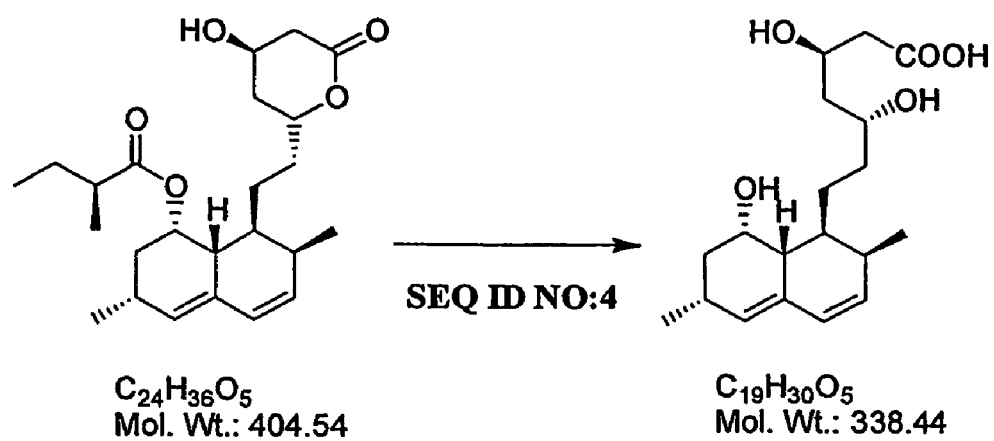
FIG. 18E illustrates an exemplary reaction of the invention comprising the enzymatic hydrolysis of lovastatin to triol acid, as discussed in detail in Example 2, below.

An exemplary reaction of the invention comprising the enzymatic hydrolysis of lovastatin to triol acid is illustrated in FIG. 18E.

1. Lovastatin (10×10 g, 0.25 mol) and water (13×10 mL) were slowly added in alternating portions to a rapidly stirring mixture of MeOH (35 mL, 7% final volume) and 6M NaOH (43 mL, 0.26 mol) in a 1 L 3-neck flask equipped with an overhead paddle stirrer.
2. When a homogeneous mixture was obtained, the mixture was stirred at 35° C. until the pH dropped to 8 (approx. 2 h) whereupon lovastatin was converted to lovastatin acid.
3. Meanwhile lyophilized enzyme (22.64 g) was reconstituted with water (final volume 180 mL). 4M Tris (4 mL) and the reconstituted enzyme solution were added to the lovastatin acid solution. Water (108 mL) was added to bring the volume to 500 mL before initiating pH control.
4. The reaction was controlled using a DASGIP AG-PRO® bioreactor using 30% NH$_4$OH to maintain pH 9.5. The reaction was stirred for 48 h (Note 1, below) and maintained at 35° C., aliquots (10 μL quenched in MeOH, 990 μL) being taken periodically to monitor progress of the reaction by HPLC (Note 2, below).
5. The reaction was terminated by transferring to a 4 L beaker and diluting it with water (1 L). The pH of the mixture was adjusted with 6M HCl. At pH ~4.4 the mixture became very viscous as a white solid precipitated and stirring rate was increased to prevent "gelling" of the mixture. The mixture was adjusted to pH 2.5 using a total of 120 mL 6M HCl and stirred for a further 0.5 h.
6. The resulting slurry was filtered through Whatman #1 filter paper on a 21 cm Buchner funnel, and the damp filter cake washed with water (0.5 L). The damp filter cake was allowed air dry for ~1 h; it was then transferred into 4×600 mL lyophilizer flasks and dried on a lyophilizer for 48 h to provide an off-white powder (98.6 g) (Note 3, below).
7. The filtrate was divided into 3 equal portions which were extracted with a single portion of EtOAc (500 mL). While the 1$^{st}$ extraction separated easily, the 2$^{nd}$ and 3$^{rd}$ portions formed emulsions which did not separate cleanly even after treatment with satd. NaCl (100 mL). The EtOAc extract was washed with saturated ("satd") NaCl (100 mL), dried (Na$_2$SO$_4$) and filtered. The filtrate was stirred under N$_2$ and a solution of MeSO$_3$H (0.2 mL, 3.1 mmol; final concentration ~7 mM) in EtOAc (5 mL) was added dropwise over a period of ~5 minutes after 4.5 h the reaction solution was washed with satd. NaHCO$_3$ (200 mL), water (100 mL) and satd. NaCl (100 mL). The EtOAc layer was concentrated to ~50 mL on a rotary evaporator and diol lactone was precipitated by the slow dropwise addition of hexanes (200 mL). The precipitated solid was collected by filtration and dried (3.36 g, 81.3% purity); a further 0.26 g remained in the mother liquors.
8. The total yield was determined to be 94.9% (see Note 4, below).

Notes

1. HPLC indicated that reactions on a 100 g scale were ~97% complete after 22 h, but were often allowed stir for longer to ensure complete hydrolysis,
2. Samples were analyzed on a Waters 1100 Series HPLC equipped with a DAD, using a ZORBAX SB-Phenyl column (4.6×75 mm)(45% MeCN/0.1% H$_3$PO$_4$ isocratic; 1 ml/min; 30° C.; 238 nm). The order of elution was: Triol acid: 1.4 min, Diol lactone: 1.9 min, Lovastatin Acid: 3.8 min, Lovastatin: 7.3 min.
3. The filter cake at this stage consists of crude triol acid and precipitated protein.
4. The total yield of product was calculated as shown in the Table:
5.

|  |  | g | Purity % | Mmol |  |
|---|---|---|---|---|---|
| Starting material | Lovastatin | 100 | 100 | 247 |  |
| Products | Triol Acid | 98.6 | 77.8# | 225 |  |
|  | Isolated Diol Lactone | 3.36 | 81.5* | 8.5 |  |
|  | Diol lactone in mother liquors | 0.26 |  | 0.8 |  |
| Total |  |  |  | 234.3 | 94.9% |

Assayed by $^1$H NMR versus toluic acid as an internal standard.
*Assayed by HPLC versus a working standard.

Hydrolysis of Lovastatin by SEQ ID NO:4 (150 g Scale)

1. Lovastatin (150 g, 0.37 mol) and water (300 mL) were slowly added in alternating portions to a rapidly stirring mixture of MeOH (52.5 mL) and 50% w/w NaOH (30 mL, 0.57 mol) in a 1 L 3-neck flask equipped with an overhead paddle stirrer. The reaction was stirred at room temperature overnight and the clear mixture then acidified to pH ~7-8 using conc. HCl (~25 mL) (Note 1, below).
2. SEQ ID NO:4 (17 g) was reconstituted in water (50 ml water) and added to the reaction. A further portion of water (300 mL) to bring the volume of the reaction to a total of 750 mL.

3. The reaction was controlled using a DASGIP AG FED-BATCH-pro® bioreactor using 30% $NH_4OH$ to maintain pH 9.5. The reaction was stirred and maintained at 35° C., aliquots (10 μL quenched in MeOH, 990 μL) being taken periodically to monitor progress of the reaction by HPLC (Note 2, below).
4. After 86.3 h, HPLC indicated ~1% lovastatin acid remained and the reaction was terminated. The reaction mixture was transferred to a 4 L beaker, diluted with water (1 L) and vigorously stirred. The mixture was acidified to pH 2.5 with 6M HCl (160 mL) and stirred at room temperature for a further 1.5 h.
5. The slurry was filtered through Whatman #1 filter paper on a 19 cm Buchner funnel and the damp filter cake washed with water (0.5 L). The mixture filtered easily to give a cream-colored filter cake and a golden yellow filtrate. The damp filter cake was allowed air dry for ~1 h; it was then transferred into 4×600 mL lyophilizer flasks and dried on a lyophilizer to provide an off-white powder (154.8 g) (Note 3, below).
6. The filtrate was divided into 3 equal portions which were extracted with a single portion of EtOAc (600 mL). The EtOAc extract was washed with satd. NaCl (100 mL), dried ($Na_2SO_4$), filtered and concentrated to ~250 mL. The filtrate was stirred under $N_2$ and a solution of $MeSO_3H$ (0.2 mL, 3.1 mmol; final concentration ~15 mM) in EtOAc (4 mL) was added dropwise over a period of 5 minutes. After 70 min. the reaction solution was washed with satd. $NaHCO_3$ (200 mL), and satd. NaCl (50 mL). The EtOAc solution was allowed stand overnight, decanted, and concentrated to ~120 mL on a rotary evaporator. The diol lactone was precipitated by the slow dropwise addition of hexanes (200 mL). The precipitated solid was filtered and dried (3.22 g, 92.3% purity); a further 0.47 g remained in the mother liquors.
7. The total yield was determined to be 98.9% (see Note 4, below). The total yield of product was calculated as shown in the following Table:

|  |  | g | Purity % | Mmol |  |
|---|---|---|---|---|---|
| Starting material | Lovastatin | 150 | 100 | 371 |  |
| Products | Triol Acid | 154.8 | 77.8# | 356 |  |
|  | Isolated Diol Lactone | 3.22 | 92.3* | 9.3 |  |
|  | Diol lactone in mother liquors | 0.47 |  | 1.5 |  |
| Total |  |  |  | 366.8 | 98.9% |

Assayed by $^1H$ NMR versus toluic acid as an internal standard
*Assayed by HPLC versus a working standard Example 3

Synthesis of 4-Acetyl Diol Lactone

The invention provides a method for the synthesis of 4-acetyl diol lactone, as illustrated in FIG. 18A.

A. Direct Acetylation of Triol Acid (20 g Scale)
1. Crude triol acid (25.82 g, 59.1 mmol) (Note 1, below) was charged to a dry 500 mL round bottom flask under $N_2$, followed by addition of dry $CH_2Cl_2$ (200 mL). The slurry mixture was stirred magnetically at room temperature under $N_2$. DMAP (1.08 g, 8.8 mmol; 15 mol %) was added followed by slow addition of acetic anhydride (15.8 mL, 2.8 equivs. total) by syringe pump over a period of 8.5 h. A further portion of DMAP (0.36 g, 2.9 mmol) was added at 7.75 h (Note 2, below).
2. The reaction progress was monitored closely by HPLC (Note 3, below).
3. The reaction was quenched after 11 h by addition of water (5 mL) and the mixture stored at −20° C. before workup. The mixture was filtered through a Celite pad to remove insolubles and the Celite pad washed with $CH_2Cl_2$. The filtrate was then washed with 5% HCl (100 mL), $H_2O$ (50 mL), satd. $NaHCO_3$ (3×100 mL), and satd. NaCl (100 mL), dried $Na_2SO_4$), and filtered. The filtrate was then concentrated (~150 mL removed), EtOAc (100 m/L) added and further concentrated to ~60 mL
4. With rapid stirring hexanes (420 mL) was added over a period of 5 min. The precipitated product was collected by filtration, washed with hexanes (100 mL) and dried under vacuum to yield a white solid (17.4 g, 81.2%) (Note 4, 5, below).

Notes
1. The triol acid was determined to be 77.5% pure by $^1H$ NMR assay with toluic acid as an internal standard; the rest of the material is precipitated protein/lyophilization material.
2. The rate of addition of acetic anhydride and DMAP are shown in the following Table:

| The sequence of DMAP and acetic anhydride addition | | | | | |
|---|---|---|---|---|---|
| Time | 0 min | 0-30 min | 3.5-4 hr | 6-6.5 hr | 7.75 hr | 8.5 hr |
| DMAP (g) | 1.083 |  |  |  | 0.36 |  |
| DMAP (mol %) | 15 |  |  |  | 5 |  |
| Acetic anhydride (ml) | 2 | 9.2 | 1.68 | 1.2 |  | 1.68 |
| Acetic anhydride (eq.) | 0.36 | 1.64 | 0.30 | 0.21 |  | 0.30 |

3. Samples were analyzed on a Waters 1100 Series HPLC, using a ZORBAX SB™-Phenyl column (4.6×75 mm) (40% MeCN/0.5% AcOH gradient; 1 ml/min; RT; 238 nm). The gradient and elution order were as follows:

| Time min | MeCN | 0.5% AcOH | Component | Rt |
|---|---|---|---|---|
| 0 | 37.5 | 62.5 | Triol Acid | 1.2 |
| 8 | 37.5 | 62.5 | Diol Lactone | 3.2 |
| 8.1 | 60 | 40 | Elimination Product | 7.5 |
| 12 | 60 | 40 | 4-Acetyl lactone | 8.1 |
| 12.1 | 37.5 | 62.5 | Diacetate | 10.7 |

FIG. 18B illustrates the structure of 4-acetyl lactone, the corresponding diacetate structure and the elimination product.
4. A further 2.20 g (10.3%) of acetyl-lactone remained in the mother liquors, for a total yield of 91.5%.
5. HPLC area % showed: Diol lactone, 0.8%; 4-Acetyllactone, 98.5%; 4,8-Diacetate, 0.2%, Elimination, 0.6%.

B. Direct Acetylation of Triol Acid (37 G Scale)
1. The reaction was carried out as described above using crude triol acid (48.43 g, 111 mmol) (77.45% pure) (Note 1, below) and DMAP (2.30 g, 18.8 mmol; 15 mol %) in anhydrous $CH_2Cl_2$ (375 mL). The reaction slurry was stirred magnetically at room temperature under $N_2$, and acetic anhydride (34.6 mL, 3.3 equivs.) was slowly added by syringe pump (Note 2, below).

2. Into a 1-L dry flask under $N_2$, triol acid (2287-40, 48.43 g, 77.45%) was charged followed by sequential 3. The reaction was quenched after 8 h by addition of water (5 mL), stirred for 10 min, and the mixture stored at −20° C. before workup. The mixture was filtered through a Celite pad to remove insolubles and the Celite pad washed with $CH_2Cl_2$. The filtrate was then washed with 5% HCl (175 mL), $H_2O$ (50 mL), satd. $NaHCO_3$ (2×175 mL, 100 mL), and satd. NaCl (175 mL), dried ($Na_2SO_4$), and filtered. The filtrate was concentrated (300 mL removed), EtOAc (200 mL) added and concentrated to 110 mL 4. With rapid stirring hexanes (450 mL) was added over a period of 5 min. The precipitated product was collected by filtration, washed with hexanes (50 mL) and dried under vacuum to yield a white solid (31.5 g, 78.4%) (Note 3, 4, below).

Notes

1. The triol acid was determined to be 77.5% pure by $^1H$ NMR assay with toluic acid as an internal standard; the rest of the material is precipitated protein/lyophilization material.

2. The rate of addition of acetic anhydride and DMAP are shown in to following Table:

TABLE

| | The sequence of acetic anhydride addition | | | | | | |
|---|---|---|---|---|---|---|---|
| Time | 0–30 min | 0.5–1.5 hr | 1.5–2.5 hr | 3.5–3.7 hr | 4.25 | 5 hr | 5.7 hr |
| Acetic anhydride (mL) | 70.13 | 28.05 | 10.5 | 7 | 14 | 14 | 14 |
| Acetic anhydride (eq.) | 2.0 | 0.8 | 0.3 | 0.2 | 0.4 | 0.4 | 0.4 |

| | The sequence of DMAP and acetic anhydride addition | | | | | |
|---|---|---|---|---|---|---|
| Time | 0 min | 0–30 min | 0.5–2 hr | 2–4 hr | 5.5–7.5 hr | 8 hr |
| DMAP (g) | 2.301 | | | | | |
| DMAP (mol %) | 15 | | | | | |
| Acetic anhydride (ml) | 4.2 | 16.8 | 8.37 | 2.1 | 2.1 | 1.05 |
| Acetic anhydride (eq.) | 0.4 | 1.6 | 0.8 | 0.2 | 0.2 | 0.1 |

3. A further 3.4 g (8.5%) of acetyl-lactone remained in the mother liquors, for a total yield of 86.9%.

4. HPLC area % showed: Diol lactone, 1.4%; 4-Acetyllactone, 97.4%; 4,8-Diacetate, 0.3%, Elimination, 0.6%.

C. Direct Acetylation of Triol Acid (150 G Scale)

1. The reaction was carried out as described above using crude triol acid (154 g) (Note 1, below) and DMAP (6.8 g, 55.7 mmol; 15 mol %) in anhydrous $CH_2Cl_2$ (1 L). The reaction slurry was stirred mechanically under $N_2$, and acetic anhydride was slowly added by syringe pump (Note 2, below). The reaction was held at 15° C. for an initial 1.5 h, then stirred at room temperature.

2. The reaction was quenched after 9.25 h by the addition of water (200 mL), stirred at room temperature for 20 min, then allowed stand overnight.

3. The reaction mixture was filtered through a pad of Celite, which was then washed with $CH_2Cl_2$ (2×250 mL). The combined filtrates were sequentially washed with 5% HCl (500 mL) and $H_2O$ (500 mL), and then concentrated (1.2 L $CH_2Cl_2$ removed). EtOAc (500 mL) was added to the residue and a further 400 mL solvent was removed. The remaining solution was washed with satd. $NaHCO_3$ (500 mL), then stirred with a $NaHCO_3/H_2O$ mixture (500 mL satd. $NaHCO_3$, 500 ml $H_2O$ with a further 167.2 g $NaHCO_3$ powder added in portions)(Note 3, below).

4. The two layers were separated slowly on standing and the organic layer was washed with NaCl (250 mL). The organic layer was dried ($Na_2SO_4$), filtered and concentrated to ~500 mL 5. With rapid stirring, hexanes (3.5 L) were added to the residue over a period of 45 min. The precipitated solid was filtered and dried to yield a white solid (95 g, 70.7%) (Note 4, 5, below).

Notes

1. The crude triol acid was material isolated from the hydrolysis of 150 g lovastatin and carried forward.

2. The rate of addition of acetic anhydride is shown in the Table:

3. Acetic and 2-methylbutyric acid should be removed to prevent their re-introduction in the subsequent acylation reaction.

4. A further 10.1 g (7.5%) of acetyl-lactone remained in the mother liquors, which combined with ~0.16% product lost to the aqueous washes, represented a total yield of 78.4% from lovastatin.

5. HPLC area % showed: Diol lactone, 0.9%; 4-Acetyllactone, 98.7%; 4,8-Diacetate, 0.2%, Elimination, 0.1%.

6. $^1$HNMR (CDCl$_3$) δ 0.90 (d, J=6.94 Hz, 3H), 1.19 (d, J=7.57 Hz, 3H), 1.27-1.41 (m, 1H), 1.45-1.60 (m, 2H), 1.76-1.95 (m, 6H), 2.09 (s, 3H), 2.10-2.13 (m, 1H), 2.14-2.20 (m, 1H), 2.32-2.41 (m, 1H), 2.41-2.50 (m, 1H), 2.67-2.75 (m, 1H), 2.75-2.82 (m, 1H), 4.23 (br s, 1H), 4.54-4.63 (m, 1H), 5.22-5.28 (m, 1H), 5.53-5.58 (m, 1H), 5.77-5.83 (m, 1H), 5.99 (d, J=9.46 Hz, 1H); $^{13}$CNMR (CDCl$_3$) δ 13.98, 21.07, 23.82, 24.19, 27.40, 30.82, 32.95, 33.39, 35.40, 35.83, 36.50, 38.77, 65.34, 65.61, 76.51, 128.51, 130.14, 131.29, 133.60, 168.90, 170.02.

D. Direct Acetylation of Triol Acid (150 G Scale)

a. Crude triol acid (151.21 g from 150 g lovastatin) was charged to a 2-L dry flask followed by addition of $CH_2Cl_2$ (1.0 L). The slurry was agitated by an overhead mechanical stirrer and left overnight at ambient temperature.

b. DMAP (6.8 g, 15 mol % based on 150 g lovastatin) was added in one portion, followed by addition of acetic anhydride (157.6 ml, 4.5 equiv.) over a 20 min period. The reaction was monitored by HPLC.

c. The reaction was quenched after 3.5 h by addition of water (100 ml) and was stirred for an additional 3 h at ambient temperature. The reaction mixture was filtered through a Whatman #1 filter paper and the filter cake was washed with $CH_2Cl_2$ (2×250 ml).

d. The $CH_2Cl_2$ was sequentially washed with 5% HCl (500 ml) and $H_2O$ (500 ml), and then the organic layer was concentrated to 400 ml and diluted with EtOAc (500 ml). This solution was stirred with saturated (satd.) $NaHCO_3$ (500 ml), with additional $NaHCO_3$ (60 g) being added to neutralize acetic acid. The organic layer was washed with satd. NaCl (500 ml), dried ($Na_2SO_4$), and filtered. The filtrate was concentrated to ~100 mL. With stirring, hexanes (500 ml) was added rapidly to the residue. The precipitated solid was filtered and dried to yield a white solid (112.6 g, 83.4%) (Note 1, 2, below).

Notes
1. A further 7.6 g (5.7%) of 4-acetyllactone remained in the mother liquors, representing a total yield of 89.1% from lovastatin.
2. HPLC area % showed: Diol lactone, 0.9%; 4-Acetyllactone, 99.0%; 4,8-Diacetate, 0.45%, Elimination, 0.53%.

E. Direct Acetylation of Triol Acid (150 G Scale)
1. Crude triol acid (158.4 g from 150 g lovastatin) was charged to a 2-L dry flask followed by addition of $CH_2Cl_2$ (625 ml). The slurry was agitated by an overhead mechanical stirrer and left overnight at ambient temperature.
2. DMAP (6.8 g, 15 mol % based on 150 g lovastatin) was added in one portion, followed by addition of acetic anhydride (122.6 ml, 3.5 equiv.) over a 17 min period. The reaction was monitored by HPLC. A further portion of acetic anhydride (35 ml, 1.0 equiv.) was added at 2.5 h followed by addition of $Et_3N$ (25.8 ml, 0.5 equiv.) at 3.5 h (Note 1, below).
3. The reaction was terminated after 6.3 h, and submitted to the same extractive workup as described previously. This time addition of hexanes precipitated the product as large chunks. The solid was redissolved in $CH_2Cl_2$ (300 ml) and EtOAc (300 ml), and concentrated to ~130 mL. Addition of hexanes (650 ml) precipitated the product, which was collected and dried to give a white solid (107.24 g, 79.8%) (Note 2, 3, below).

Notes
1. The reaction stopped at ~60% conversion and $Et_3N$ was added to assist acetylation.
2. A further 10.7 g (8.0%) of 4-acetyllactone remained in the mother liquors, representing a total yield of 87.8% from lovastatin.
3. HPLC area % showed: Diol lactone, 0.6%; 4-Acetyllactone, 97.9%; 4,8-Diacetate, 0.6%, Elimination, 0.9%.

FIG. 18B illustrates the structure of 4-acetyl lactone, the corresponding diacetate structure and the elimination product.

Example 4

Synthesis of 4-Acetylsimvastatin

The following example describes exemplary protocols of the invention, e.g., for the synthesis of 4-acetyl-simvastatin, as illustrated in FIG. 18C.

A. Boron Trifluoride Etherate Catalysis
1. 4-Acetyllactone (110 g, 0.3 mol) was dried overnight under vacuum (0.1 torr) in a 2-neck 2 L flask (Note1).
2. The dried starting material was dissolved in anhydrous $CH_2Cl$ (875 mL) under $N_2$ at room temperature.
3. The catalyst was prepared as follows. In a glove bag under $N_2$, 2,2-dimethylbutyric anhydride (7.1 mL, 30.3 mmol) was added to anhydrous acetonitrile (125 mL), followed by the addition of freshly opened $BF_3.OEt_2$ (3.1 mL, 24.3 mmol; 8 mol %) (Note 2, 3).
4. 2,2-Dimethylbutyric anhydride (78 mL, 0.33 mol; 1.1 equiv.) was added to the solution of 4-acetyllactone and the mixture was heated to 40° C. for 10 minutes (Note 4). The MeCN solution of $BF_3.OEt_2$ was then added via cannula. (Note 5). The reaction was shielded from light, stirred at 40° C. and monitored by HPLC.
5. After 5.5 h the reaction was judged complete and the reaction was cooled to 5° C. in an ice bath. Satd. $NaHCO_3$ (250 mL) was added with vigorous stirring. The aqueous layer was separated and extracted with $CH_2Cl_2$ (200 mL).
6. The organic extracts were combined, dried ($Na_2SO_4$), filtered and concentrated under reduced pressure. MeOH (200 mL) was added to the concentrate (Note 6); removal of more MeOH results in precipitation of 4-acetylsimvastatin. The off-white solid was filtered, washed with cold MeOH (100 mL) and dried under vacuum (92.8 g).
7. The mother liquors were concentrated to about half volume and cooled at −10° C. overnight. A second crop if product (17.2 g) was collected by filtration and dried (Note 7).
8. The HPLC profile is shown in the Table.

| Peak Identity | Retention Time Min | Area % |
|---|---|---|
| 4-Acetyllactone | 1.73 | 0.06 |
| 4,8-Bisacetate | 2.37 | 0.80 |
| Simvastatin | 2.52 | 0.04 |
| Unknown | 3.52 | 0.03 |
| 4-Acetyl Lovastatin | 3.80 | 0.80 |
| 4-Acetyl Simvastatin | 4.59 | 97.78 |
| Anhydrosimvastatin | 5.47 | 0.31 |
| 4-Simvastain-8-Lovastatin | 8.30 | 0.03 |
| Bis-Simvastatin | 9.78 | 0.10 |
| Total Area | | 99.95 |

Notes
1. The starting material should be ground to a powder to facilitate the removal of acetic acid which may be entrained in large chunks. Residual acetic will result in formation of the 4,8-diacetate. Drying at elevated temperature under vacuum may cause decomposition. 4-Acetyllactone turned yellowish when dried at 40° C. under vacuum.
2. Since the reaction is sensitive to the presence of moisture, excess anhydride was initially added to the acetonitrile to scavenge any residual water. Preheating the anhydride and acetyl-lactone scavenges water from the reaction vessel.
3. Freshly opened $BF_3.OEt_2$ should be used for the reaction; reagent that has been opened previously can result in slow, or even, no reaction.
4. The solution must be cooled down during addition of catalyst, otherwise aromatic byproduct is formed.
5. The $CH_2Cl_2$/MeCN ratio was 7:1. Typically the ratio is between 6:1 and 9:1. The reaction is faster in MeCN but the product is formed with a less desirable impurity profile.
6. MeOH should be added before crude product solidifies, otherwise it is difficult to re-dissolve it in MeOH. Dissolving solid product in hot methanol caused decomposition and thus gave lower yield.
7. Total solid product was 110 g (78.7%). The final mother liquors were evaporated to dryness and the residue was assayed versus a working standard and shown to contain a further 9.02 g (6.8%) of product. A further ~2% product remained in the aqueous washes. See FIG. 18C.

B. Synthesis of 4-Acetylsimvastatin

Prepared as described above.

4-Acetyllactone (111.6 g; 91%).

$1^{st}$ crop: 86.2 g $2^{nd}$ crop: 11.6 g

Total: 97.8 g, 75.8%.

Assay:

$^1$H-NMR 99.8% (versus toluic acid as internal standard) HPLC 98.1% (versus working standard of 4-acetylsimvastatin)

The aqueous washes contained ~1.9% and a further ~7% remained in residues for a total yield of 84.7%.

The HPLC profile is shown in the Table.

| Peak Identity | Retention Time Min | Area % |
| --- | --- | --- |
| 4-Acetyllactone | 1.73 | 0.06 |
| 4,8-Bisacetate | 2.37 | 1.42 |
| Simvastatin | 2.52 | ~ |
| Unknown | 3.52 | ~ |
| 4-Acetyl Lovastatin | 3.80 | 0.20 |
| 4-Acetyl Simvastatin | 4.59 | 97.76 |
| Anhydrosimvastatin | 5.47 | 0.50 |
| 4-Simvastain-8-Lovastatin | 8.30 | 0.06 |
| BisSimvastatin | 9.78 | ~ |
| Total Area | | 100 |

C. Synthesis of 4-Acetylsimvastatin

Prepared as described above.

4-Acetyllactone (107 g; 96%).

$1^{st}$ crop: 90.4 g $2^{nd}$ crop: 12.7 g

Total: 97.8 g, 79.3%.

Assay:

$^1$H-NMR 99.2% (versus toluic acid as internal standard) HPLC 96.8% (versus working standard of 4-acetylsimvastatin)

The aqueous washes contained ~1.8% and a further 7% remained in residues for a total yield of 88.1%.

The HPLC profile is shown in the Table.

| Peak Identity | Retention Time Min | Area % |
| --- | --- | --- |
| 4-Acetyllactone | 1.73 | 0.04 |
| 4,8-Bisacetate | 2.37 | 2.20 |
| Simvastatin | 2.52 | ~ |
| Unknown | 3.52 | ~ |
| 4-Acetyl Lovastatin | 3.80 | 0.31 |
| 4-Acetyl Simvastatin | 4.59 | 97.00 |
| Anhydrosimvastatin | 5.47 | 0.35 |
| 4-Simvastain-8-Lovastatin | 8.30 | 0.02 |
| Bis-Simvastatin | 9.78 | 0.08 |
| Total Area | | 100 |

D. Pyridine/DMAP Method 1. 4-Acetyllactone (2.6 g, 7.2 mmol) was dried under vacuum overnight at room temperature, then dissolved in anhydrous pyridine (6.0 mL) with stirring at room temperature under nitrogen. A solution of DMAP (176 mg, 0.2 equiv.) in 1.5 mL anhydrous pyridine was added and the mixture cooled in an ice bath.

2. 2,2-Dimethylbutyryl chloride (7.72 g, 8 equiv.) was added dropwise over 15 minutes using a syringe pump. The mixture was stirred at 0° C. for about one hour, then at room temperature for one hour.

3. The reaction mixture was heated at 40° C. under nitrogen and reaction was monitored by HPLC. After the 4-acetyllactone was consumed (2 days), the pyridine was removed by rotary evaporation. The residue was partitioned between EtOAc (20 mL) and saturated NaCl (20 mL). The organic layer was dried ($Na_2SO_4$), filtered and evaporated to give the crude product (96.5%).

E. Cu(OTf)$_2$/Anhydride Method 1. 10.0 g of 4-Acetyllactone (10.0 g, 27.6 mmol) was dried under vacuum at room temperature for 1 hr, then dissolved in anhydrous $CH_2Cl_2$ (60 mL) and stirred under nitrogen.

2. Meanwhile, a solution of Cu(OTf)$_2$ (0.5 g 5 mol %) and 2,2-dimethylbutyric anhydride (7.15 mL, 30.5 mmol) in anhydrous MeCN (7.0 mL) was prepared and stirred at room temperature inside a sealed flask.

3. The lactone solution was cooled to 15° C. The solution of Cu(OTf)$_2$ and 2,2-dimethyl butyryl anhydride was added dropwise using syringe pump. The reaction was monitored by HPLC and judged complete within 3.0 hours.

4. The reaction was quenched with water (20 mL) and partitioned between CH2Cl2 (100 mL) and satd. NaCl (100 mL). The organic layer was then stirred for 10 minutes with a mixture of 1M malic acid (50 mL) and satd. NaCl (50 mL), then satd. NaCl (100 mL). The organic layer was dried (Na2SO4), filtered and evaporated to yield the crude product (12.8 g>100% yield by weight) (Note 3, 4).

Notes

1. The product distribution by HPLC area % was: 4-acetyl-simvastatin (79.5%), elimination product (12%), bissimvastatin (2%), unidentified impurity (6.5%).

2. 4-Acetylsimvastatin was isolated in 43% after column chromatography. 4-Acyl simvastatin is believed to possess limited stability to SiO$_2$ chromatography.

3. The product distribution by HPLC area % was: 4-acetyl-simvastatin (92.5%), elimination product (2.7%), bissim-vastatin (1.7%), unidentified impurity (3.1%).

4. 4-Acetylsimvastatin was isolated in 61% after column chromatography.

Hydrolysis of 4-Acetylsimvastatin by SEQ ID NO:4

The invention also provides a method comprising the hydrolysis of 4-acetylsimvastatin by an hydrolase, e.g., as illustrated in FIG. 18D.

1. A solution of 4-acetylsimvastatin (3.68 g, 8 mmol) in MeOH (2 mL) was added to a mixture of 4M Tris buffer (0.1 mL) in water (9.9 mL) in a 25 µL 3-neck flask. The slurry was stirred vigorously (both magnetic and overhead stirring) and heated to 50° C.

2. SEQ ID NO:4 (1 g lyophilized material) was dissolved in water (8 mL) and added to the reaction mixture.

3. pH was maintained at 6.75 using a DASGIP FEDBATCH-PRO® system, by addition of 10% $NH_3$ in water, and the reaction temperature maintained at 50° C. using a heated water bath.

4. Once the reaction had reached 75% conversion, toluene (4 µL) was added in order to solubilize the product and remaining starting material.

5. Aliquots (20 µL quenched in 980 µL MeOH) were taken periodically to monitor progress of the reaction by HPLC (Note 1, below).

When judged complete, the reaction mixture was clarified by centrifugation (45000×g, 4° C., 25 min) to give a toluene top layer, an aqueous clarified layer and a compressed solid pellet. The clarified aqueous centrifugate was adjusted to pH 2.5 with HCl. A flocculent precipitate was observed. This mixture was clarified by centrifugation (45000×g, 4° C., 25 min), resulting in another small pellet.

6. Upon examination of each fraction by HPLC, the simvastatin is concentrated in the organic phase and pelleted materials. The pellets were extracted by dichloromethane (100 mL) and the resulting emulsion was separated by centrifugation (45000×g, 4C, 25 min). The $CH_2Cl2$ layers were combined, dried ($Na_2SO_4$) and evaporated to give a yellow oil (3.05 g, 91%) (Note 2, below).

Notes

1. Samples were analyzed on a Waters 1100 Series HPLC, using a Zorbax SB-Phenyl column (4.6×75 mm) (45% MeCN/0.1% $H_3PO_4$ gradient; 1 ml/min; RT; 238 nm). The gradient and elution order were as follows:

| Time min | MeCN | 0.1% $H_3PO_4$ | Component | Rt |
|---|---|---|---|---|
| 0 | 45 | 55 | Simvastatin Acid | 4.7 |
| 10 | 45 | 55 | Simvastatin | 9 |
| 18 | 85 | 15 | Acetyl Simvastatin | 15.2 |
| 19 | 85 | 15 | Eliminated Simvastatin | 15.5 |
| 12.1 | 37.5 | 62.5 | | |

Hydrolysis of 4-Acetylsimvastatin by SEQ ID NO:4

The invention also provides a method comprising the hydrolysis of 4-acetylsimvastatin by an esterase, e.g., the esterase of SEQ ID NO:4, see FIG. 18D.

1. A mixture of 4-acetylsimvastatin (96.6 g, 0.21 mol) and SEQ ID NO:4 (20 g) was suspended in 10% MeOH (1 L) in a 2-L round bottom flask equipped with a magnetic stir-bar and an overhead stirrer. The mixture was stirred vigorously and maintained at 60° C. in a heated water bath.

2. pH was maintained at 7.5 using a DASGIP FEDBATCH-pro® system, by addition of 10% $NH_3$ in water. The reaction was monitored by HPLC.

3. After 24 h, the reaction mixture was transferred into 4×250 mL centrifuge bottles and centrifuged at 10,000 rpm at 4° C. for 15 min. The supernatant was decanted and discarded. The pellets were resuspended in water (4×250 mL) and centrifuged as before. Again the supernatant was decanted and discarded.

4. The centrifuge pellets were transferred to a sintered glass funnel and excess water removed. The centrifuge bottles were rinsed with acetone (2×150 mL) which was transferred to the funnel. Celite (10 g) was added to the funnel, the mixture triturated and then sucked dry.

5. The residue on the funnel was washed with $CH_2Cl_2$ (5×200 ml), triturating after each portion and adding further Celite as necessary.

6. The combined washings were washed with satd. NaCl (100 ml) and the aqueous layer discarded. The organic layer was dried ($Na_2SO_4$), filtered, and the solvent exchanged for toluene (200 ml).

7. Hexanes (600 ml) was added with stirring to the toluene solution; precipitation started after ~300 ml had been added. The precipitated product was filtered and dried to yield a white solid (69.9 g, 79.7%)

8. The mother liquors were cooled to −20° C. overnight and a second crop of simvastatin was collected (3.5 g, 4.0%).

Example 5

Exemplary Synthetic Schemes of the Invention

The following example describes exemplary protocols of the invention, e.g., schemes for synthesizing simvastatin from lovastatin:

Step 1: Lovastatin Hydrolysis

Figure 15A:
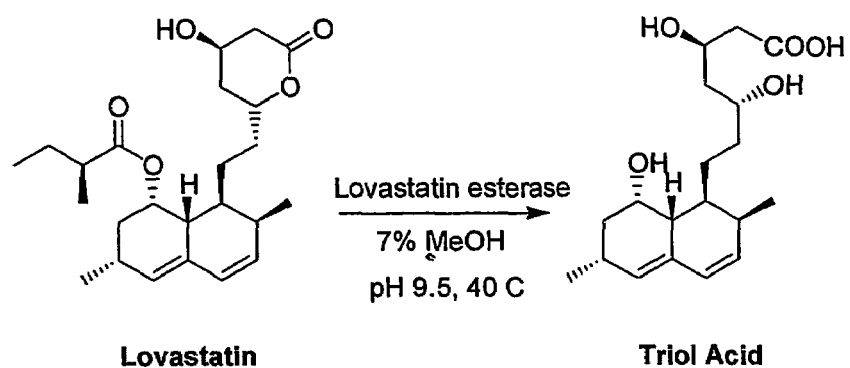
FIG. 15A illustrates an exemplary reaction of the invention comprising hydrolysis of lovastatin to a triol acid using an esterase, as discussed in detail in Examples 5 and 7, below.
Figure 15B:
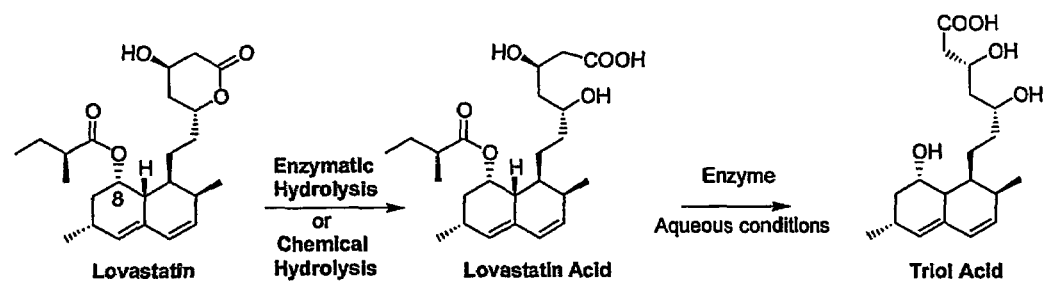

The invention also provided methods comprising the generation of triol acid from lovastatin, as illustrated in FIG. 15A.

Having identified a novel lovastatin esterase (having a sequenced as set forth in SEQ ID NO:4 and subsequent subclones), efforts focused upon producing a scaleable enzymatic hydrolysis process. Among the required parameters for the proposed simvastatin process was that the enzymatic reaction be run at high substrate loading. Initial screening and confirmatory reactions were carried out using lovastatin acid, because of its high aqueous solubility. Reactions using lovastatin were much slower because of the lower solubility of lovastatin in water, especially at lower pH's (7-8) and high substrate loading.

Lack of solubility was overcome by first chemically opening the lactone ring in situ. Thus a suspension of lovastatin in MeOH/water (final reaction concentration 7-10% MeOH) was treated with 1 equivalent of NaOH and the mixture stirred for a couple of hours until the lovastatin had been converted to the more soluble lovastatin acid. When ring-opening was complete, the pH of the reaction mixture was adjusted to pH 9.5 before addition of the enzyme, although adjustment was not necessary in many cases as the pH fell to an acceptable value as the ring opening proceeded.

The enzymatic reaction was initiated by addition of a solution of the reconstituted enzyme. The mixture was then stirred at 35-40° C., with the pH being held constant at pH 9.5 by automatic addition of 10-30% $NH_4OH$. Under these conditions >98% conversion of lovastatin to triol acid was generally obtained in 48 h. The reaction slows down considerably towards completion. The results for a series of large scale hydrolyses are gathered in Table 1.

TABLE 1

Hydrolysis of Lovastatin

| Run | Substrate g | Enzyme Lot | g | Time h | Triol Acid % | Lovastatin Acid % |
|---|---|---|---|---|---|---|
| 1 | 100 | SEQ ID NO: 4 | 22 | 48 | 98.7 | 0.5 |
| 2 | 150 | SEQ ID NO: 4-1 | 25 | 86 | 98.8 | 1.2 |
| 3 | 150 | SEQ ID NO: 4-1 | 25 | 108 | 99.1 | 0.9 |
| 4 | 10 | SEQ ID NO: 4-1 | 2.2 | 41 | 98.7 | 1.0 |
| 5 | 150 | SEQ ID NO: 4-2 | 30 | 46 | 99.1 | 0.9 |
|  |  |  |  | 52 | 99.5 | 0.5 |
| 6 | 150 | SEQ ID NO: 4-2 | 30 | 48.5 | 98.6 | 1.4 |
|  |  |  |  | 64 | 99.5 | 0.5 |

Runs 2 and 3 showed abnormally long reaction times. In these two cases, the lovastatin lactone opening was carried out using a large excess of NaOH and required addition of HCl to return the pH to a suitable range for the enzymatic reaction. It had previously been observed that high salt concentrations had a deleterious effect on the enzymatic hydrolysis.

Furthermore, due to limited availability at the time, the initial enzyme charge (11% w/w) was less than used previously; further portions of enzyme were added to bring the final enzyme charge to 17% w/w.

The reaction was terminated by diluting the reaction mixture with water and then acidifying the mixture to pH~2. Under these conditions the triol acid, denatured protein and other media/cell components precipitated from solution.

For initial small scale, dilute reactions, this mixture was subjected to continuous liquid extraction with refluxing iPrOAc. Under these conditions the lactonization of triol acid occurred and the diol lactone could be easily obtained by precipitation from the concentrated iPrOAc extract.

For larger scale reactions the precipitated triol acid/denatured protein mixture was isolated by filtration and, while still damp, the filter cake was suspended in iPrOAc and subjected to azeotropic distillation to effect lactonization. The insoluble, denatured protein/cell components were removed by filtration and the diol lactone isolated by concentration and precipitation. This procedure worked well on a 10-30 g scale to generate the diol lactone without purification of the triol acid. However as the scale of the reaction increased (50-100 g), the azeoptropic distillation required longer reflux periods in more concentrated solutions to effect lactonization. The yield of diol lactone isolated under these conditions was diminished, and the product was contaminated with increasing quantities of yellow oil, presumably caused by polymerization of the triol acid or diol lactone.

At >100 g scale in the laboratory, the most convenient workup was to dilute and acidify the enzymatic reaction mixture. The insoluble materials were collected by filtration and this damp filter cake was dried; initially lyophilization was used for drying, but for additional runs the filter cake has been dried in a vacuum oven at 30-40° C. Assaying the crude product ($^1$H NMR in the presence of an internal standard) indicated that it contained ~78% triol acid, the rest of the material being denatured protein, cell and media components.

After filtration the filtrate could be extracted with EtOAc to recover a further ~2% of product This material could be isolated, either as the triol acid or lactonized (7 mM MeSO$_3$H) to the diol lactone, and added to the next step.

Step 2: Acetylation

The invention also provides a method comprising generating 4-acetyllactone from triol acid, as illustrated in FIG. 9A.

Subsequent changes to the process, namely (i) the direct acylation from triol acid to 4-acetyllactone and (ii) improved conditions for the introduction of the dimethylbutyrate side-chain improved the process.

The crude product from the lovastatin hydrolysis step contains triol acid and denatured protein and cell/media components. This crude material was suspended in CH$_2$Cl$_2$ (10-15% w/v) and treated with acetic anhydride, three equivalents (i.e., 3 equivs.), in the presence of DMAP (0.15 equivs.). Studies have shown that acetylation of the 8-position of 4-acetyllactone is slow and can be reasonably controlled. The reaction is monitored by HPLC and is typically terminated when <2% diol lactone remains; at this point <2% of diacetate is formed. Some elimination product may be formed, especially if the reaction is stirred for excessively long periods.

After completion the reaction is quenched by the addition of water, and the insoluble materials are removed by filtering through a Celite pad. This pad is washed with CH$_2$Cl$_2$ and the combined filtrates are washed with dilute acid (to remove DMAP) and with satd. NaHCO$_3$ to remove acetic acid. On large scale it was found more convenient after the acid wash, to carry out a solvent exchange for EtOAc to facilitate the subsequent washing with base.

After base extraction, the solution is dried, filtered and concentrated. Addition of hexanes then leads to the precipitation of 4-acetyllactone as a white solid. The yields and product profiles for several larger runs are collected in Table 2.

TABLE 2

Direct acetylation of triol acid to 4-acetyllactone

| Run | Triol Acid g | Time h | Yield % | Diol Lactone % | 4-Ac-Lactone % | DiOAc % | Elimination % |
|---|---|---|---|---|---|---|---|
| 2516-51 | 1 | 26 | 11 | 81.2 (91.5)[1] | 0.8 | 98.5 | 0.2 | 0.6 |
| 2516-55 | 2 | 48 | 8 | 78.4 (86.9)[1] | 1.4 | 97.4 | 0.3 | 0.6 |
| 2516-60 | 3 | 154 | 9.25 | 70.7 (78.2)[2] | 0.9 | 98.7 | 0.17 | 0.11 |
| 2516-64 | 4 | 147 | 9.2 | 78.1 (84.1)[2] | 0.6 | 97.6 | 0.5 | 0.5[3] |
| 2516-84 | 5 | 151 | 3.5 | 83.8 (89.4)[1] | 0 | 99.0 | 0.5 | 0.5 |
| 2516-87 | 6 | 158 | 6.3 | 79.8 (87.8)[1] | 0.6 | 97.9 | 0.6 | 0.9 |

[1] Values in parentheses include unrecovered product in the mother liquors
[2] Values in parentheses include a recovered second crop of product
[3] Also contains 0.24% 4-AcLovastatin, and 0.5% of an unknown impurity at 4.0 min Step 3: Acylation The invention also provides methods comprising generating 4-acetylsimvastatin from 4-acetyllactone, as illustrated in FIG. 9B (using, e.g., 2,2, dimethylbutyric anhydride).

Catalyst identification

Reported conditions for the introduction of the simvastatin side-chain were not suitable for process scale-up. The reaction (i) is run in neat pyridine, (ii) uses up to 8 equivalents of 2,2-dimethylbutyryl chloride, and (iii) requires several days at elevated temperature. In our hands the product isolated from such reaction conditions was obtained in low yield and was of poor quality (elimination of the 2-acetoxy group was a major problem). Alternative solvents/bases did not improve the reaction.

Considerable improvement was achieved by switching to a Lewis acid-catalyzed reaction using dimethylbutyric anhydride as the acylating agent. Bismuth triflate (Bi(OTf)$_3$) was examined (Bi(OTf)$_3$ has been reported as an effective catalyst for the pivaloylation of alcohols). The reaction was much cleaner than the pyridine route. However, Bi(OTf)$_3$ is not commercially available and bismuth residues were difficult to remove from the product. Copper triflate (Cu(OTf)$_2$), which is commercially available, also worked well, giving good yields of product with only 10% load of catalyst and 1.05 equivalents of dimethylbutyric anhydride at room temperature. In this case removal of copper salts was a problem.

At this time, we had already surveyed a series of Lewis acids for their ability to catalyze the regioselective acylation of diol lactone at the 8-position to give simvastatin directly. Of the >20 Lewis acids surveyed, activity was seen with the triflate salts of bismuth, copper, scandium, indium, aluminum, and with TMSOTf and BF$_3$.OEt$_2$. The triflate salts of Li, Mg, Zn, La, Pr, Sm, Yb were not active under the same conditions, nor were pyridinium or imidazolium triflate, nor the acetate salts of Bi, In, or Sr.

BF₃.OEt₂ was an attractive catalyst for the acylation of 4-acetyllactone since it is cheaply available. Various other adducts of boron trifluoride were tested as acylation catalysts. Neither the THF adduct nor the dimethylamine adduct of BF₃ were suitable Lewis catalysts. Activity was seen with other commercially available BF₃.solvates but, since they offered no advantage over BF₃.OEt₂, further optimization was carried out with the etherate.

Optimization of Conditions

Figure 1:
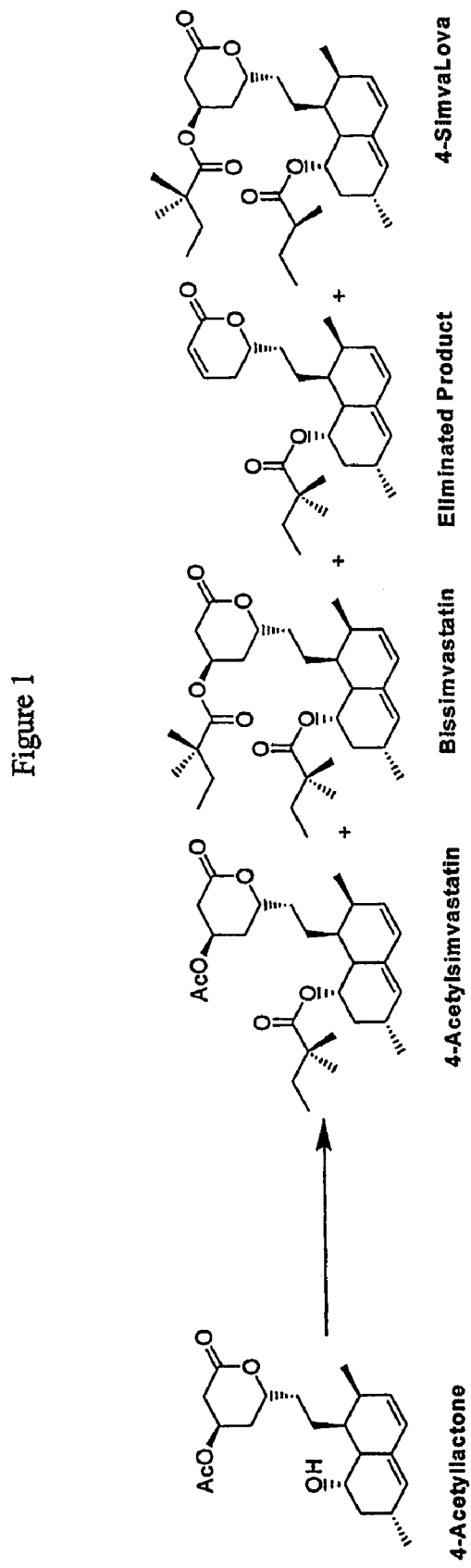
FIG. 1 is an illustration of exemplary protocols for triflate and $BF_3$ etherate-catalyzed acylation of 4-acetyllactone, as discussed in detail in Example 5, below.

A range of solvents and conditions were tested for both the triflate and BF₃ etherate-catalyzed acylation of 4-acetyllactone, as illustrated in FIG. 1. The best results were obtained in CH₂Cl₂, MeCN, dichloroethane, or mixtures thereof. The results of several BF₃.OEt₂ catalyzed acylations are collected Table 3, illustrated in FIG. 2.

The reaction was faster with a higher ratio of MeCN present but gave a poorer yield (Cf. runs 1, 3). Better results were observed using fresh BF₃.OEt₂ (Cf. runs 1, 2, 6); previously opened bottles (run 2) and prealiquoted stock solutions (run 6) of BF₃.OEt₂ in MeCN gave poorer results. A minimum catalyst concentration was required; 4 mol % catalyst gave incomplete reaction (run 4).

In all reactions, a range of minor impurities could be seen. Some of these, e.g., the diacetate or 4-acetyllovastatin were present in the starting 4-acetyllactone, or were the direct result of impurities in the starting material, e.g., bissimvastatin which is formed from diol lactone. The levels of most of these impurities could be significantly reduced by precipitating the crude product from aqueous MeOH; Table 4 shows the impurity profile for the product of a 12 g acylation reaction, before and after precipitation, as illustrated in FIG. 3. The yields for a series of reactions at the 20-100 g scale are shown in Table 5; isolated yields as well as the location and estimated amounts of the remaining product are indicated.

TABLE 5

Acylation of 4-acetyllactone: Results

| Run | 4-Ac-Lactone[1] g | Time h | Isolated solid[2] g % | Aqueous[3] g % | Residue[4] g % | Total Yield % |
|---|---|---|---|---|---|---|
| 1 | 21.0 | 3 | 21.0 | ~0.5 | 1.5 | ~90.1 |
|   |      |   | 82   | ~2   | 6.1 |       |
| 2 | 31.5 | 3.5 | 30.8 | ~0.7 | 3.5 | ~92.4 |
|   |      |     | 81.5 | ~1.9 | 9.0 |       |
| 3 | 94.0 | 5 | 93.7 | ~2.3 | 11.2 | ~93.3 |
|   |      |   | 81.4 | ~2.0 | 9.9  |       |
| 4 | 112  |   | 97.8 |      |      | ~84.7 |
|   |      |   | 75.8 | ~2   | ~7   |       |
| 5 | 107  |   | 97.8 |      |      | ~88.1 |
|   |      |   | 79.3 | ~2   | ~7   |       |

[1]Conditions: 4-Acetyllactone 10% w/v; BF₃•OEt₂ 8 mol %; 40° C.; 5-9:1 DCM/MeCN
[2]Following precipitation from MeOH/water or MeOH alone
[3]Material in aqueous washes determined by HPLC assay against a working standard
[4]Remaining in mother liquors after concentration; determined by NMR assay against an internal standard Step 4: Enzymatic Deacetylation The invention also provides methods comprising the conversion of acetylsimvastatin to simvastatin, as illustrated in FIG. 9C.

There are two significant hurdles to overcome in the enzymatic deacetylation of 4-acetyl simvastatin:

(i) the insolubility of both the starting material, 4-acetylsimvastatin, and the product, simvastatin, in aqueous solution, (ii) the sensitivity of the 4-acetyl group, which rapidly undergoes elimination at pH>7.

Unlike the lovastatin hydrolysis reaction, the hydrolysis 4-acetyl simvastatin must be run close to pH 7 where increasing the solubility by opening the lactone ring is not possible.

For the hydrolysis of 4-acetylsimvastatin, SEQ ID NO:4, encoded, e.g., by SEQ ID NO:3, the esterase gene cloned in *E. coli*, 10 mM substrate was hydrolyzed rapidly. Subsequent reactions at 200 mM indicated 91-93% conversion in 46 h; the 4-chloroacetyl derivative showed comparable conversion, while the 4-formyl derivative reacted completely in 24 h. While the 4-formyl derivative was an attractive substrate in terms of its solubility and reactivity, we were unable to develop an efficient synthesis of it. Similar results were obtained for all three derivatives when the reaction was carried out in a MTBE biphasic system.

A number of reaction parameters were examined using SEQ ID NO:4. Starting the hydrolysis at pH 8 resulted in the formation of an unacceptable level of elimination product, while poor results were obtained using 5% dioxane as cosolvent or surfactants (0.1% Triton X-100 or Tween-20). While the rate of the reaction was considerably enhanced at 50° C., all reactions generally stopped at ~90% conversion as the reaction mixture became increasingly viscous.

For biphasic reactions at 50 mM substrate the use of MTBE, dibutyl ether or toluene as cosolvent worked well under these conditions, whereas the use of chlorinated solvents resulted in negligible activity.

It was possible to run the reaction at up to 300-400 mM if the hydrolysis was started at 50° C., pH 7 in the presence of 10% MeOH. After 5-6 h, as the reaction became very viscous, an equal volume of toluene was added to the reaction. Under these conditions almost complete conversion was observed with minimal elimination.

Up to this stage all enzymatic reactions had been run using 4-acetyl-simvastatin that had been prepared from simvastatin. Preparing the substrate from the readily available simvastatin allowed us to carry out initial studies of the final enzymatic hydrolysis while the other steps of the synthesis were being developed.

Unfortunately, substrate which was initially prepared from lovastatin was variable in quality, depending on the Lewis acid catalyst used and the extent of purification. These materials resulted in a significant amount of variability in the results, and the initial good results for the enzymatic deacetylation were not reproducible.

Figure 20:
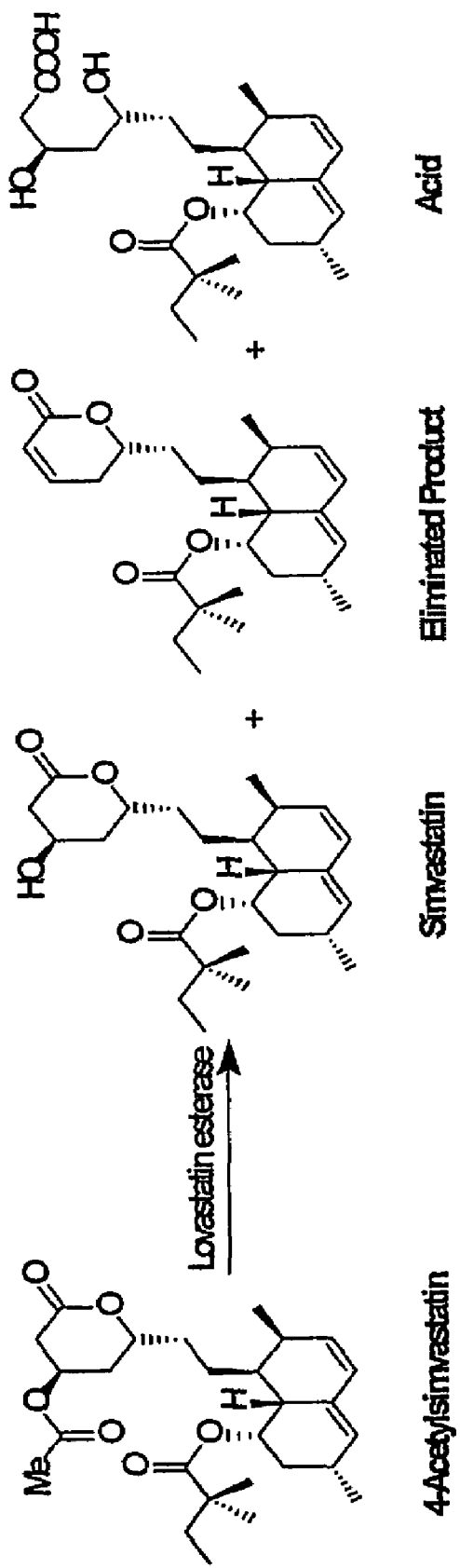
FIG. 20 illustrates the hydrolysis of 4-acetylsimvastatin to simvastatin, with the corresponding eliminated product and acid, as discussed in detail in Example 5, below.

Results for one set of reactions for the hydrolysis of 4-acetylsimvastatin to simvastatin are collated in Table 6. In this case all reactions have been run using 10% MeOH and the same batch of enzyme (SEQ ID NO:4-2). FIG. 20 illustrates the hydrolysis of 4-acetylsimvastatin to simvastatin, with the corresponding eliminated product and acid.

TABLE 6

Enzymatic Hydrolysis of 4-Acetylsimvastatin

| Run | Batch | Scale g | mM | Temp °C. | pH | Time h | Acid % | Simva % | 4-Acsim % | Elimin % |
|---|---|---|---|---|---|---|---|---|---|---|
| 1 | 2719-93 | 10 | 200 | 50 | 7.0 | 79 | 1.3 | 90.8 | 6.6 | 1.3 |
| 2 | Synthetic | 10 | 200 | 50 | 7.0 | 43 | 1.5 | 93.9 | 1.1 | 3.5 |
| 3 | Synthetic | 20 | 200 | 50 | 7.0 | 79 | 3.8 | 92.7 | 0 | 3.5 |
| 4 | 2719-95 | 20 | 200 | 50 | 7.0 | 45 | 3.0 | 95.5 | 0.5 | 1.0 |
| 5 | " | 5 | 100 | 50 | 7.0 | 45 | 1.4 | 95.3 | 2.7 | 0.6 |
| 6 | " | 5 | 200 | 50 | 7.5 | 33 | 2.5 | 94.8 | 1.6 | 1.1 |
| 7* | " | 5 | 200 | 50 | 7.0 | 45 | 1.5 | 96.1 | 1.4 | 0.9 |
| 8 | " | 5 | 200 | 45 | 7.0 | 45 | 1.3 | 94.2 | 3.6 | 0.9 |
| 9 | " | 5 | 200 | 40 | 7.0 | 22 |  | 42.7 | 56.7 | 0.6 |
| 10 | " | 10 | 200 | 50 | 7.5 | 18 | 1.3 | 93.2 | 4.5 | 1.0 |
| 11 | " | 5 | 200 | 50 | 8.0 | 18 | 2.9 | 93.5 | 2.1 | 1.5 |
| 12 | " | 5 | 200 | 50 | 7.0 | 18 | 0.9 | 84.1 | 14.2 | 0.9 |

*Enzyme added in 4 portions over 24 h

The first two runs in Table 6 compare the hydrolysis of 4-acetylsimvastatin prepared from lovastatin (run1) with that prepared from simvastatin (run 2). At 200 mM, substrate 2719-93 was clearly inferior, requiring 79 h to reach 92% conversion compared to 43 h for the substrate prepared from simvastatin (run 2). On the other hand substrate 2719-95 (run 4) reached 98% conversion in 45 h, compared to 79 h for the synthetic substrate (run 3) at 200 mM. Substrate 2719-93 had shown low purity, being contaminated with residual 2,2-dimethylbutyric acid and giving consistently poor results. While no inhibitory effect had been observed in the presence of 2,2-dimethylbutyric acid at low conversions, it is possible that it might be responsible for a marked slowing down of the rate of hydrolysis at high conversions.

4-Acetylsimvastatin prepared from simvastatin performed poorly on a 20 g scale (cf., runs 2, 3). While this result may reflect problems in stirring the larger scale reaction, this material reacted more slowly than substrate 2719-95 (run 4). While the eliminated product could possibly act as an irreversible inhibitor due to its potential to act as a Michael acceptor, no inhibitory effect was observed at low conversion when the reaction was run in the presence of the elimination product.

Results using substrate 2719-95 gave consistent results. The reaction gave similar results at 100 and 200 mM (runs 5, 6) which may reflect the constant, low solubility of the starting material in the reaction mixture. At pH 7, higher conversions were observed at 50° C. than at 40-45° C. (run 7-9). Runs 10-12 indicate that the reaction is somewhat pH dependent, with higher conversions (94-96%) being observed at pH 7.5-8.0 compared to pH 7 (85%). Again this may reflect a higher solubility of the substrate under more basic conditions. However, the increase in conversion was accompanied by a slight increase in the level of simvastatin acid at higher pH. While higher pH increased the rate of the reaction it did not significantly increase the amount of elimination up to pH 8. Indeed all reactions showed <2 area % eliminated product, with the exception of runs 2, 3; the starting 4-acetylsimvastatin for runs 2, 3 was already contaminated with ~3.5% elimination product.

Further studies of the enzymatic reaction concentrated on attempts to shorten the reaction time by varying the reaction temperature and pH. The data in Table 7 indicate that reaction times can be shortened by operating at higher temperature, but the data may be complicated by the effects of stirring different scale reactions (cf. Runs 13-16). However, increasing temperature and/or acid results in an increase in the amount of simvastatin acid formed, but in general did not result in a significant increase in elimination (the highest amount was observed at 60° C. and pH 8 (Run 20)). Under the present lab scale workup, this simvastatin acid is lost in the aqueous stream. However workup conditions involving an acidic workup might relactonization to simvastatin with capture of some of this material.

TABLE 7

Hydrolysis of 4-Acetylsimvastatin: Effect of Temperature and pH

| Run | Batch | Scale g | Temp °C. | pH | Time | Acid % | Simva % | 4-Acsimv % | Elim % |
|---|---|---|---|---|---|---|---|---|---|
| 13 | 2719-95 | 5 | 55 | 7.5 | 18 | 2.3 | 95.0 | 1.6 | 1.1 |
| 14** | 2958-8 | 10 | 55 | 7.5 | 36 | 3.5 | 95.0 | 0.7 | 0.9 |
| 15** | 2958-8 | 10 | 55 | 7.5 | 36 | 3.7 | 93.5 | 1.8 | 0.9 |
| 16 | 4-38-1 | 40 | 55 | 7.5 | 41 | 5.5 | 91.3 | 1.7 | 1.4 |
| 17 | 4-38-1 | 20 | 55 | 7.5 | 41 | 4.9 | 92.9 | 0.8 | 1.4 |
| 18 | 4-38-1 | 5 | 60 | 7.5 | 41 | 5.2 | 93.0 | 0.6 | 1.2 |
| 19 | 4-38-1 | 5 | 55 | 8.0 | 15.5 | 2.9 | 94.4 | 1.3 | 1.3 |
| 20 | 4-38-1 | 5 | 60 | 8.0 | 15.5 | 9.0 | 81.3 | 6.6 | 3.1 |
| 21 | 2958-12 | 96.6 | 60 | 7.5 | 1 | 0.3 | 39.7 | 59.5 | 0.6 |
|  |  |  |  |  | 18 | 3.2 | 92.1 | 3.1 | 1.4 |
|  |  |  |  |  | 24 | 5.1 | 91.4 | 1.7 | 1.8 |

In Table 7: all reactions run at 200 mM
*batch-wise addition of enzyme
**duplicates The latest experiment (Run 21) at 100 g scale was run at 60° C. and pH 7.5, with a combination of magnetic and overhead stirring to efficiently mix the contents of the reaction flask. Under these conditions ~98% conversion of starting material was observed after 24 h.

Workup of the enzyme-catalyzed hydrolysis presented a challenge at the lab-bench scale. Filtration of the reaction mixture was very slow, presumably due to fouling of the filter by precipitated protein. Instead, centrifugation was a convenient method to separate the precipitated simvastatin from the bulk of the supernatant aqueous solution; most of the simvastatin acid is lost at this stage. The wet centrifuge pellet was then digested twice with $CH_2Cl_2$, the supernatant being decanted each time. The combined organic supernatant, which contained the bulk of the simvastatin product, was dried, filtered and the solvent exchanged for toluene. Addition of hexanes to this toluene solution and cooling resulted in the precipitation of simvastatin.

Even after digestion with $CH_2Cl_2$ the centrifuge pellet still contained a significant quantity of product; presumably the $CH_2Cl_2$ cannot efficiently access the wet centrifuge pellet and extract out the entrained product.

In a one exemplary modification (Run 4; Table 8), the centrifuge pellet was treated with acetone and Celite and then filtered. The Celite pad could then be easily extracted with $CH_2Cl_2$. The combined aqueous acetone and $CH_2Cl_2$ washings were then dried and the solvent exchanged for toluene. Addition of hexanes resulted in the immediate precipitation of simvastatin which was filtered and dried. Cooling the mother liquor to –20° C. resulted in the isolation of a second crop; the yield data in Table 8 (FIG. 4) are for combined $1^{st}$ and $2^{nd}$ crops.

The invention provides novel practical routes for generating simvastatin starting from lovastatin. In alternative aspects of the invention, salient features of the route comprise:
  i. The use of a novel lovastatin esterase which can remove the 2-methylbutyrate side-chain with 99% conversion in approximately 48 h at a substrate loading of 0.5M at 35° C. and pH 9.5. The possibility of significantly increasing the rate of reaction by increasing the reaction temperature exists. The demonstration of a 1-pot lactonization/ acetylation which converts crude triol acid to 4-acetyl- lactone. Overall yields of 80% from lovastatin have been routinely achieved with a further 8-10% of potential product remaining in mother liquors.
  ii. The discovery of novel and mild conditions for the introduction of the simvastatin side-chain using $BF_3.OEt_2$ catalyzed acylation with dimethylbutyric anhydride. The reaction has been run consistently at ~100 g scale at 10% substrate loading, providing 4-ace- tylsimvastatin in 80% yield. A further 8-10% of potential product remains in the reaction residues.
  iii. The final step uses the same lovastatin esterase as used in the first step to remove a sensitive acetyl group to yield simvastatin. This reaction has been run on a 20-100 g scale at 9% w/v substrate loading showing 98% in 24-48 h.

Example 6

Exemplary Processes of the Invention

The following example describes exemplary protocols of the invention, including schemes for synthesizing simvastatin from lovastatin.

The invention provides a method for making lovastatin acid from lovastatin, and triol acid from lovastatin acid, as illustrated in FIG. 16A, or "Step 1." In this aspect, the protocol effects complete (>99%) removal of the methylbutyrate sidechain. This can be important because of the difficulty in separating lovastatin and simvastatin, and the low allowable levels of lovastatin in simvastatin API (some procedures for the hydrolysis of lovastatin have required the use of high temperatures and long reaction times for a complete (>99%) reaction).

Lovastatin is hydrolyzed under mild conditions using a hydrolase enzyme (e.g., as described herein), resulting in hydrolysis of the lactone ring and complete removal of the side-chain in the 8-position. Three exemplary hydrolase enzymes that can be used in this enzymatic hydrolysis of the methylbutyrate sidechain are the esterase enzymes: SEQ ID NO:4 (encoded by, e.g., SEQ ID NO:3), SEQ ID NO:6 (encoded by, e.g., SEQ ID NO:5), and SEQ ID NO:2 (encoded by, e.g., SEQ ID NO:1). SEQ ID NO:4 (encoded by, e.g., SEQ ID NO:3). Each has been subcloned and expressed in different hosts and fermented at different scales, including at 200 liter (L) scale.

Lovastatin shows poor solubility under the aqueous conditions necessary for enzymatic activity. Alternatively, in one aspect, a suspension of lovastatin in water is raised to pH>12 to effect a rapid hydrolysis of the lactone ring resulting in the in-situ formation of the more soluble lovastatin acid salt. In practice, a suspension of lovastatin in water/MeOH is treated with a solution of 1 mole equivalent of NaOH in water and stirred until dissolution is complete. The pH of the reaction mixture is then readjusted to a range suitable for the enzymatic reaction and the enzyme is added.

In alternative aspects, enzymatic hydrolysis conditions can be applied to mixtures of lovastatin and/or lovastatin acid extracted directly from fermentation broth, or the enzyme may be added to the fermentation broth and the triol acid isolated directly.

After hydrolysis, the reaction mixture is carefully acidified, and the triol acid is isolated by extraction and/or filtration. In one aspect, it is used directly in the next step, or it is isolated as a solid after a suitable crystallization/precipitation step.

The invention provides a method for making diol lactone from triol acid, as illustrated in FIG. 16B, or "Step 2." In one aspect, the triol acid is re-lactonized by heating in a suitable solvent, driving the equilibrium to the lactone form by removal of water by conventional means. Alternatively, in one aspect the triol acid is re-lactonized by stirring in the presence of a suitable acid. This also will effect closure of the lactone ring. The diol lactone may be purified at this stage by crystallization/precipitation from suitable solvent(s).

The invention provides a method for making acyl lactone from diol lactone, as illustrated in FIG. 16C, or "Step 3." In one aspect, regioselective acylation of the hydroxyl group in the 4'-position is carried out enzymatically using an enzyme with the desired activity and selectivity. The nature of the acyl group can be varied to impart suitable properties, e.g., acetate for ease of removal, benzoate for enhanced crystallinity, formate for enhanced water solubility.

In an alternative aspect, as illustrated in FIG. 16D (steps 2 and 3, above, combined), in a "telescoped variation" of this protocol of the invention, lactonization and acylation at the lactone 4-position is carried out in a single pot. When treated with 2 equivalents of an anhydride in the presence of a base (e.g., DMAP) the triol acid first undergoes lactonization followed by a regioselective acylation at the lactone 4-OH to form 4-acyllactone. This product is then isolated and purified by crystallization/precipitation from suitable solvent(s).

The invention provides a method for making acyl simvastatin from acyl lactone by, e.g., chemical or enzymatic acylation, as illustrated in FIG. 16E, or "Step 4." A combination of a dimethylbutyric acid derivative with a suitable acylation catalyst can be used to install the desired side-chain, e.g., the simvastatin side-chain. While the combination of dimethylbutyryl chloride/dimethylaminopyridine has been described, the reaction times are excessive, the conditions are harsh and lead to the formation of unacceptable levels of by-products. In contrast, the invention's combination of dimethylbutyric anhydride/Lewis acid (e.g., Bi(triflate)$_3$, Cu(triflate)$_2$), BF$_3$.Et$_2$O results in rapid reaction at room temperature. Screening of suitable Lewis acids and reaction conditions (temperature, solvent etc.) can identify the optimum conditions for this acylation.

In one aspect, enzyme-catalyzed acylation of the acyl lactone is used to install the dimethylbutyrate group at the 8-position under very mild conditions (rt-40° C., organic solvent) without formation of side products.

The invention provides a method for making simvastatin ammonium salt from acyl simvastatin, and simvastatin from simvastatin ammonium salt, as illustrated in FIG. 16F, or "Step 5." The final steps require the selective removal of the acyl group at the 4'-position. The acyl group at the 4'-position is highly susceptible to base-catalyzed elimination, even under only slightly basic conditions. Consequently, enzymatic hydrolysis has been the most convenient method for regioselective removal of this acyl group. It was demonstrated that the esterase that hydrolyzes lovastatin (SEQ ID NO:4, encoded, e.g., by SEQ ID NO:3) in step 1 (above) can also effectively catalyze the selective hydrolysis of acyl groups at the lactone 4'-position. When carried out at pH 7, this enzymatic hydrolysis yields simvastatin with the lactone ring substantially intact.

Any assay known in the art can be used for screening, characterization, etc. For example, enzyme screening can use any standard HPLC and TLC analyses, many of which are known to those skilled in the art.

The following describes another exemplary protocol and alternative conditions for practicing the methods of the invention:

Enzymatic Hydrolysis of Lovastatin to Triol Acid (Step 1)

SEQ ID NO:4 (encoded, e.g., by SEQ ID NO:3) was evaluated at 0.1-0.5 M concentrations of lovastatin or lovastatin acid in 7-10% MeOH/buffer, with the reaction being maintained at pH 9-9.5 by automatic addition of base. The best result was obtained at 0.5M lovastatin on a 500 mL scale using a lyophilized preparation of enzyme SEQ ID NO:4 (encoded by SEQ ID NO:3) (centrifuged supernatant from lysed cells) containing 14 mg/mL total protein; complete conversion of substrate was observed after 48 h.

Lactonization of Triol Acid to Diol Lactone (Step 2)

The reaction mixture was acidified (pH 2), and the precipitate collected by centrifugation and dried. The filtrate was extracted with iPrOAc and the organic extract was added to the dried filter cake. The resulting suspension was heated to reflux in a Dean-Stark apparatus until lactonization was complete. The resulting solution was filtered through a Celite pad, and the filtrate was washed with saturated (satd.) NaHCO$_3$. The resulting iPrOAc solution was concentrated until (×0.5), diluted with hexanes and cooled to 0° C. The precipitated solid was filtered and air-dried to yield diol lactone (63 g, 79.5% isolated yield; another 10.3 g of product was identified in various washes and mother liquors). The product contained <1% lovastatin.

Enzymatic Acylation of Diol Lactone (Step 3)

A mixture of diol lactone (25 mM), vinyl acetate (250 mM) and *Candida antarctica* lipase B (33 mg) in TBME (1 mL) was shaken at room temperature (RT). After 44 hours (h), HPLC indicated the formation of the monoacetate with 60% conversion.

Preparation of Acetyl Simvastatin (Step 4)

4-Acetyl lactone was dried under vacuum overnight at room temperature, stored under nitrogen, then dissolved in anhydrous methylene chloride (1 g/2.5-3 ml ratio) at room temperature under nitrogen. Meanwhile, Cu(OTf)$_2$ (5 mol %) was dissolved in the minimum amount of acetonitrile at room temperature, then 1.05-1.2 eq of dimethylbutyric anhydride was added to the solution, stirring at room temperature for 30 min to hour. This Cu(OTf)$_2$/anhydride solution was transferred into the 4-Acetyl lactone solution through syringe at room temperature under nitrogen with stirring. When complete (monitored by HPLC), the reaction was quenched by addition of water, and washed with satd., NaHCO$_3$ The isolated organic layer was dried over Na$_2$SO$_4$, filtered and evaporated to obtain crude 4-acetyl simvastatin (>99%).

Enzymatic Hydrolysis of Acetyl Simvastatin (Step 5)

This exemplary protocol for the enzymatic hydrolysis of acetyl simvastatin uses: 3.22 g acetylsimvastatin (final concentration 350 mM); 2 ml MeOH; 100 µl 4M Tris; 9.9 ml water, 8 ml SEQ ID NO:4 (encoded, e.g., by SEQ ID NO:3) (125 mg/ml lyophilized lysate in water).

Figure 7:
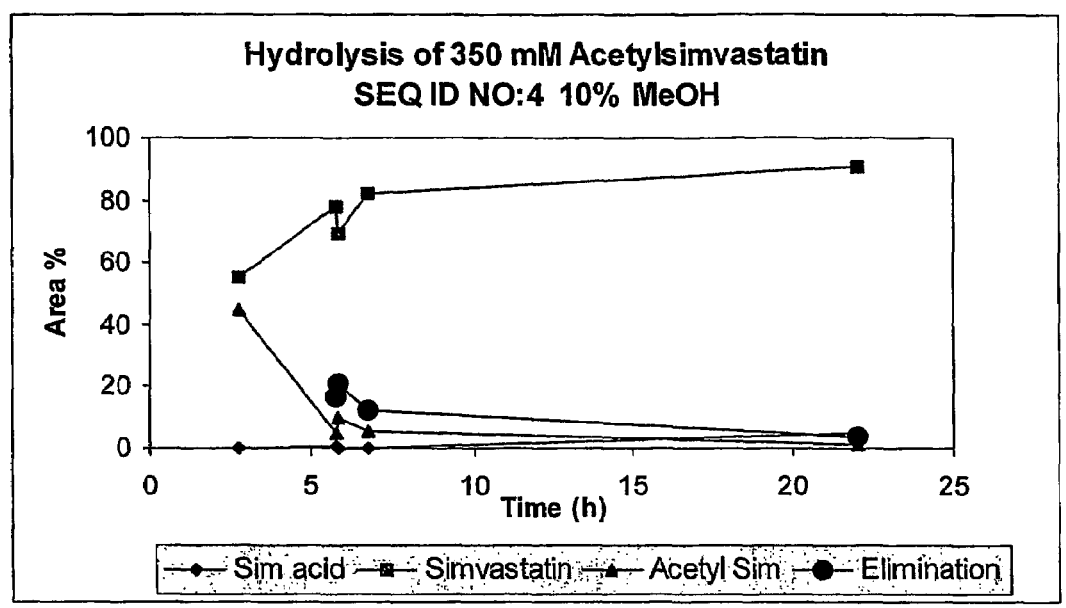
FIG. 7 illustrates an HPLC analysis of the results of an exemplary protocol for the enzymatic hydrolysis of acetyl simvastatin, as discussed in detail in Example 6, below.

The reaction is performed in a 25 ml vessel with overhead stirring and a magnetic stirrer bar. pH-stat conditions are maintained by a DasGip Stirrer-Pro® system; a pH of 7 is maintained by addition of 10% NH$_4$OH. As the conversion approaches ~75%, 4 ml of toluene are added to solubilize the material. The reaction is allowed to proceed overnight, at which time further solvent (toluene or methylene chloride) is added to ensure that all insoluble material is dissolved. A sample is analyzed by HPLC, as illustrated in FIG. 7.

Final composition of the reaction: Simvastatin acid 4.7%, Simvastatin 90.9%, Acetyl simvastatin 0.9%, Putative elimination product of simvastatin 3.5%. Final conversion 95.6%

Example 7

Exemplary Protocols of the Invention

The following example describes exemplary protocols of the invention, including schemes for synthesizing simvastatin from lovastatin, e.g., schemes to increase the overall yield of the process outlined in FIG. 5, a heterodiacylation synthetic route to simvastatin. This example describes schemes to increase the overall yield of lovastatin to simvastatin to at least 60%, and to identify where yield loss is occurring and where process improvements could be effected.

Step 1: Lovastatin Hydrolysis

FIG. 15A illustrates an exemplary reaction of the invention, hydrolysis of lovastatin to a triol acid using an esterase. In one aspect, this step involves an initial chemical opening of the lactone ring (using 1 equivalent NaOH) to form the water soluble lovastatin acid. After adjustment of pH and volumes, a slurry of the enzyme was added to the reaction, which was then maintained at pH 9.5 and 40° C. until 99.5% conversion of lovastatin acid. Alternative exemplary conditions use a 10% w/v loading of substrate (0.25 M) and a 10% w/w crude enzyme/substrate loading.

Previously at >100 g scale in the laboratory, the most convenient workup was to dilute and acidify the enzymatic reaction mixture. The insoluble materials were collected by filtration and this damp filter cake was dried in a vacuum oven at 30° C. to 40° C. Assaying the crude product ($^1$H NMR in the presence of an internal standard) indicated that it contained ~78% triol acid, the rest of the material being presumably denatured protein, cell and media components.

Studies were done to answer the question as to whether unacceptable yield loss occurred at this initial step. It was suspected that the relatively high enzyme loading resulted in:
  (i) Irreversible absorption of product to the precipitated protein,
  (ii) Loss of yield due to side reactions especially if the precipitated enzyme was carried forward to Step 2, the lactonization/acetylation
  (iii) Crude enzyme preparation containing other components capable of reacting with product at this or subsequent stages.

Attempts were made to improve the situation by:
  (i) Decreasing the enzyme loading
  (ii) Increase the purity of the enzyme preparation by a simple pre-treatment before use
  (iii) Separate the triol acid product from spent enzyme by means of ultrafiltration.

Decreased Enzyme Load

Figure 23:
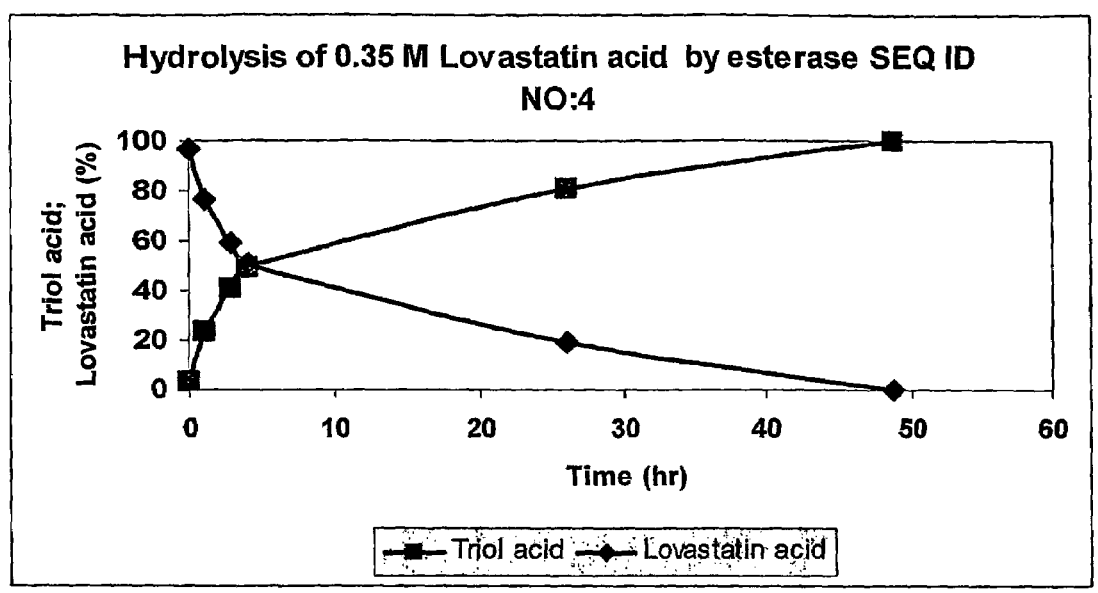
FIG. 23 is an illustration of studies for the enzymatic hydrolysis of lovastatin with the esterase of SEQ ID NO:4, as described in detail in Example 7, below.

Initially Step 1 was carried out at 20% w/v substrate (0.5 M) with a 20% w/w enzyme/substrate loading. Under these conditions the reaction was generally complete in 24-36 h at 40° C. The reaction was subsequently diluted before acidification and precipitation of the product; acidification at 0.5 M invariably resulted in thick slurries that were difficult to agitate. For example, preliminary studies for the enzymatic hydrolysis of lovastatin with the esterase of SEQ ID NO:4 was carried out at a loading of 0.35 to 0.5 M at 15% to 20% loading, as illustrated in FIG. 23. These studies showed that high substrate loading could be achieved; however, the rate of conversion required optimization.

Since the reaction already required dilution during workup, decreasing the substrate concentration to 0.25 M (10% w/v) and decreasing the charge of the crude enzyme to 10% would not affect the volumetric efficiency of the process. Under these conditions the enzymatic hydrolysis provided 99.5% conversion of lovastatin acid to triol acid in 24-36 h.

Enzyme Pre-Treatment

Heat treatment has often been used as a convenient method to purify crude enzyme preparations when there is differential thermal stability between the desired enzyme and other contaminating proteins. Since lovastatin esterase exhibited good thermal stability (Steps 1 and 4 are carried out at 40-50° C.) it was subjected to 60° C. for 30 min, then centrifuged and the supernatant used in the hydrolysis. There was no difference in activity between the heat pre-treated enzyme and untreated enzyme.

Ultrafiltration

Ultrafiltration was considered as a method to separate the triol acid product from spent enzyme and other high molecular weight impurities which might decrease yield at this or subsequent steps either by absorption or side reactions.

After the lovastatin hydrolysis was complete the reaction mixture containing the soluble triol acid salt was passed through a hollow fiber membrane assembly (Spectrum Labs MINIPROS™ hollow fiber module with a polysulfone microporous membrane; 10K cutoff; 1050 cm$^2$ surface area). The effluent was collected and the remaining residue was diluted with water and passed through the assembly. The combined eluents were then acidified and the precipitated triol acid collected. Unlike the 4-acetylsimvastatin hydrolysis step, with one exception, no major holdup of product was observed in the retained residue. The following Table shows the results of several experiments:

| Run | Scale g | Workup | Product[1] Purity % | Product[2] Yield % | Total[3] Yield % |
|---|---|---|---|---|---|
| 1 | 40 | Acid precipitation[4] | 57 | 85.1 | 86 |
| 2 | 40 | Ultrafiltration[5] | 83.8 | 77.8 | 86 |
| 3 | 50 | " | 82.7 | 77.9 | 83 |
| 4 | 80 | " | 86.6 | 76.5 | 93.7 |
| 5 | 50 | " | 90.3 | 84.4 | 89.5 |
| 6 | 50 | Acid precipitation | 84.0 | 88.7 | 91.9 |
| 7 | 5 | Ultrafiltration | n/d | n/d | 93-97 |

Figure 8:
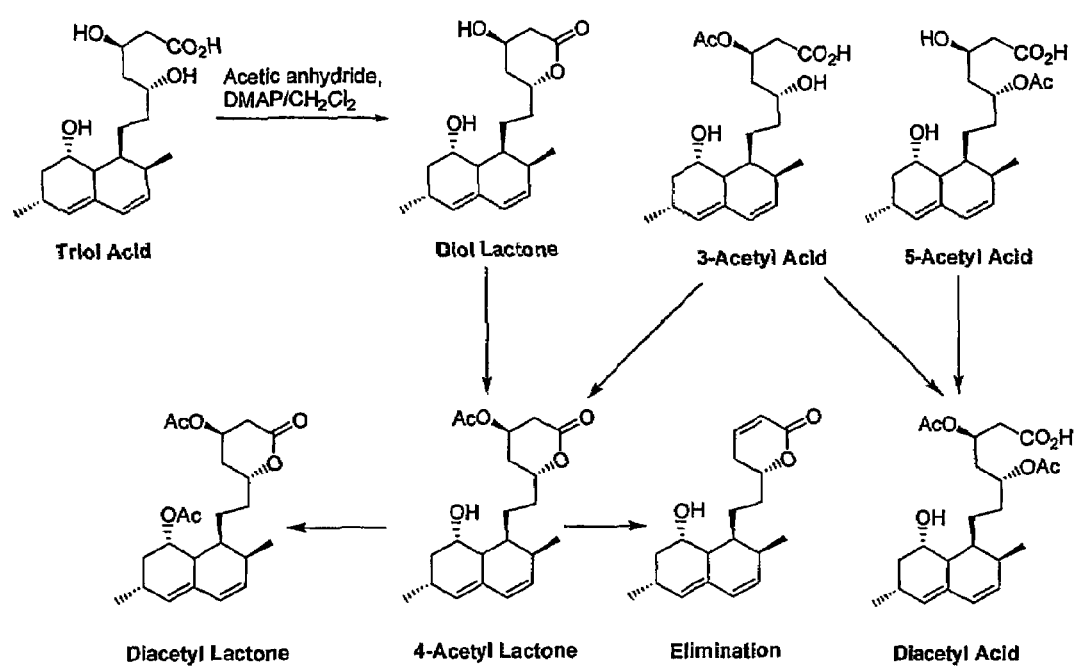
FIG. 8 illustrates an exemplary lactonization/acetylation reaction of the invention, and its products, as discussed in detail in Example 7, below.

[1]HPLC assay of the crude triol acid versus & working standard
[2]Yield of isolated triol acid based on HPLC purity
[3]Total yield comprising of isolated material and product (both triol acid and diol lactone) in washes, filtrates, residues
[4]Acidification of the reaction mixture and filtration of the precipitated triol acid and spent enzyme
[5]Reaction mixture passed through a hollow fiber bundle before precipitation Step 2: Acetylation FIG. 8 and FIG. 9 illustrate scheme 2, an exemplary lactonization/acetylation reaction of the invention, and its products. The crude product from the lovastatin hydrolysis step contains triol acid and denatured protein and cell/media components. Previously this crude material was suspended in $CH_2Cl_2$ (10-15% w/v) and treated with acetic anhydride (3 equivs.) in the presence of DMAP (0.15 equivs.), in a one step/one pot process. The reaction was monitored by HPLC and was typically terminated when <2% diol lactone remained; at this point <2% of diacetate was formed. Some elimination product was formed, especially if the reaction was stirred for excessively long periods. After completion the reaction was quenched by the addition of water, and the insoluble materials removed by filtering through a Celite pad. This pad was washed with $CH_2Cl_2$ and the combined filtrates washed with dilute acid (to remove DMAP) and with satd. $NaHCO_3$ to remove acetic acid. After base extraction, the solution is dried, filtered and concentrated. Addition of hexanes then leads to the precipitation of 4-acetyllactone as a white solid.

It was previously believed that under these conditions initial exclusive lactonization occurred, followed by acetylation at the 4-hydroxyl; only at long reaction times did bisacetylation and elimination become significant.

Some data suggest that a measurable amount of acetylation occurs first at the 3 and/or 5-hydroxyls of the open chain form; acetylation at the 4-hydroxyl followed by lactonization generates the desired product, but acetylation at the 5-hydroxyl ultimately generates the bisacetyl acid form (see the scheme illustrated in FIG. 8). This impurity had been previously mistaken for the elimination product as both have similar HPLC retention times.

Data in the table of FIG. 14 offers a comparison of the one step lactonization/acetylation conditions using either diol lactone (which cannot form the diacetyl acid side product) or triol acid as the starting material.

In general, the triol acid gave a lower yield of 4-acetyllactone as 5-8% of material was diverted to the diacetyl acid side-product.

One strategy to avoid this impurity is to carry out an acid-catalyzed lactonization to form the diol lactone exclusively, followed by acetylation. This sequence can be carried out in the same pot without isolation of the diol lactone (one pot/two step process). A direct comparison of the two processes was carried out on 50 g scale, as summarized in the following Table. The two processes were comparable, with a 3-4% overall yield in favor of the two step acetylation process.

| Lovastatin MW 404.54 | Triol acid Workup | Acetylation conditions | 4-Acetyllactone Isolated % | Overall Yield[5] % |
|---|---|---|---|---|
| 50 g | Acid precipitation[1] | One pot/one step[3] | 82.1 | 83.5 |
| 50 g | Ultra-filtration[2] | One pot/two step[4] | 85.1 | 87.3 |

[1]Acid precipitation of triol acid and enzyme
[2]Reaction mixture filtered through a hollow fiber bundle before acid precipitation
[3]Acetic anhydride only
[4]Acid catalyzed lactonization followed by acetylation
[5]Includes isolated material and material in mother liquors Since the data in this Table indicates that the acetylation step displays good mass balance, the majority of the yield loss occurs in Step 1, Lovastatin hydrolysis and isolation.

Step 3: Acylation

Figure 10:
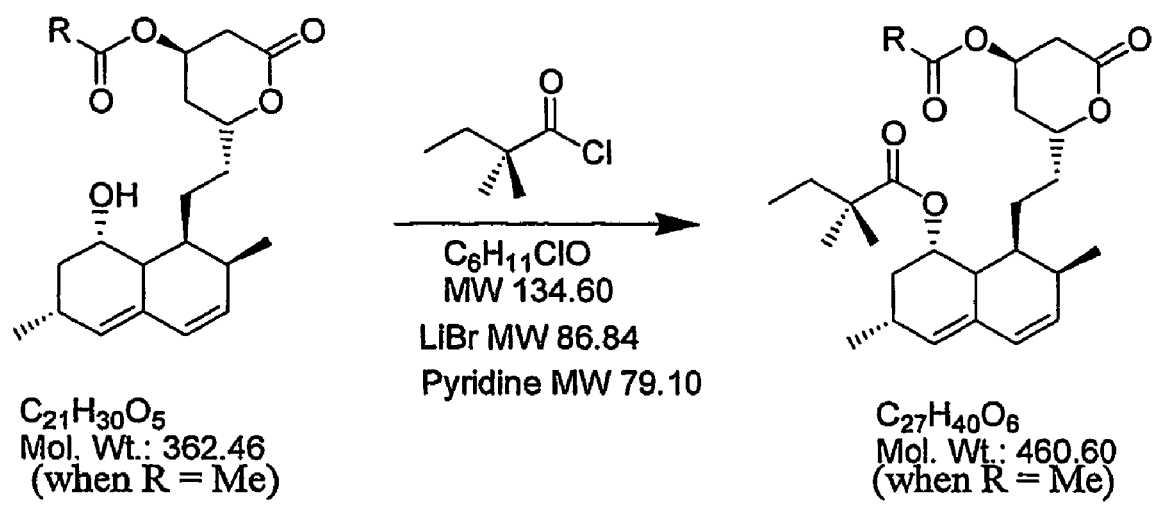
FIG. 10 illustrates an exemplary protocol for chemical acylation of the 8-position, as discussed in detail in Example 7, below.

An exemplary protocol for chemical acylation of the 8-position of the lactone is illustrated in FIG. 10. Previous conditions had used 2,2-dimethylbutyric anhydride as the acylating agent for introduction of the simvastatin side chain. The anhydride is not commercially available, and the use of multiple equivalents of the acid chloride in its preparation resulted in a very high chemical cost contribution to the overall process.

Experiments used the commercially available dimethylbutyryl chloride (2 equivs.) in the presence of LiBr as an acylation catalyst with pyridine (2 equivs.) to trap the released acid. After workup the product solution is evaporated to dryness, and the resultant solid is triturated with iPrOH and the slurry filtered to yield 4-acetylsimvastatin of acceptable quality (86-89% overall yield; 95% pure).

Step 4: Enzymatic Deacetylation

Figure 11:
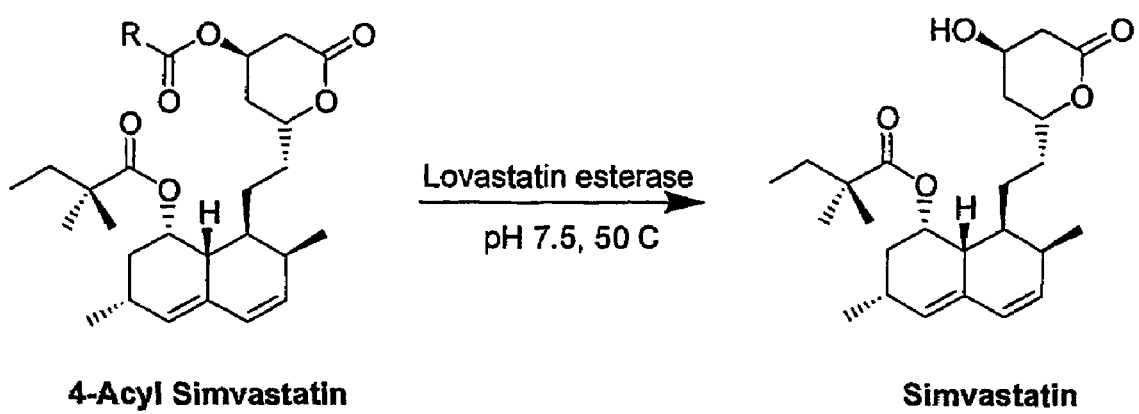
FIG. 11 illustrates an exemplary reaction of the invention, the enzymatic deacetylation of 4-acetyl simvastatin, as discussed in detail in Example 7, below.

FIG. 11 illustrates an exemplary reaction of the invention, the enzymatic deacetylation of 4-acetyl simvastatin. There are two significant hurdles to overcome in the enzymatic deacetylation of 4-acetyl simvastatin:

The insolubility of both the starting material, 4-acetylsimvastatin, and the product, simvastatin, in aqueous solution, The sensitivity of the 4-acetyl group, which rapidly undergoes elimination at pH >7.

Unlike the lovastatin hydrolysis reaction, the hydrolysis 4-acetyl simvastatin must be run close to pH 7 where increasing the solubility by opening the lactone ring is not possible. To improve this step, the same strategies were explored as for the Lovastatin hydrolysis:

(i) Decreasing the enzyme loading
(ii) Increase the purity of the enzyme preparation by a simple pre-treatment before use
(iii) Separate the product from spent enzyme by means of ultrafiltration
(iv) Use of surfactants to increase solubility of substrate
  (i) Again using a substrate concentration of 10% w/v (0.25 M) and decreasing the crude enzyme load to 10% w/w still gave a reaction that showed >95% conversion in 48 h.
  (ii) Alternative exemplary hydrolysis reactions have been run using the supernatant fractions from heat pre-treated enzyme.
  (iii) The use of ultrafiltration to purify the product complicated the workup. Simvastatin is insoluble in water (0.03 mg/mL). However, when conversion was complete the pH of the reaction mixture was raised by the addition of 1 equivalent of NaOH, resulting in opening of the lactone ring and dissolution of the product. The reaction mixture was then filtered through a hollow fiber membrane assembly to separate the spent enzyme. Unlike the lovastatin hydrolysis, ultrafiltration of reaction solutions containing simvastatin acid and spent enzyme resulted in significant amounts of product being retained within the membrane assembly.

The eluent was acidified, the simvastatin acid did not precipitate and was extracted, and precipitated as its ammonium salt. The overall recovery for this sequence was poor.

(iv) Five surfactants (Triton X-100, Tween 80, Tween 20, AOT and CTAB) were examined for their ability to enhance the hydrolysis reaction by increasing the substrate solubility. Triton X-100 at 0.05% w/v did increase the rate of reaction at small scale (1 g). However the effect became less pronounced as the reaction scale increased.

The final reaction conditions used 5% MeOH as a "wetting" agent; otherwise the insoluble starting material tended to "creep" up the walls of the flask. When deemed complete (>95% conversion), the reaction mixture was filtered and the filter cake dried under vacuum. The dried filter cake was suspended in CH$_2$Cl$_2$, giving a brown/gray viscous solution containing gel-like material. This was filtered through a pad of Celite and the Celite pad washed with toluene. Removal of the CH$_2$Cl$_2$ from the filtrate and addition of hexanes precipitated simvastatin in 88-89% overall yield (97.5% purity versus standard). Further batches of crude simvastatin were all crystallized from toluene/hexanes as the single purification method.

Steps 1-4: Overall Process Yield

Overall Yield

The following Table ("Yield Summary for Overall Process") showcases the overall process results for two 50 g scale campaigns.

| | | Yield Summary for Overall Process | | | | |
|---|---|---|---|---|---|---|
| Lovastatin g | Step 1 Triol Acid Workup | Step 2 4-AcLactone % Isolated (Overall)[1] | Step 3 4-AcSim % Isolated (Overall) | Step 4 Simvastatin % Isolated (Overall) | Steps 1-4 % Isolated[2] (% mother liquors) | Purity % |
| 50 | Enzyme filter cake[3] | 82.1 (83.5) 1 step process[5] | 88.5 (94.5) | 81.5 (88.9) | 58.3 (4.5) | 97.42 |

-continued

Yield Summary for Overall Process

| Lovastatin g | Step 1 Triol Acid Workup | Step 2 4-AcLactone % Isolated (Overall)[1] | Step 3 4-AcSim % Isolated (Overall) | Step 4 Simvastatin % Isolated (Overall) | Steps 1-4 % Isolated[2] (% mother liquors) | Purity % |
|---|---|---|---|---|---|---|
| 50 | Ultrafiltration[4] | 85.1 (87.3) 2-step process[5] | 83.2 (89.7) | 73.5 (87.5) | 51.3 (8.7) | 97.49 |

[1]% Overall yield is isolated yield plus product in mother liquors/washes etc.
[2]% Yield of simvastatin based on a 50 g charge of Lovastatin
[3]Acid precipitation of triol acid and enzyme
[4]Reaction filtered through a hollow fiber membrane prior to triol acid isolation
[5]Simultaneous lactonization/acetylation or lactonization followed by acetylation The overall yield of Simvastatin was 51-58% with a further 5-8% of material remaining in the mother liquors (toluene/hexanes). This material passed elemental analysis and was 97.4-97.5% pure when subjected to a HPLC assay versus a standard of commercial grade simvastatin.

Impurity Profile

Figure 12:
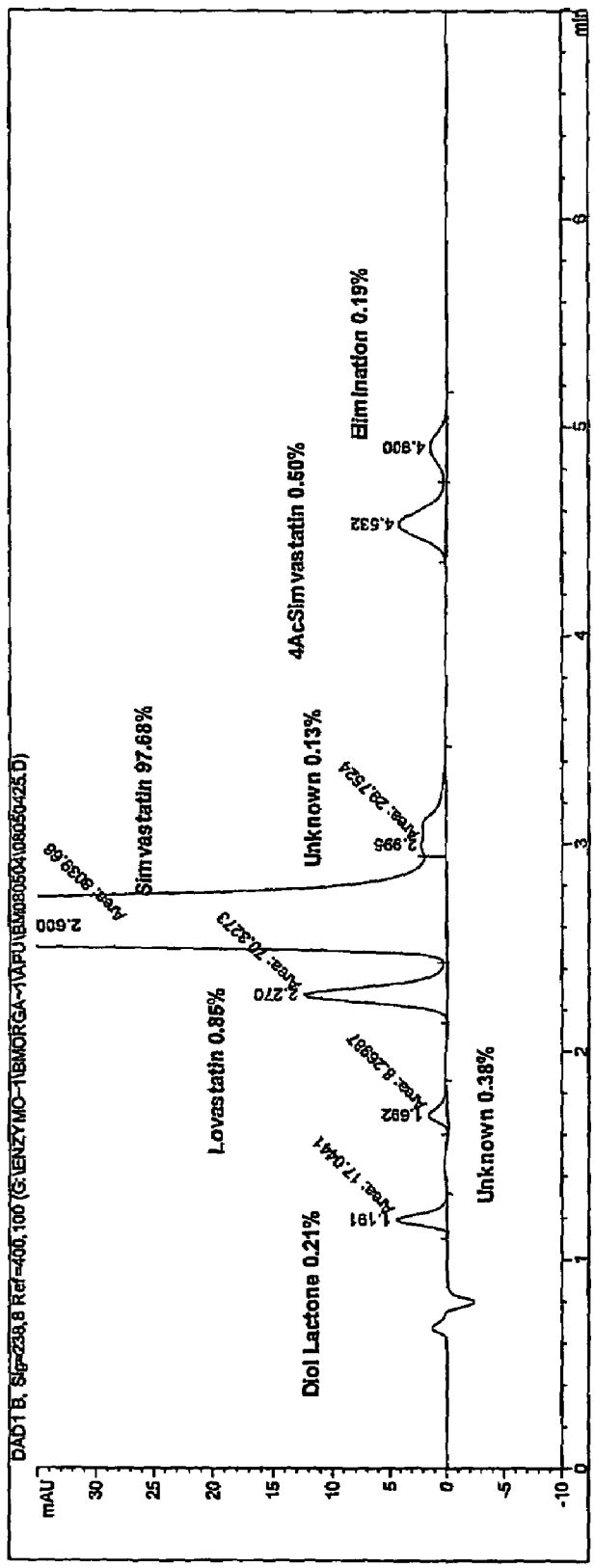
FIG. 12 illustrates HPLC traces for two batches of simvastatin generated using an exemplary protocol of the invention, as discussed in detail in Example 7, below.

FIG. 12 illustrates HPLC traces for two batches of simvastatin generated using this exemplary protocol of the invention. Both samples show simvastatin with a 98 area %. Recrystallization from toluene/hexanes reduced the levels of most impurities by at least 50% compared to the crude material, e.g., unreacted 4-acetylsimvastatin was reduced from 1.7-1.8% to 0.3-0.5%, and the elimination product was reduced even further from 1-2% to 0.2%. Levels of diol lactone and 4-Acetyl lactone were reduced from 0.5% to 0.1-0.2%.

Figure 13:
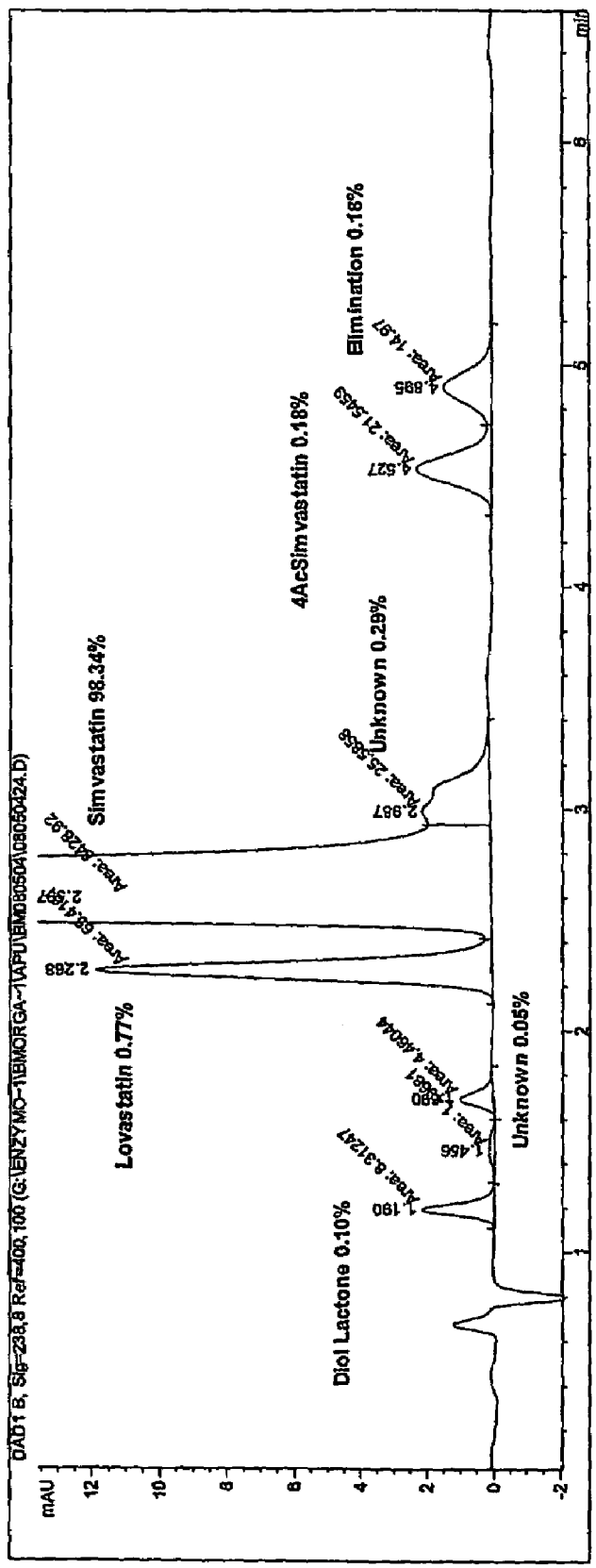
FIG. 13 illustrates an HPLC analysis showing an impurity profile for simvastatin samples generated using an exemplary protocol of the invention, as discussed in detail in Example 7, below.

FIG. 13 is an illustration of an HPLC analysis showing an impurity profile for simvastatin samples isolated from 50 g scale campaigns.

SUMMARY

Simvastatin was prepared from Lovastatin using an exemplary 4-step chemoenzymatic process of the invention.

In two demonstration campaigns on a 50 g scale, Simvastatin was isolated in 51 and 58% yield overall. The yield of isolated material for each step was: Steps 1-2, 82-85%; Step 3, 83-89% and Step 4, 74-82%. In Steps 3 and 4 a further 6-14% of product remained in the mother liquors.

The enzyme load was decreased to 10% crude enzyme/substrate, and heat pre-treatment and use of a centrifuged supernatant decreased the amount of debris loaded into the system. Ultrafiltration of reaction mixtures offered no clear advantage to isolating the product from the spent enzyme.

Reagents Needed in Complete Process:

Step 1: Lovastatin (kg); Lovastatin esterase; Tris buffer (L); MeOH (L); EtOAc (L); Hexanes (L).

Step 2: Diol Lactone (kg); Acetic anhydride (kg); Dimethylaminopyridine (g); Dichloromethane (L); EtOAc (L); Hexanes (L); 4-Acetyl Lactone.

Step 3: 4-Acetyl Lactone (kg); Dimethylbutyryl chloride (kg); Dichloromethane (L); EtOAc (L); MeOH (L); Hexanes (L); 4-Acetyl Simvastatin.

Step 4: 4-Acetyl Simvastatin (g); Lovastatin esterase; Tris buffer (L); EtOAc (L); Hexanes (L); Toluene (L); Simvastatin.

Example 8

Enzymatic Hydrolysis of Lovastatin

The following example provides an exemplary protocol of the invention comprising the hydrolysis of lovastatin.

Step 1: Enzymatic Hydrolysis

A 50 g and 2×150 g scale hydrolyses of lovastatin were carried out. The reactions were run at 0.5M substrate, pH 9.5, 40° C. with pH maintained constant by addition of 10% $NH_2OH$ All 3 reactions behaved similarly, achieving >99% conversion (by normalized HPLC peak area) in ~24 h.

The reaction mixtures were acidified to pH ~2.5. Depending on the scale of the reaction, the efficiency/power of the stirring and the extent of dilution, the reaction mixture may "solidify" during this operation, requiring further dilution.

The precipitated product was easily filtered and the damp filter cake dried at ~40° C. in a vacuum oven.

On standing, more triol acid and diol lactone precipitated from the acidic aqueous filtrate (1-4%)

Discussion

Although the reactions are run at 0.5 M (20 w/v) substrate, the reaction mixture must be diluted with up to an equal volume of water to prevent solidification of the reaction mixture during workup. The volumetric efficiency may be improved by running the reaction at 0.25M from the beginning. The 50 g reaction showed an abnormally high amount of triol acid in the aqueous filtrate (estimated at 12%), resulting in a lower overall yield at the next step.

Step 2: Lactonization/Acetylation 3 reactions were carried out using the dried filter cake (triol acid/precipitated protein) from the 50 and 150 g reactions. The reactions proceeded as expected under standard conditions (4 equivs. $Ac_2O$, 15% DMAP)

Product was precipitated from EtOAc/hexanes

The 4-acetyllactone was isolated in 66-78% yield (1$^{st}$ crop) over two steps; ~7% remained in the mother liquors Step 3: Acylation Two reactions on 26 g and 98 g scale were carried out under the usual conditions.

The smaller reaction provided a 79.8% yield of 4-AcSimvastatin in 2 crops. The product was isolated from MeOH (2×) (an attempt to precipitate the product from MeOH by addition of water was unsuccessful).

The 98 g reaction was divided into 2 process streams after workup. One portion (~25% of the material) was diverted directly to the final enzymatic hydrolysis step.

The rest of the material was precipitated from MeOH (2×) to give a 74% yield in two crops; a further 12% of product remained in the residues.

Step 4: Enzymatic Hydrolysis

A 27 g scale reaction (10% w/v substrate) was carried out at pH 7.5 and 55° C. (exterior temp). 98% conversion of 4-acetylsimvastatin was observed after 20 h. Assay of the crude isolated material indicated a 91% yield of simvastatin. The material was isolated and precipitated from toluene/hexanes to provide 88% yield of simvastatin in 2 crops. This represents a 46% overall yield from lovastatin. The impurity profile and the HPLC assay results are shown in Table, below.

In one instance, crude acetylsimvastatin was carried forward to the final enzymatic step without purification. The process stream in MeOH was concentrated by vacuum distillation to provide the correct concentration when diluted with water. However the substrate precipitated from the reaction mixture as an insoluble waxy ball which coalesced. Toluene was added the mixture to solubilize the substrate. Addition of enzyme resulted in a very slow reaction. After 92 h, the major product was simvastatin acid with ~20% elimination product.

A final 69 g scale reaction was slow at pH 7.5/50° C., requiring 4 days for adequate conversion, during which time ~10% simvastatin acid was formed. The product was isolated at a 60% yield.

Discussion

Isolation of simvastatin from the dried filter cake; extraction efficiencies have varied. Some experiments have shown longer reaction times, but this may reflect the quality of the substrate. The Table illustrated in FIG. 21 shows impurity profiles, HPLC assay and elemental analysis results for selected simvastatin samples.

Hydrolysis of Crude Lovastatin

The hydrolysis of crude lovastatin (91%) was carried out on 4×10 g scale using two lots of enzyme (SEQ ID NO:4, encoded by, e.g., SEQ ID NO:3) at pH 9.5/40° C. Reactions with this enzyme resulted in 99.5% conversion in this time period (one lot showed 96% conversion after 27 h, another lot at 20% loading showed 99.4% conversion in 18.75 h).

3 reactions were combined and processed as described herein. Assay indicated an 89.4% yield of triol acid as a crude filter cake with an estimated 5% lost to the aqueous filtrates.

The crude triol acid was lactonized/acetylated under conditions as described herein.

Example 9

Enzymatic Hydrolysis of Lovastatin

The following example provides an exemplary protocol of the invention comprising the enzymatic hydrolysis of lovastatin.

Step 1: Enzymatic Hydrolysis of Lovastatin

A. Separation of Spent Enzyme from Triol Acid

Heat Treatment

After enzymatic hydrolysis was complete, 4×10 g reactions were heated to 80-85° C. for 1 h. There was no obvious precipitation of denatured protein; the reactions remained a cloudy greenish/black color. Cooling to RT resulted in no apparent change in the color or viscosity of the reaction mixtures.

pH Manipulation

A solution of 10 g of enzyme powder in 10% MeOH/water at pH 10.5 does not filter easily when treated with CELITE® diatomaceous earth (3 g).

Adjusting to pH 6 results in a heavy precipitation which does not filter easily even after prolonged stirring with an equal weight of CELITE diatomaceous earth.

After adjusting to pH 6 and centrifugation, the supernatant still contains material which precipitates on lowering the pH further.

Triol acid is soluble at ~0.2M in the range pH 9.5-3.5.

Microfiltration

After centrifugation to remove a small amount of insolubles, 4×10 g combined enzymatic hydrolyses were filtered through a Spectrum Labs polysulfone hollow fiber bundle (10K MW cutoff; 1050 cm$^2$). This is a convenient method for removing the high MW materials from the reaction mixture before precipitation of the triol acid. The solution filters at a reasonable rate (~3-4 h for ~1 L solution).

After microfiltration, decreasing the pH of the effluent does not lead to precipitation until ~pH 4. The precipitated triol acid is easily filtered and dried under vacuum.

B. Performance of Enzyme Batches 4 lots of lovastatin esterase were used.

Comparison of the 4 enzyme lots at 0.5M/20% enzyme load and 0.25M/10% enzyme load showed comparable behavior for all lots with 99% conversion at 23 h and >99.5% conversion in 23-40.5 h.

Two enzyme use tests (4×10 g and 5×10 g) were subjected to the microfiltration workup. The isolated triol acid, in both cases, was only 82.7 and 83.8% pure when assayed against a working standard of triol acid. Only 83-86% of the material could be accounted for when the residues were assayed.

Step 2: Lactonization/Acetylation

Figure 22:
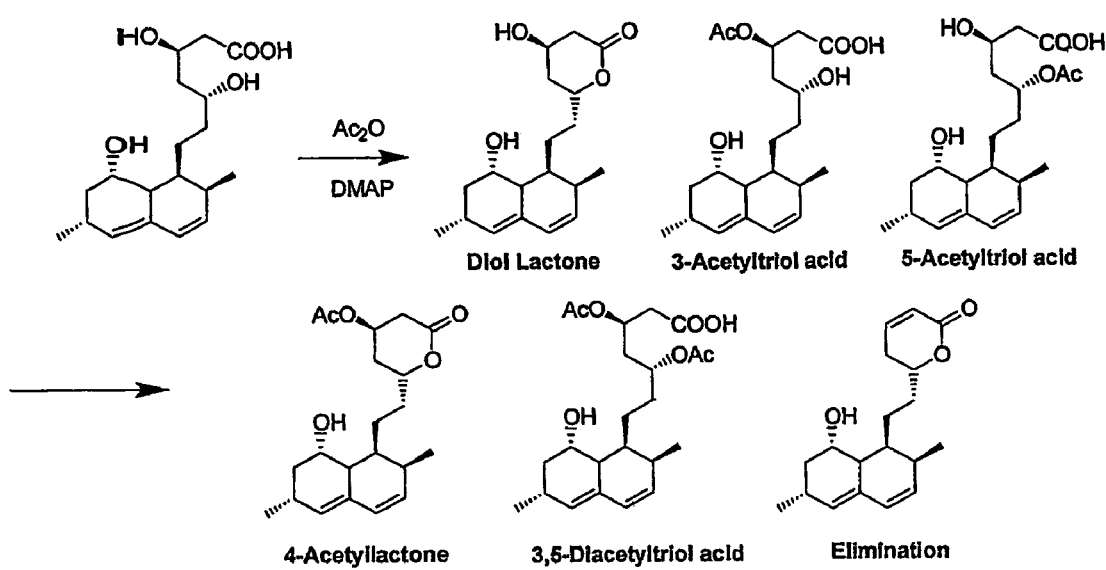
FIG. 22 is an illustration of exemplary reactions of the invention, e.g., the conversion of a triol acid to the corresponding diol lactone, 3-acetyltriol acid and 5-acetyltriol acid, and the subsequent conversion to 3,5-diacetyltriol acid, 4-acetyllactone and the elimination product, as discussed in detail in Example 9, below.

The invention provides methods comprising the conversion of a triol acid to the corresponding diol lactone, 3-diacetyltriol acid and 5-diacetyltriol acid, and the subsequent conversion to 3,5-diacetyltriol acid, 4-acetyllactone and the elimination product, as illustrated in FIG. 22.

Quantities of triol acid and diol lactone were prepared by chemical hydrolysis (KOH/MeOH) and azeotropic lactonization (iPrOAc). Compared to working standards the triol acid was 99.4% pure while the diol lactone was 94.5% pure.

Both compounds were subjected to lactonization and/or acetylation under standard conditions (Ac$_2$O, 15% DMAP; 10% w/v in CH$_2$Cl$_2$).

The reactions were monitored by HPLC and terminated by quenching with water, and washing with acid and NaHCO$_3$; the CH$_2$Cl$_2$ was diluted to a known volume and assayed against a working standard of 4-acetyllactone; all aqueous washes and residues were also assayed.

2 lactonization/acetylation reactions of triol gave assayed solution yields of 78.9% and 87.4%; impurities in the product included (HPLC area %): 0.4% diol lactone, 5.6% elimination, 1.5% 4,8-bisacetyllactone, 0.5% unknown.

2 acetylation reactions of diol lactone gave assayed solution yields of 88.5% and 94.7%; the impurity profile of the product was cleaner than for the triol acid reaction.

A previous reaction in CH$_2$Cl$_2$ under more dilute conditions at 0° C. showed the presence of 2 new peaks on HPLC with retention times longer than the diol lactone. These peaks decreased as the reaction proceeded. As the acetylation proceeds a peak just before the acetyl-lactone peak increases. This was previously assigned to the eliminated lactone product. LC-MS data suggests that this peak is actually a composite of the elimination product and the 3,5-diacetyltriol acid. See FIG. 22 for an illustration of these reactions and their corresponding products (the conversion of a triol acid to the corresponding diol lactone, 3-diacetyltriol acid and 5-diacetyltriol acid, and the subsequent conversion to 3,5-diacetyltriol acid, 4-acetyllactone and the elimination product.

Acetylation of preformed diol lactone gave higher yield and cleaner product than lactonization/acetylation of triol acid.

Step 3: Acylation
Retained samples of 4-acetylylsimvastatin are being analyzed by HPLC (238 and 210 nm UV detection and ELSD), and LC-MS.
No major new peaks were observed in the 210 nm or ELSD spectra.
Lack of compound ionization hampered LC-MS analysis of minor impurities.

Step 4: Enzymatic Hydrolysis
Alternative methods of the invention for the removal of a 4-acetyl group:
Enzyme catalyzed alcoholysis: no reaction with 5 enzymes in toluene in the presence of MeOH (32 equivs.); addition of water (0.6% v/v) to these reactions did not result in any hydrolysis.
Enzymatic hydrolysis in wet water-miscible solvents (9 solvents); no sign of product with one lot of enzyme (SEQ ID NO:4, encoded by, e.g., SEQ ID NO:3) after 43 h, with varying degrees of elimination.
Enzyme catalyzed aminolysis: 7 enzymes using nBuNH$_2$ in toluene or MTBE; background elimination is the major product
$H_2O_2$/NaHCO$_3$: increasing amounts of 50% $H_2O_2$ in MeOH, THF or acetone in the presence of excess solid NaHCO$_3$; no sign of acetate removal.
Acid catalyzed methanolysis; 0.1M acetylsimvastatin in 30% HCl/MeOH overnight forms a mixture of simvastatin and simvastatin methyl ester.

Example 10

Fractional Factorial Design of Enzymatic Hydrolysis of Lovastatin

The enzymatic hydrolysis of lovastatin was subjected to fractional factorial design for optimization of the reaction. The fractional factorial design was done with DESIGN EXPERT™ software on 0.35M lovastatin acid, Na salt, the results are illustrated in FIG. 24. Notes for FIG. 24 are:
1 Enzyme activity was measured on methyl umbelliferyl butyrate and expressed as the slope obtained for 0.1 µg total protein.
2 Rate of triol acid formation up to 3 h.
3 Triol acid formed at 45.5 h (%).

Figure 25:
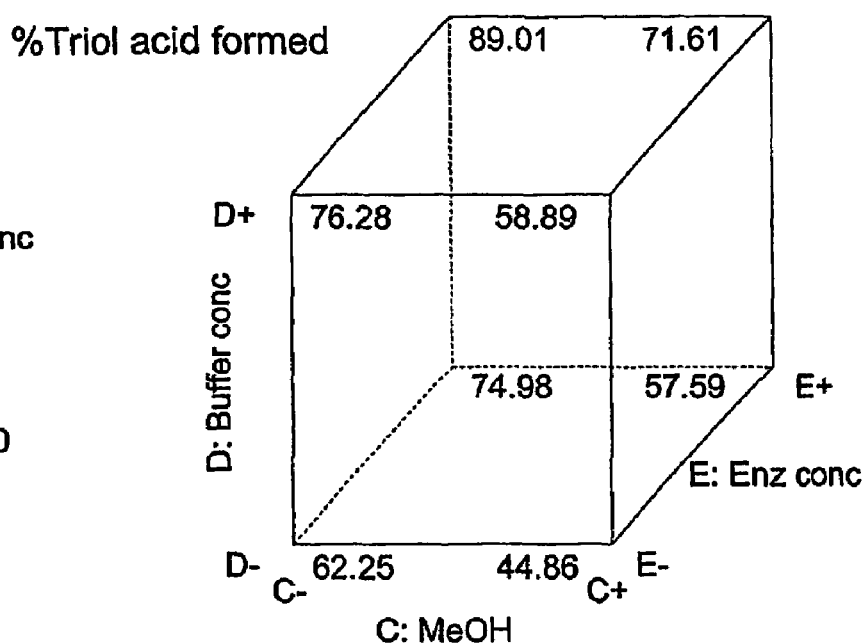
FIG. 25 is an illustration summarizing the four factors that affect lovastatin acid hydrolysis, as described in detail in Example 10, below.

Four factors affect lovastatin acid hydrolysis: % Triol acid formed, enzyme concentration, buffer concentration, and the amount of MeOH, as illustrated in FIG. 25, where all reactions performed with clarified lysate of *E. coli* containing SEQ ID NO:4, and reactions carried out under pH-stat conditions in a DasGip FEDBATCH—PRO® system.

A Response Surface Analysis (RSA) was performed using central composite design for hydrolysis of 0.35 M Lovastatin using DESIGN EXPERT® software, the results are illustrated in FIG. 26. Notes for FIG. 26 are:
1 Enzyme activity was measured on methyl umbelliferyl butyrate and expressed as the slope obtained for 0.1 µg total protein (RFU/s).
2 Rate of triol acid formation up to 3 h.
3 Triol acid formed at 45.5 h (%).

Figure 27:
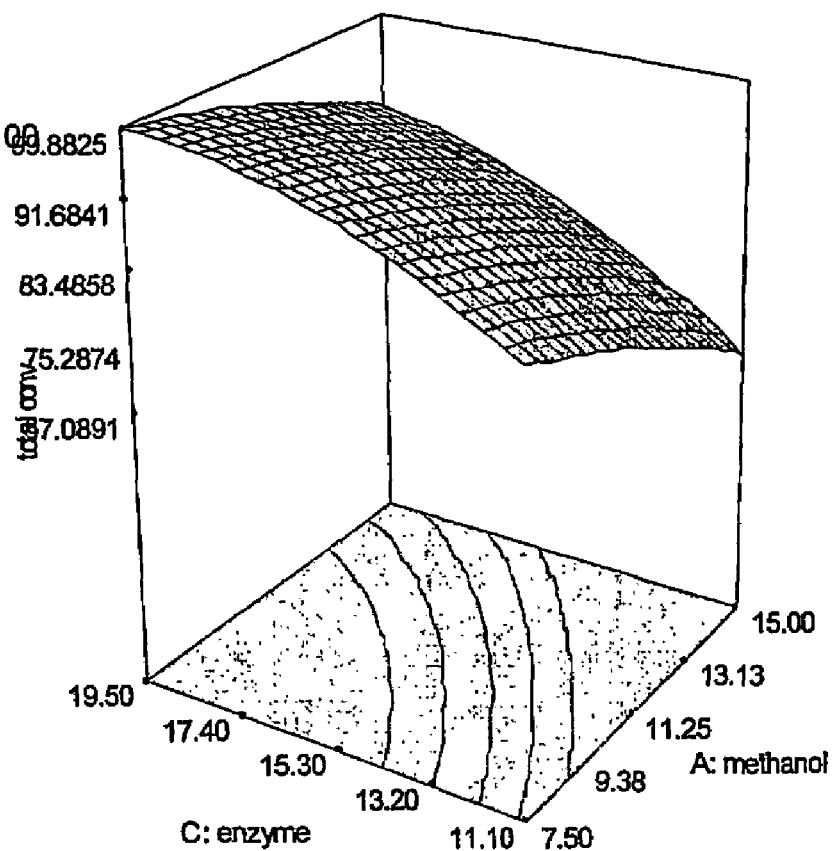
FIG. 27 illustrates results of optimization of in situ hydrolysis of lovastatin with SEQ ID NO:4, as described in detail in Example 10, below.

The in situ hydrolysis of lovastatin with SEQ ID NO:4 was optimized such that insignificant amounts of NaCl generated: 0.85 g lovastatin in MeOH and equimolar NaOH added. Clarified lysate of *E. coli* containing SEQ ID NO:4 was added to lovastatin acid. Significant factors were: methanol concentration ([MeOH]), enzyme concentration ([Enzyme]) was highly significant, and buffer concentration ([Buffer]) had a slight effect at low [Enzyme]. See FIG. 27 for an illustration summary of the results.

Figure 28:
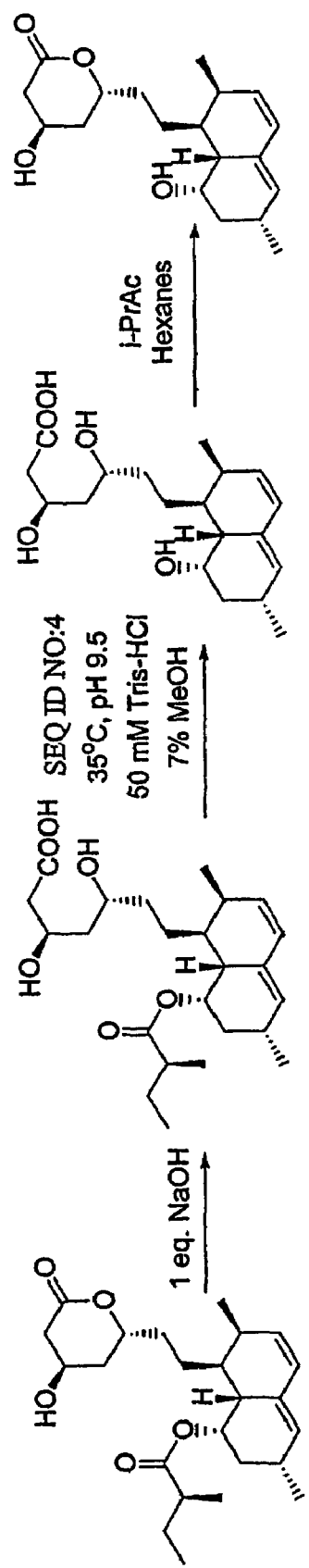
FIG. 28 illustrates an exemplary reaction of the invention, a large-scale hydrolysis of lovastatin protocol, as described in detail in Example 10, below.

The results of Response Surface Analysis (RSA) can be applied to large-scale hydrolysis of lovastatin, e.g., using a protocol as illustrated in FIG. 28:
Reaction performed successfully on 100 g scale (0.5 M);
97.5% conversion in 27 h;
Productivity: x g/g esterase/h;
Specific activity: 0.084 µmol/mg esterase/min.

Figure 29:
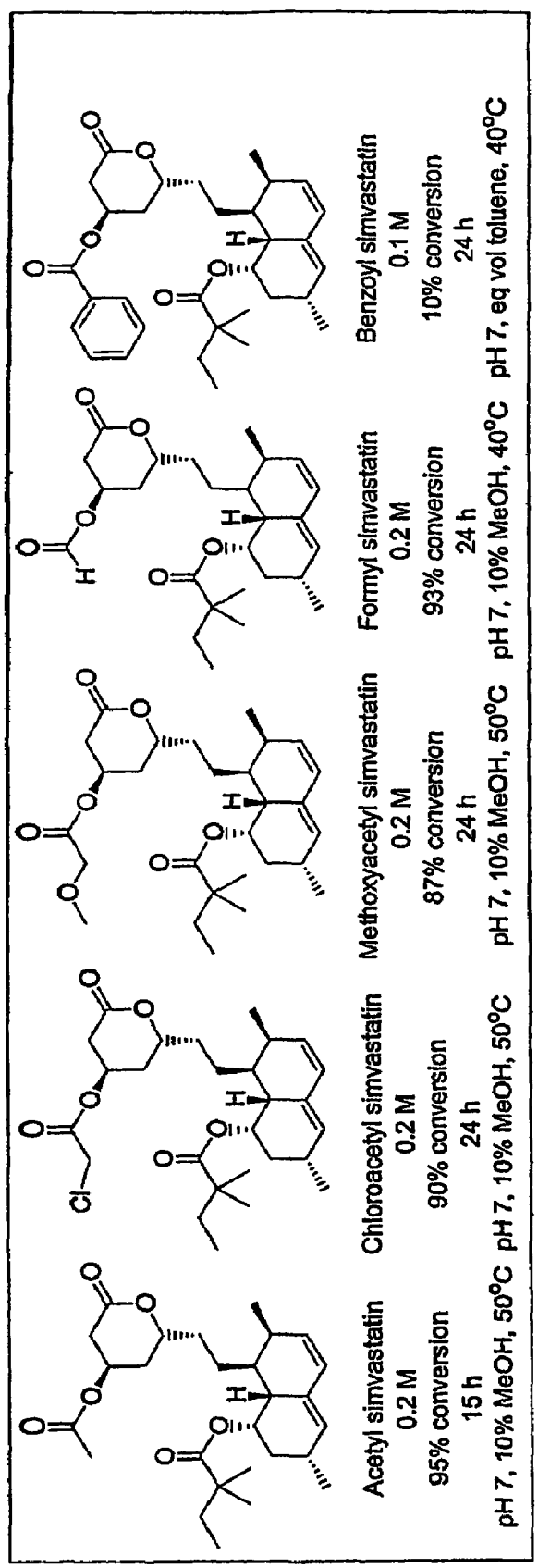
FIG. 29 illustrates 4-acyl derivatives of simvastatin hydrolyzed by SEQ ID NO:4, as described in detail in Example 10, below.

Substrate specificities of SEQ ID NO:4 were studies: many 4-acyl derivatives of simvastatin are actively hydrolyzed by SEQ ID NO:4, as illustrated in FIG. 29. Chemical hydrolysis of Acetylsimvastatin results in dehydration of the lactone ring.

Example 11

An Exemplary Hydrolysis Protocols

Figure 30:
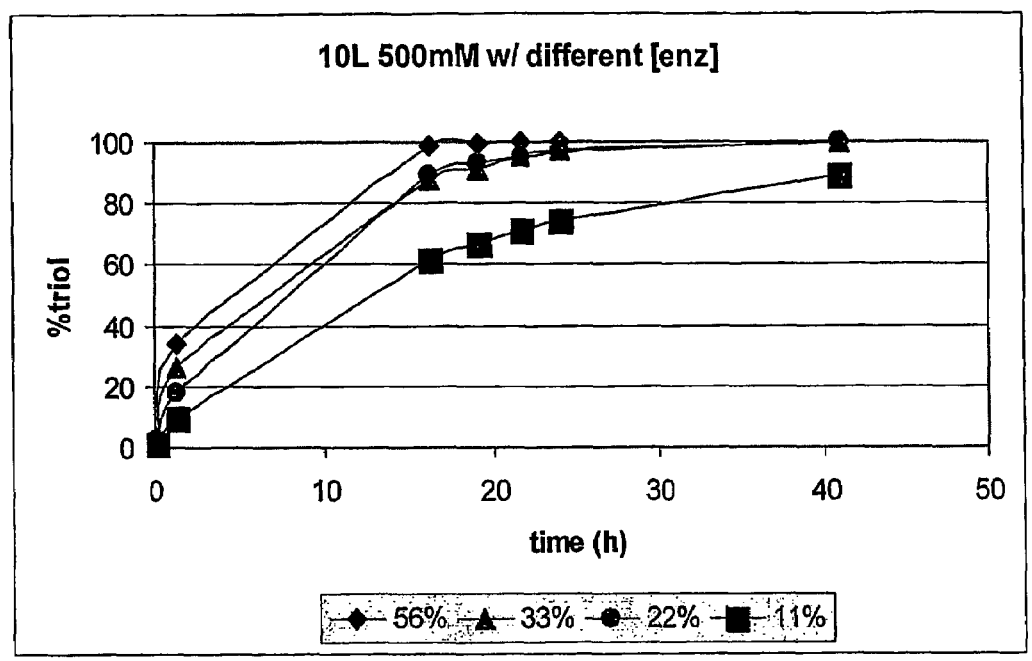
FIG. 30 illustrates the results of an exemplary lovastatin hydrolysis protocol of the invention using SEQ ID NO:4, as described in detail in Example 11, below.

This example describes exemplary protocols of the invention, including industrial scaled up processes for making simvastatin and intermediates, e.g., as in FIGS. 5 and 6. A protocol for the enzymatic hydrolysis of lovastatin to triol acid using SEQ ID NO:4 (see, e.g., step 1, FIG. 5) was completed, and FIG. 30 illustrates the results of this exemplary lovastatin hydrolysis protocol. Enzyme source of SEQ ID NO:4 was lysate from mini-fermentors. The protocol resulted in 99% conversion at 39 h (90% 24 h) on 12 g scale (0.5M) with lyophilate from 10 L fermentation (214 g). Summarizing the parameters used in this study:

| Catalyst Load | Conversion | Time |
| --- | --- | --- |
| 56% w/w | 100% | about 4 h |
| 33% w/w | 97% | about 24 h |
| 22% w/w | 97% | about 24 h |

At 22% w/w lyophilate loading, using 10 L fermentation hydrolyzes 1 kg lovastatin.

Figure 31:
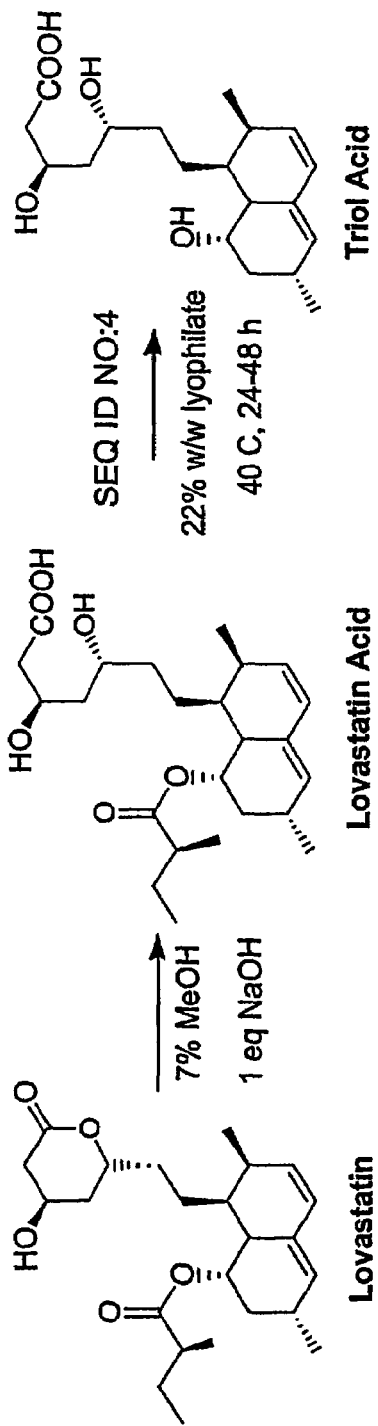
FIG. 31 illustrates an exemplary enzymatic hydrolysis of lovastatin to triol acid in scaled-up protocol, as described in detail in Example 11, below.
Figure 32:
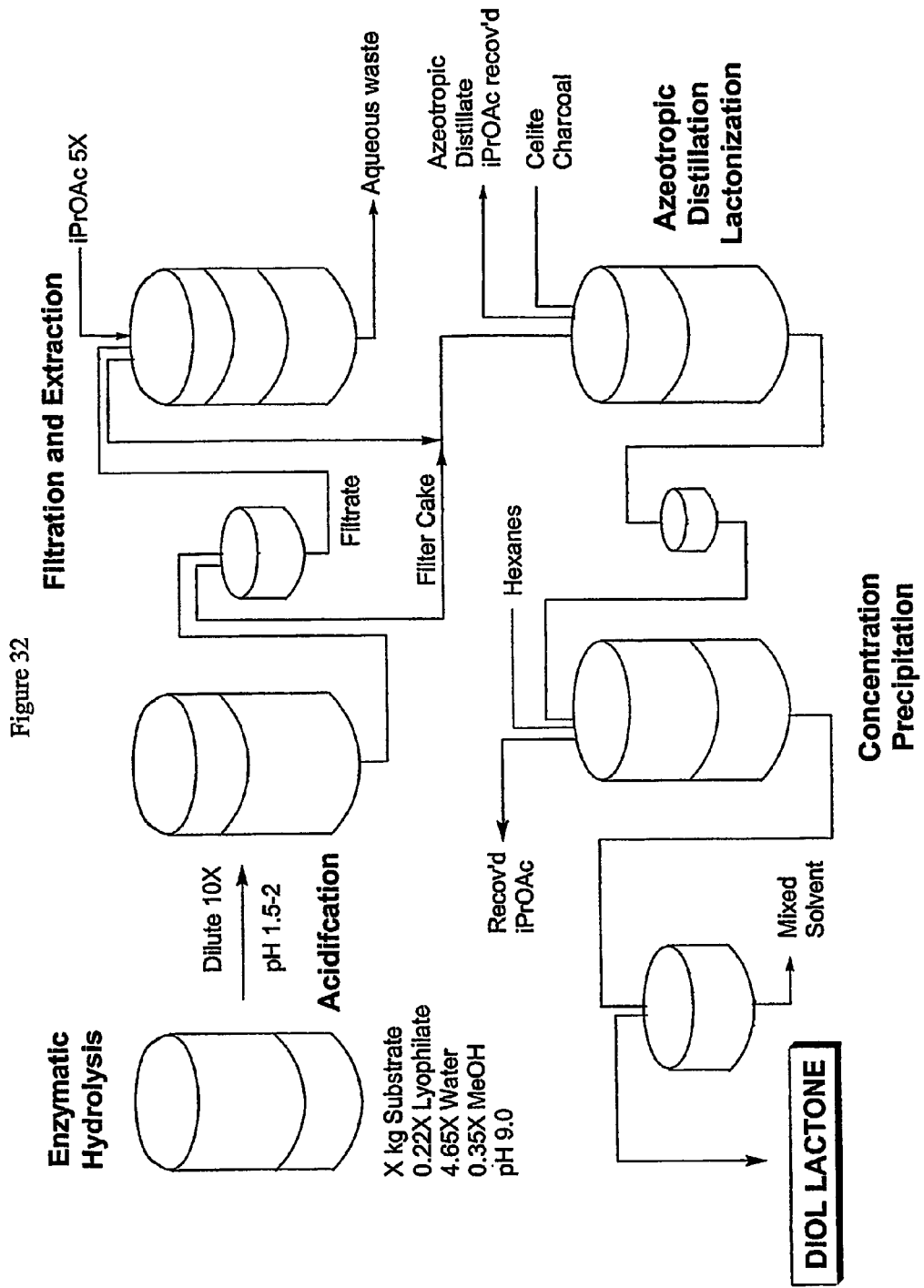
FIG. 32 illustrates a scaled-up protocol for the enzymatic hydrolysis of lovastatin to a diol lactone, as described in detail in Example 11, below.
Figure 33:
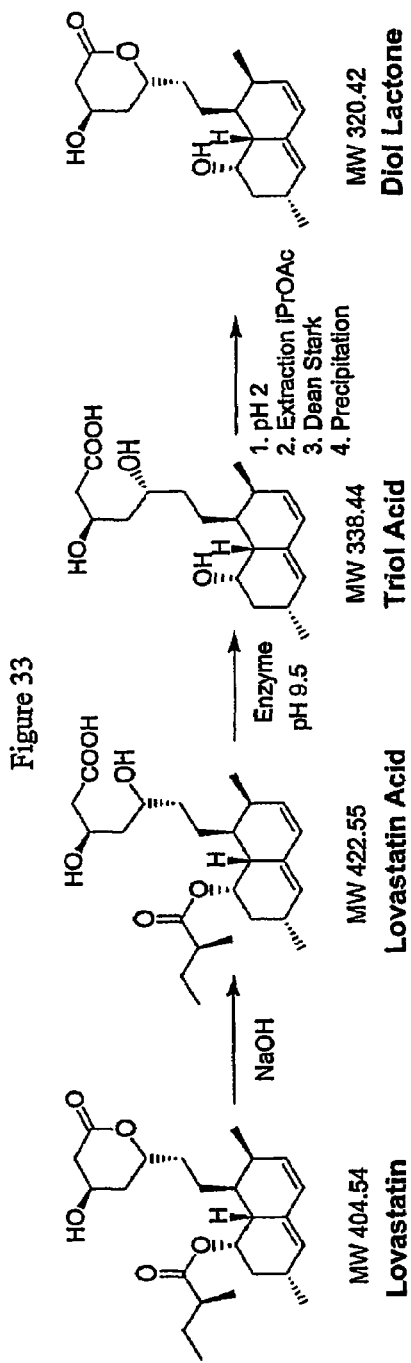
FIG. 33 illustrates an exemplary enzymatic hydrolysis of lovastatin to diol lactone used in a scaled-up protocol, with a summary of reaction parameters, as described in detail in Example 11, below.
Figure 36:
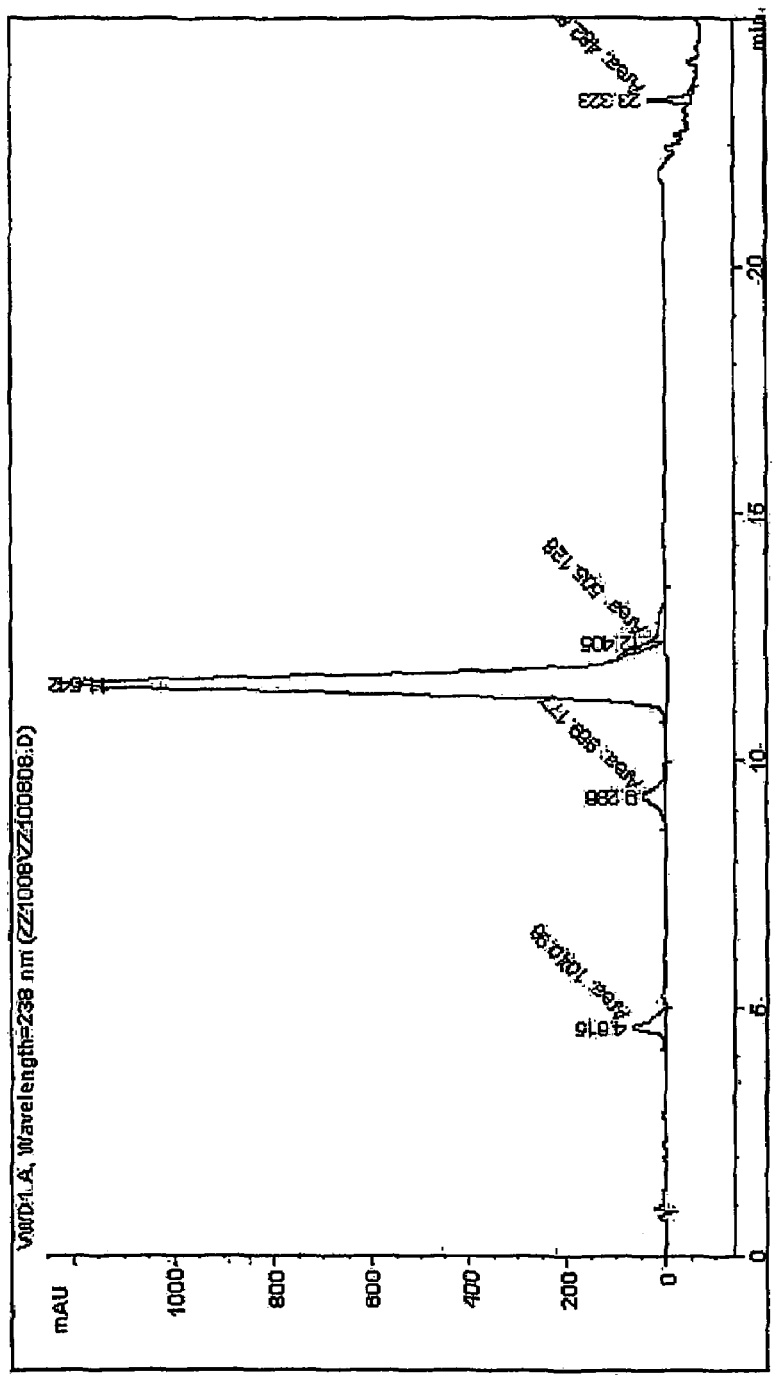
FIG. 36 illustrates a graphic summary of data from a 10 g scaled-up enzymatic hydrolysis reaction where 4-acetyl lactone was acylated to 4-acetyl simvastatin, as described in detail in Example 11, below.
Figure 37:
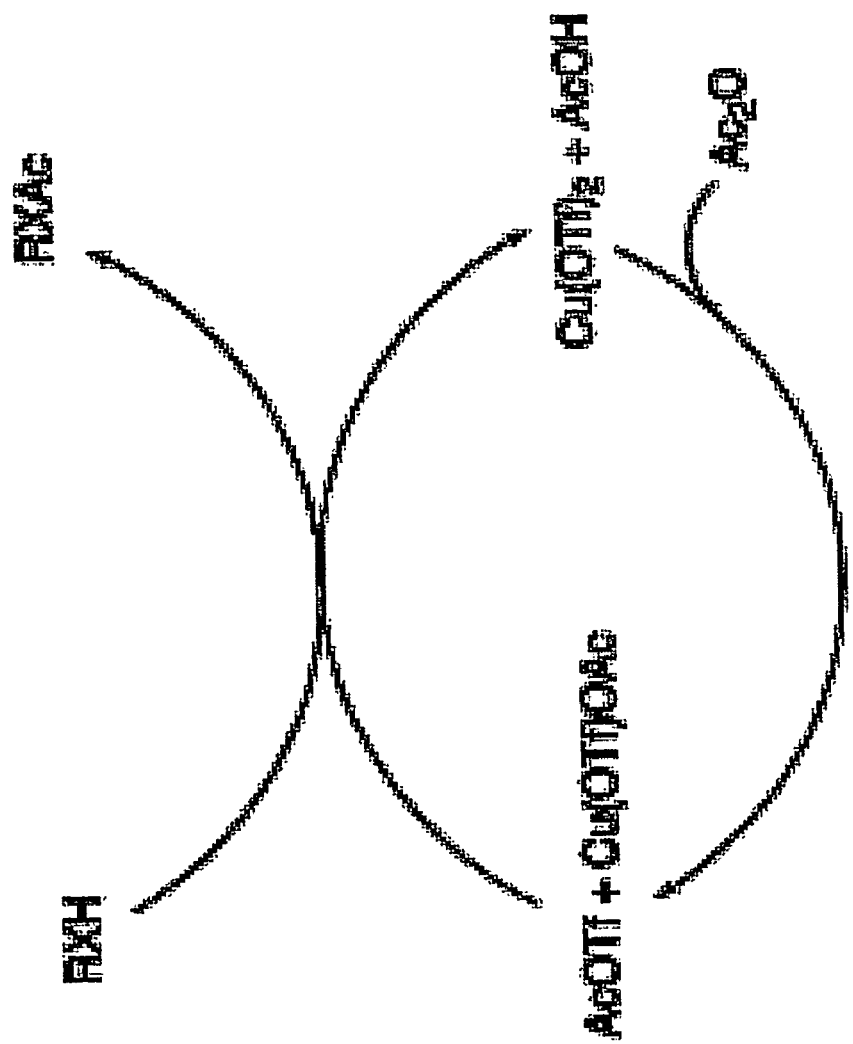
FIG. 37 illustrates an exemplary chemical acylation used in a process of the invention, a Lewis acid-catalyzed acylation using acyl triflate, as described in detail in Example 11, below.

A large-scale enzymatic hydrolysis of lovastatin to lovastatin acid to triol acid was carried out on a DasGip FEDBATCH PRO™ bioreactor at constant pH 9, substrate at 500 mM, 7% MeOH, 40° C., as illustrated in FIG. 31. A scaled-up exemplary protocol of an enzymatic hydrolysis of lovastatin to diol lactone, which can be an exemplary industrial scale process, is illustrated in the schematic of FIG. 32. This reaction, with a summary of reaction parameters (reaction scale, workup, theoretical yield, product in g, % yield), is illustrated in FIG. 33. Data from (a) a 50 gram (g) reaction is summarized in FIG. 34A (after lactonization and concentration) and

34B (crude product), and (b) a 100 g reaction FIG. 35A (triol acid) and 35B (after lactonization).

Methyl (Me) 4-acetyl simvastatin was hydrolyzed enzymatically to simvastatin using a reaction as illustrated in FIG. 6, step 5. Results and conclusions from this reaction are:

Facile elimination at pH>7 (13% at pH 8).
Enzymatic hydrolysis occurs readily, but limited by solubility.
Formate>acetate~chloroacetate>methoxyacetate.
100 mM (5% w/v) hydrolyzed overnight at pH 7.
200 mM 84% conversion in 20 h in 10% MeOH at 50° C.
200 mM 89% conversion in 7 h with 50% w/w lyophilate.
400 mM biphasic with toluene.
Reactions proceed to 80-90% then stop.
Insoluble simvastatin traps unreacted substrate.

Summarizing these reactions (at 300 mM (14% w/v) substrate, All reactions with overhead stirring and stirrer bar below, pH 7 with 10% NH4OH; 50° C.) and final conversions:

270 mM acetyl simvastatin, 13 mM homo simvastatin, with solvent as equal volumes toluene, gave a final conversion of 88.2%.
300 mM acetyl simvastatin, with solvent as 10% methanol (MeOH), gave a final conversion of 91.3%.
300 mM acetyl simvastatin, with solvent as 10% methanol (MeOH), and addition toluene at 6 hours, gave a final conversion of 96.1%.

Example 12

A Homodiacylation Route to Simvastatin

Figure 38:
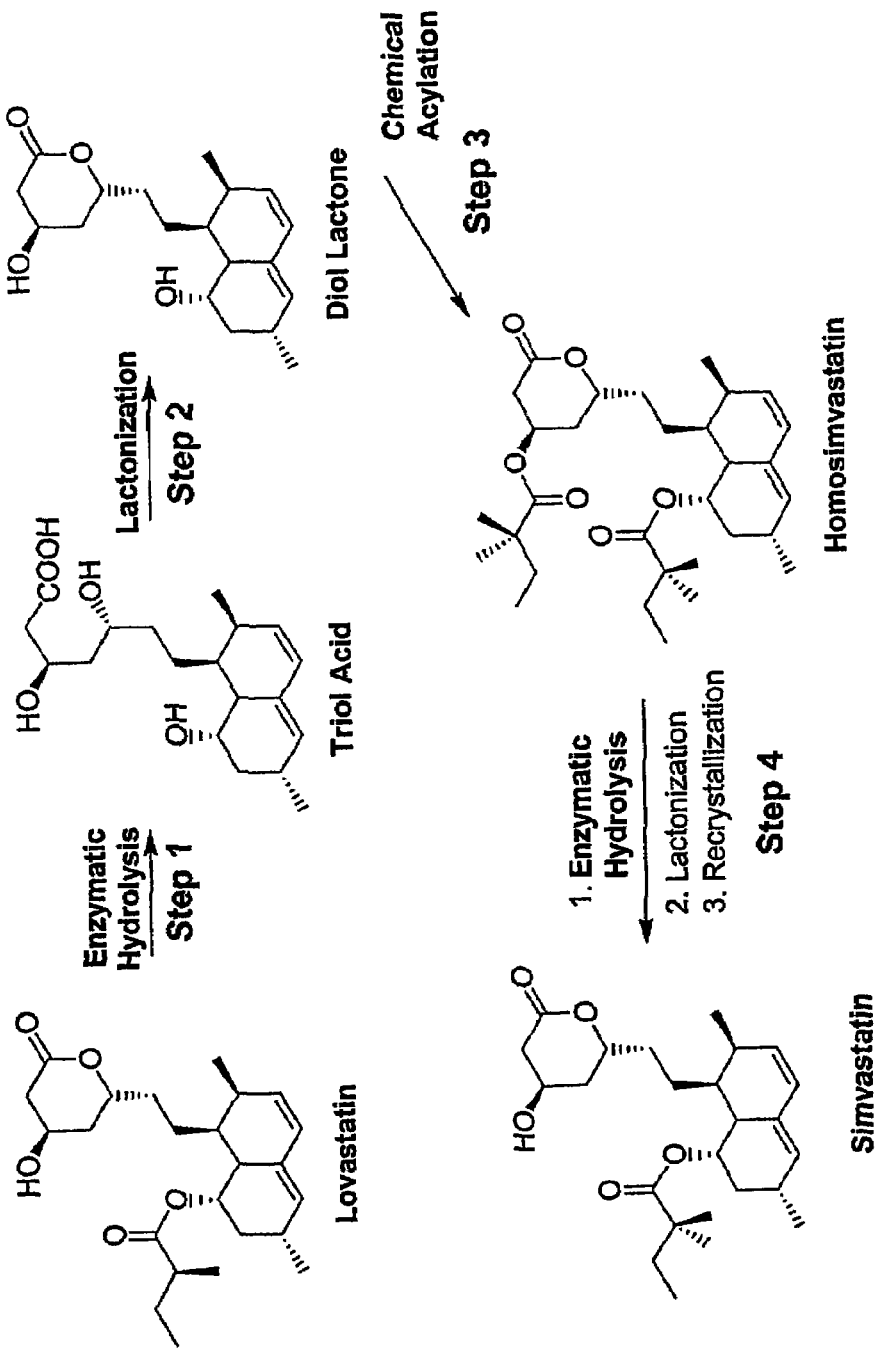
FIG. 38 and FIG. 39 illustrate exemplary methods and conditions for preparing simvastatin from lovastatin via a homodiacylation route, as described in detail in Example 12, below.
Figure 39:
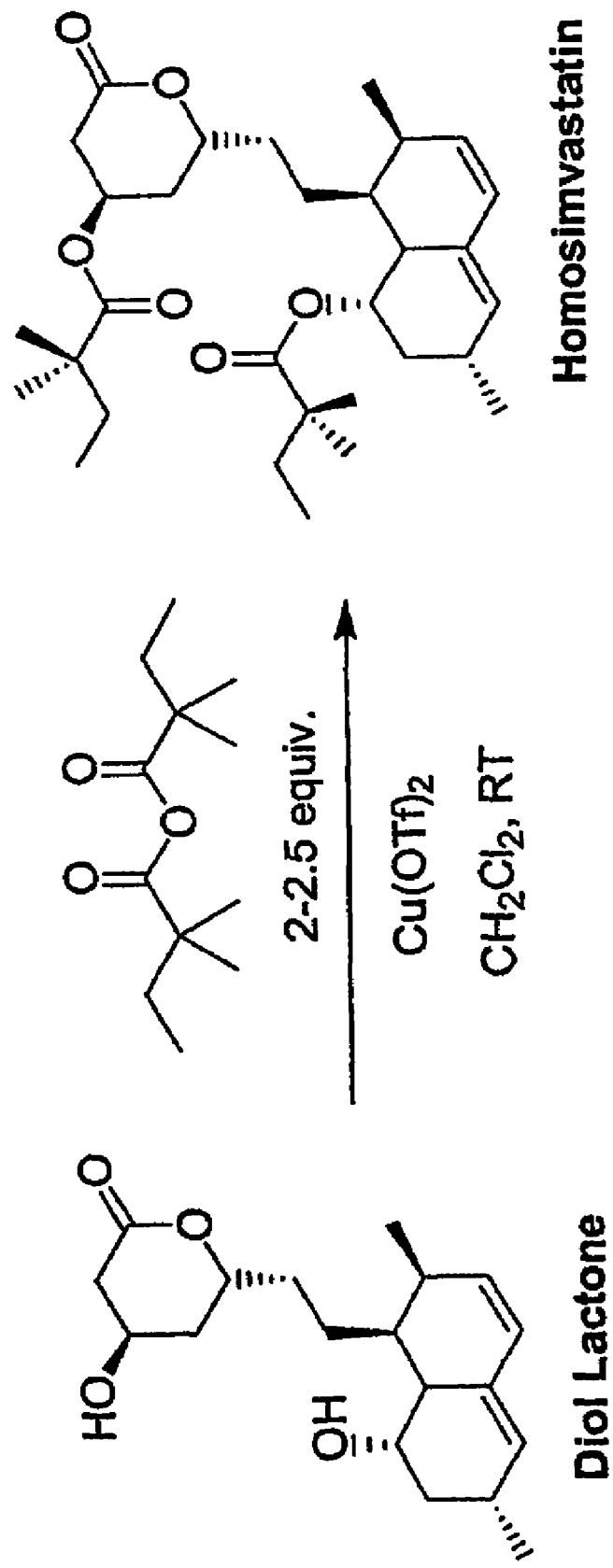

This example describes an exemplary protocol of the invention, a homodiacylation process for the preparation of simvastatin, as illustrated in FIG. 38 and FIG. 39. In one aspect, the homodiacylation process comprises a method having the following steps: (a) enzymatic hydrolysis of lovastatin, lovastatin acid or a salt of lovastatin acid to form a triol acid; (b) forming a diol lactone from the triol acid by lactonization; (c) acylating the 4-position (4'-OH) and 8-position (8'-OH) on the lactone ring of the diol lactone by chemical acylation to form a 4,8-diacetyl lactone; and (d) removing selectively the acyl group at the 4' position by enzymatic hydrolysis, thereby making simvastatin.

Advantages of using a homodiacylation process of the invention can be:

4-Step synthesis;
Enzymatic hydrolysis of lovastatin in place;
Single acylating agent—no regioselectivity.

Considerations for deciding when to use the homodiacylation process of the invention:

May need to use excess dimethylbutyryl chloride;
Harsh conditions—possibly can have unacceptable levels of elimination;
Can have difficulties in enzymatic hydrolysis;
Can use mild conditions for acylation
Removal of the 4'-dimethylbutyrate may be problematic.

In one aspect, the homodiacylation process of the invention is carried out as illustrated in FIG. 39. Hydrolysis was carried out using SEQ ID NO:4 at 1 mM scale to form simvastatin and simvastatin acid. A 100 mM bioreactor was used. Mainly triol acid was formed, with traces of simvastatin acid present. Solubility may need attention. Small scale reactions at various substrate concentrations was carried out; conversion results after 2 days:

|  | Triol acid % | Simvastatin acid % | Simvastatin % | Homo-Simvastatin % |
|---|---|---|---|---|
| 1 mM | 74.3 | 25.7 | 0.0 | 0.0 |
| 10 mM | 22.8 | 37.2 | 15.1 | 9.4 |
| 25 mM | 4.4 | 23.9 | 19.3 | 22.2 |
| 50 mM | 0.0 | 9.2 | 21.2 | 45.9 |

Figure 40A:
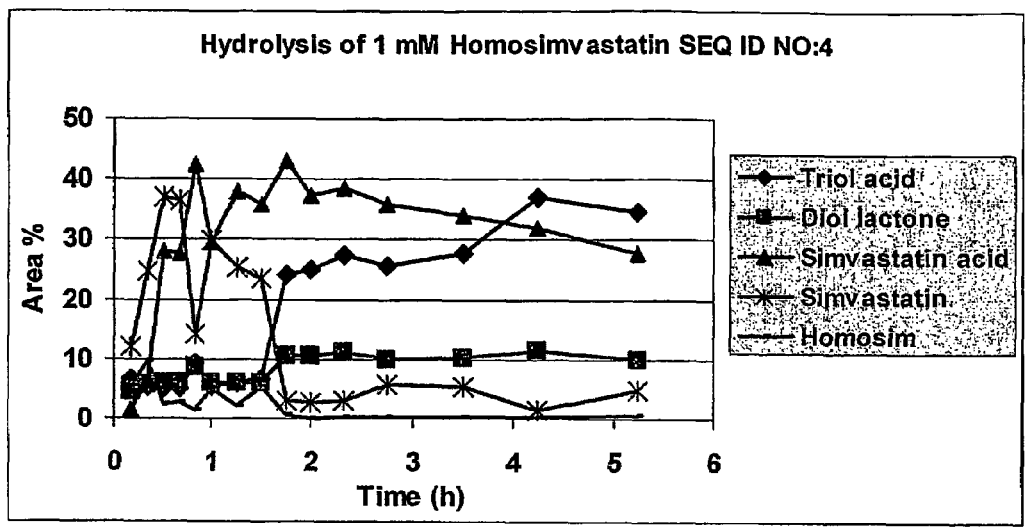
FIGS. 40A and 40B illustrate graphically hydrolysis of homosimvastatin with SEQ ID NO:4 using a method of the invention, and the resultant reaction product, at reaction conditions of 1 mM homosimvastatin and 10 mM homosimvastatin, as described in detail in Example 12, below.
Figure 40B:
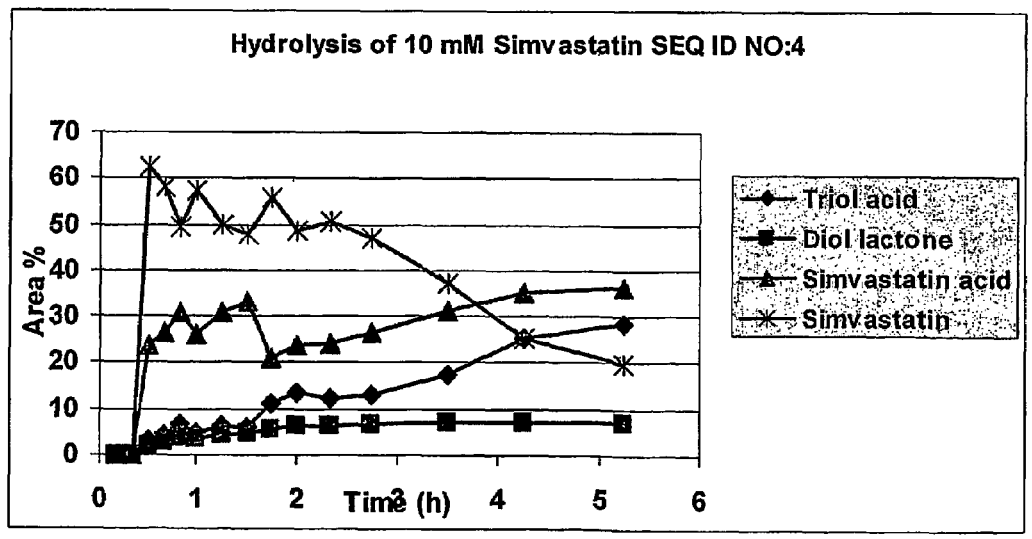

FIGS. 40A and 40B illustrate graphically the hydrolysis of homosimvastatin with SEQ ID NO:4, and the resultant reaction products, at reaction conditions of 1 mM homosimvastatin and 10 mM homosimvastatin, respectively.

Example 13

An Exemplary Process for Making Simvastatin

This example describes an exemplary process of the invention for making simvastatin, simvastatin intermediates, or equivalent compounds. This exemplary process of the invention comprises a method for (i) Hydrolysis of Lovastatin by lovastatin esterase and the subsequent "one-pot/one-step" lactonization/acetylation (as Steps 1 and 2), (ii) Acylation of 4-acetyllactone with dimethylbutyric anhydride with BF3 (Et2O) (A) or Cu(OTf)2 (B) catalyst (as Step 3). The acylation with dimethylbutyric anhydride/pyridine/DMAP (C) was included for comparison to demonstrate advantages of this method. (iii) Hydrolysis of acetylsimvastatin with lovastatin esterase (as Step 4).

4-Acetyllactone (50 g Scale)

Figure 19:
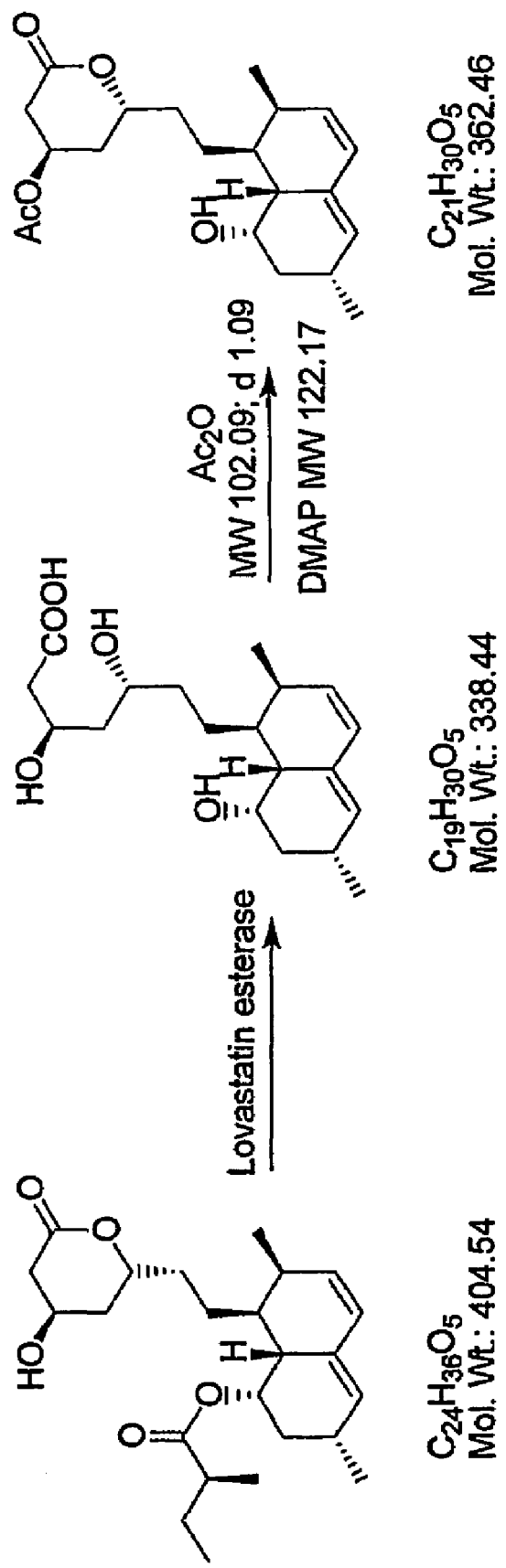
FIG. 19 illustrates an exemplary process for making 4-Acetyllactone, as discussed in detail in Example 13, below.

An exemplary process for making 4-Acetyllactone, as illustrated in FIG. 19, comprises:

1. Lovastatin (50.05 g, 124 mmol) was weighed into a 1-L 3-neck flask equipped with a magnetic stir bar and $N_2$ inlet. 2M NaOH (65 mL, 130 mmol) was added and the slurry stirred. MeOH (10 mL) and BHT (0.25 g) was added and the slurry was stirred in a water bath at 50° C. for 1 hour. By this time all the lovastatin had dissolved to give a viscous, slightly yellow solution. The solution was diluted with water (175 mL) and the temperature adjusted to 40° C.
2. Meanwhile, lovastatin esterase (5.0 g of a crude enzyme lyophilizate) was weighed into a polypropylene centrifuge bottle, suspended in water (100 mL) and stirred at room temperature for 30 min. The mixture was then centrifuged at 10,000 rpm at 4° C. for 15 minutes. The supernatant was added to the lovastatin acid reaction mixture. The centrifuge bottle was rinsed with a further portion of water (150 mL) which was added to the reaction mixture. (see Note 1, below)
3. The pH of the reaction was adjusted to pH 9.5 and was maintained at 40° and pH 9.5 on a DASGIP AG FED-BATCH—PRO® bioreactor by automatic addition of 10% $NH_4OH$.
4. Aliquots (25 µL) of the reaction mixture were removed periodically, diluted with MeOH and examined by HPLC (see Note 2, below). After 26.5 h, 0.5% of unreacted lovastatin acid remained. The reaction was terminated after 43 h.
5. The reaction mixture was diluted to 800 mL in a 1-L beaker and cooled to +12° C. With vigorous stirring the pH was reduced to pH 2.5 with 6M HCl. The precipitated solid was filtered under $N_2$, washed with water (300 mL) and the damp filter cake was dried in a vacuum oven at 40° C. (see Note 3, below).

6. The crude triol acid filter cake was suspended in CH$_2$Cl$_2$ (500 mL) in a 1-L 3-neck flask equipped with a thermometer, addition funnel, magnetic stir bar and N$_2$ inlet. The slurry was cooled in an ice bath and stirred under N$_2$.
7. Dimethylaminopyridine (2.24 g, 18.3 mmol; 0.15 equiv.) was added to the reaction mixture. Acetic anhydride (35 mL, 0.37 mol; 3 equiv.) was placed in the addition funnel and was added dropwise to the reaction mixture over a period 12 minutes, the temperature remaining at 8.5-9.2° C.
8. Aliquots (25 µL) of the reaction mixture were removed every 30 minutes, diluted with MeOH and examined by HPLC (see Note 4, below).
9. After 30 minutes the cooling bath was removed and the reaction stirred at room temperature (see Note 5, below). The reaction was terminated 6.25 h after the addition of Ac$_2$O (see Note 6, below). The reaction mixture was filtered through a pad of Celite and the pad washed with CH$_2$Cl$_2$ (2×100 mL). The combined filtrates were washed with water (200 mL), 1.2 M HCl (200 mL) and water (100 mL).
10. The organic layer was concentrated on a rotovap (250 mL removed) and diluted with EtOAc (300 mL). Water (400 mL and solid NaHCO$_3$ (53 g) was added to the organic solution and the mixture stirred for 30 min. Separated the organic layer. The aqueous layer was diluted with water (400 mL) and extracted with EtOAc (150 mL). The EtOAc extracts were combined and washed with a mixture of water (100 mL) and saturated (satd.) NaCL (50 mL) and then with satd. NaCl (100 mL). The organic layer was dried (Na$_2$SO$_4$), filtered and concentrated (420 mL removed from a 600 mL volume).
11. The pale yellow concentrated solution was stirred with an overhead stirrer and hexanes (200 mL) was added quickly, forming a dense white precipitate. A further portion of hexanes (300 mL) was added and the mixture cooled in an ice bath for 1.5 h.
12. The precipitate solid was filtered, washed with cold 20% EtOAc/hexanes (80 mL), air dried for 0.5 h then dried in a vacuum oven at 40° C. overnight.
13. The mother liquors were evaporated to dryness. The resulting yellow oil was redissolved in EtOAc (25 mL) and a second crop was precipitated by dropwise addition of hexanes (175 mL). The precipitated solid was collected by filtration and dried in a vacuum oven at 40° C. (see Note 7, below).

Notes

1. Total volume of the reaction was 500 mL, corresponding to a substrate concentration of 0.25M (10% w/v substrate) and a crude enzyme load of 10% w/w.
2. Samples were analyzed on a Waters 1100 Series HPLC equipped with a DAD, using a ZORBAX SB-Phenyl column (4.6×75 mm) (45% MeCN/0.5% AcOH isocratic; 1 ml/min; 30° C.; 238 nm). The order of elution was: Triol acid: 1.4 min, Diol lactone: 1.9 min, Lovastatin Acid: 3.8 min, Lovastatin: 7.3 min.
3. The filter cake (43.61 g) at this stage consists of crude triol acid and precipitated protein. HPLC analysis versus a working standard of triol acid indicated that the aqueous filtrate contained 0.69 g triol acid (1.6%) and 0.69 g diol lactone (1.8%).
4. Samples were analyzed on a Waters 1100 Series HPLC equipped with a DAD, using a ZORBAX SB-Phenyl column (4.6×75 mm) (45% MeCN/0.5% AcOH isocratic; 1 ml/min; 30° C.; 238 min). The order of elution was: Triol acid: 1.4 min, Diol lactone: 1.9 min, Diacetate Acid/Elimination: 3.6 min, 4-Acetyllactone: 4.1 min; Diacetate, 7.6 min.
5. The reaction mixture is initially lumpy, but vigorous stirring breaks up the major lumps. After 2 h the reaction mixture was sonicated to disperse some smaller lumps which persisted. Milling of the crude triol acid filter cake before suspending it in solvent is suggested. The final reaction mixture was a milky white suspension.
6. HPLC before quenching indicated the presence of 1.1% Diol lactone, 3.9% Diacetate acid/Elimination, and 1.2% Diacetate.
7. The total yield of product was calculated as shown in the following Table:

|  |  | g | mmol |  |
|---|---|---|---|---|
| Starting material | Lovastatin | 50.05 | 124 |  |
| Theoretical Yield | 4-Acetyllactone | 44.84 |  |  |
| Products | 1$^{st}$ crop | 35.43 | 97.8 |  |
|  | 2$^{nd}$ crop | 1.38 | 3.8 |  |
|  | Product in mother liquors | 0.65 | 1.8 |  |
| Total |  |  | 103.1 | 83.1% |
|  | Elemental Analysis | % C | % H |  |
|  | Expected | 69.59 | 8.34 |  |
|  | 1$^{st}$ Crop | 69.42 | 7.95 |  |
|  | 2$^{nd}$ Crop | 69.33 | 8.08 |  |

Synthesis of 4-Acetylsimvastatin

An exemplary process for making 4-acetyl simvastatin, as illustrated in FIG. 18C, comprises:

A. Boron Trifluoride Etherate Catalysis 1. 4-Acetyllactone (110 g, 0.3 mol) was dried overnight under vacuum (0.1 torr) in a 2-neck 2 L flask (see Note 1, below).
2. The dried starting material was dissolved in anhydrous CH$_2$Cl (875 mL) under N$_2$ at room temperature.
3. The catalyst was prepared as follows. In a glove bag under N$_2$, 2,2-dimethylbutyric anhydride (7.1 mL, 30.3 mmol) was added to anhydrous acetonitrile (125 mL), followed by the addition of freshly opened BF$_3$.OEt$_2$ (3.1 mL, 24.3 mmol; 8 mol %) (see Notes 2, 3, below).
4. 2,2-Dimethylbutyric anhydride (78 mL, 0.33 mol; 1.1 equiv.) was added to the solution of 4-acetyllactone and the mixture was heated to 40° C. for 10 minutes. The MeCN solution of BF$_3$.OEt$_2$ was then added via cannula. (see Note 4, below). The reaction was shielded from light, stirred at 40° C. and monitored by HPLC.
5. After 5.5 h the reaction was judged complete and the reaction was cooled to 5° C. in an ice bath. Satd. NaHCO$_3$ (250 mL) was added with vigorous stirring. The aqueous layer was separated and extracted with CH$_2$Cl$_2$ (200 mL).
6. The organic extracts were combined, dried (Na$_2$SO$_4$), filtered and concentrated under reduced pressure. MeOH (200 mL) was added to the concentrate (Note 5); removal of more MeOH results in precipitation of 4-acetylsimvastatin. The off-white solid was filtered, washed with cold MeOH (100 mL) and dried under vacuum (92.8 g).

7. The mother liquors were concentrated to about half volume and cooled at −10° C. overnight. A second crop if product (17.2 g) was collected by filtration and dried (see Note 6, below).
8. The HPLC profile is shown in the following Table.

| Peak Identity | Retention Time Min | Area % |
|---|---|---|
| 4-Acetyllactone | 1.73 | 0.06 |
| 4,8-Bisacetate | 2.37 | 0.80 |
| Simvastatin | 2.52 | 0.04 |
| Unknown | 3.52 | 0.03 |
| 4-Acetyl Lovastatin | 3.80 | 0.80 |
| 4-Acetyl Simvastatin | 4.59 | 97.78 |
| Anhydrosimvastatin | 5.47 | 0.31 |
| 4-Simvastain-8-Lovastatin | 8.30 | 0.03 |
| Bis-Simvastatin | 9.78 | 0.10 |
| Total Area | | 99.95 |

Notes
1. Drying at elevated temperature under vacuum may cause decomposition. 4-Acetyllactone turned yellowish when dried at 40° C. under vacuum.
2. Since the reaction is sensitive to the presence of moisture, excess anhydride was initially added to the acetonitrile to scavenge any residual water.
3. Freshly opened $BF_3.OEt_2$ should be used for the reaction; reagent that has been opened previously can result in slow, or even, no reaction.
4. The $CH_2Cl_2$/MeCN ratio was 7:1. Typically the ratio is between 6:1 and 9:1. The reaction is faster in MeCN but the product is formed with a less desirable impurity profile.
5. MeOH should be added before crude product solidifies, otherwise it is difficult to re-dissolve it in MeOH. Dissolving solid product in hot methanol caused decomposition and thus gave lower yield.
6. Total solid product was 110 g (78.7%). The final mother liquors were evaporated to dryness and the residue was assayed versus a working standard and shown to contain a further 9.02 g (6.8%) of product. A further ~2% product remained in the aqueous washes.

B. Cu $(OTf)_2$/Anhydride Method
1. 10.0 g of 4-Acetyllactone (10.0 g, 27.6 mmol) was dried under vacuum at room temperature for 1 hr, then dissolved in anhydrous $CH_2Cl_2$ (60 mL) and stirred under nitrogen.
2. Meanwhile, a solution of $Cu(OTf)_2$ (0.5 g 5 mol %) and 2,2-dimethylbutyric anhydride (7.15 mL, 30.5 mmol) in anhydrous MeCN (7.0 mL) was prepared and stirred at room temperature inside a sealed flask.
3. The lactone solution was cooled to 15° C. The solution of $Cu(OTf)_2$ and 2,2-dimethyl butyryl anhydride was added dropwise using syringe pump. The reaction was monitored by HPLC and judged complete within 3.0 hours.
4. The reaction was quenched with water (20 mL) and partitioned between CH2Cl2 (100 mL) and satd. NaCl (100 mL). The organic layer was then stirred for 10 minutes with a mixture of 1M malic acid (50 mL) and satd. NaCl (50 mL), then satd. NaCl (100 mL). The organic layer was dried (Na2SO4), filtered and evaporated to yield the crude product (12.8 g>100% yield by weight) (see Notes 1, 2, below).

Notes:
1. The product distribution by HPLC area % was: 4-acetylsimvastatin (92.5%), elimination product (2.7%), bis-simvastatin (1.7%), unidentified impurity (3.1%).
2. 4-Acetylsimvastatin was isolated in 61% after column chromatography.

C. Pyridine/DMAP Method
1. 4-Acetyllactone (2.6 g, 7.2 mmol) was dried under vacuum overnight at room temperature, then dissolved in anhydrous pyridine (6.0 mL) with stirring at room temperature under nitrogen. A solution of DMAP (176 mg, 0.2 equiv.) in 1.5 mL anhydrous pyridine was added and the mixture cooled in an ice bath.
2. 2,2-Dimethylbutyryl chloride (7.72 g, 8 equiv.) was added dropwise over 15 minutes using a syringe pump. The mixture was stirred at 0° C. for about one hour, then at room temperature for one hour.
3. The reaction mixture was heated at 40° C. under nitrogen and reaction was monitored by HPLC. After the 4-acetyllactone was consumed (2 days), the pyridine was removed by rotary evaporation. The residue was partitioned between EtOAc (20 mL) and saturated NaCl (20 mL). The organic layer was dried ($Na_2SO_4$), filtered and evaporated to give the crude product (96.5%) (see Notes 1, 2, below).

Notes
1. The product distribution by HPLC area % was: 4-acetylsimvastatin (79.5%), elimination product (12%), bis-simvastatin (2%), unidentified impurity (6.5%).
2. 4-Acetylsimvastatin was isolated in 43% after column chromatography. 4-Acyl simvastatin is believed to possess limited stability to $SiO_2$ chromatography.

Hydrolysis of 4-Acetylsimvastatin by Lovastatin Esterase
An exemplary process for making 4-acetylsimvastatin, as illustrated in FIG. 18D, comprises:
1. 4-Acetylsimvastatin (39.69 g, 86.2 mmol) was weighed into a 3-neck 500 mL round bottom flask equipped with a stir bar and a pH electrode (see Note 1, below). Added water (295 mL), MeOH (20 mL) and BHT (0.24 g). Stirred in a water bath at 50° C. and adjusted to pH 7-8 with 0.5 M NaOH.
2. Lovastatin esterase (7 g) was weighed into a centrifuge bottle and suspended in water (150 mL). The mixture was stirred at 60° C. for 30 min, then cooled on ice. The mixture was then centrifuged at 10,000 rpm at 4° C. for 125 min. A portion of the supernatant (92 mL) was added to the reaction mixture.
3. The reaction was stirred at 50° C. and maintained at pH 7.5 using a DASGIP FEDBATCH—PRO® system, by automatic addition of 10% $NH_4OH$.
4. Aliquots (25 μL) of the reaction mixture were removed periodically, diluted with MeOH and examined by HPLC (see Note 2, below). After 42 h, the conversion was 96.8% (ratio of product to starting material peak areas). The reaction was terminated after 64 h.
5. The reaction mixture was filtered through a 13 cm Buchner funnel equipped with Whatman #1 filter paper, and the filter cake washed with water (100 mL). The damp filter cake was dried in a vacuum oven at 40° C. overnight (see Note 3, below).
6. The dried Simvastatin filter cake was suspended in $CH_2Cl_2$ (200 mL). The mixture was stirred at room temperature to get a viscous brown solution containing gel like material. Celite (1 g) was added to the mixture and stirring continued. The mixture was then filtered through a Celite pad (10 g) on a coarse sintered glass funnel (Note 4). The Celite pad was washed with toluene (100 mL).
7. The filtrate was concentrated on a rotovap to remove $CH_2Cl_2$ (bath temp. 20° C.). The residue was diluted with toluene (150 mL) and stirred at room temperature.

Hexanes (50 mL) was added slowly dropwise; precipitation commenced before completion of addition. The slurry was stirred overnight at room temperature. The slurry was then cooled in an ice bath and a further portion of hexanes was added dropwise (50 mL). The cold slurry was then filtered and the filter cake washed with cold 25% toluene/hexanes (50 mL). The filter cake was briefly air-dried, then dried at 30° C. under vacuum.

8. A second reaction was carried out on the same scale under similar conditions (40.68 g, 88.3 mmol). The results of these two experiments are tabulated in Note 5.

Notes

1. Since both the starting materials and products are insoluble efficient stirring is necessary. Material tends to adhere to the walls of the flask, leading to potential errors in analyzing the extent of reaction. Milling the starting material to reduce particle size and the use of wetting agents is suggested.
2. Samples were analyzed on a Waters 1100 Series HPLC, using a Zorbax SB-Phenyl column (4.6×75 mm) (60-90% MeCN/0.5% AcOH gradient; 1 ml/min; RT; 238 nm). The gradient and elution order were as follows:

| Time min | MeCN | 0.5% AcOH | Component | Rt |
|---|---|---|---|---|
| 0 | 60 | 40 | Triol Acid | 0.99 |
| 10 | 60 | 40 | Diol lactone | 1.19 |
| 15 | 90 | 10 | 4-Acetyllactone | 1.75 |
| 25 | 90 | 10 | Lovastatin | 2.22 |
| 27 | 60 | 40 | Simvastatin | 2.58 |
| | | | 4-Acetyllovastatin | 3.76 |
| | | | 4-Acetylsimvastatin | 4.50 |
| | | | Eliminated Simvastatin | 4.87 |
| | | | 4-Simvastatin-8-Lovastatin | 7.67 |
| | | | Bis Simvastatin | 9.45 |

3. The filter cake (35.28 g) at this stage consists of crude simvastatin and some enzyme related material. HPLC analysis versus a working standard of Simvastatin indicated that the aqueous filtrate contained 0.30 g Simvastatin (1.0%).

4. The insoluble gel-like material can form a sludge on top of the Celite pad which fouls the filtration.

5. Results of the two experiments described above:

| | | | | % Yield | |
|---|---|---|---|---|---|
| | | g | mmol | | |
| Starting material | 4-Acetylsimvastatin Run #1 | 39.69 | 86.2 | | |
| Theoretical Yield | Simvastatin | 51.73 | (from 50 g Lovastatin | | |
| Products | 1st crop | 26.51 | 51.3 | 51.3 | |
| | Product in mother liquors | 4.49 | 10.7 | 8.7 | |
| | Celite pad | 0.55 | 1.3 | | |
| Total | | | 63.3 | 61% | |
| | Elemental Analysis | % C | % H | | |
| | Expected | 71.74 | 9.15 | | |
| | 1st Crop | 71.60 | 9.50 | | |
| | HPLC Assay vs working standard | 97.5% | | | |
| Starting material | 4-Acetylsimvastatin Run #2 | 40.68 | 88.3 | | |
| Theoretical Yield | Simvastatin | 51.73 | (from 50 g Lovastatin | | |
| Products | 1st crop | 30.14 | 72.0 | 58.3 | |
| | Product in mother liquors | 2.34 | 5.6 | 4.5 | |
| | Celite pad | 0.40 | 0.9 | | |
| Total | | | 78.5 | 63% | |
| | Expected | 71.74 | 9.15 | | |
| | 1st Crop | 71.80 | 9.49 | | |
| | HPLC Assay vs working standard | 97.4% | | | |

A number of embodiments of the invention have been described. Nevertheless, it will be understood that various modifications may be made without departing from the spirit and scope of the invention. Accordingly, other embodiments are within the scope of the following claims.

What is claimed is:

1. A method for the preparation of simvastatin comprising a homodiacylation process comprising:
   (a) enzymatic hydrolysis of lovastatin, lovastatin acid or a salt of lovastatin acid with an esterase enzyme to form a triol acid,
   wherein the esterase has a sequence having at least about 90% sequence identity to SEQ ID NO:2, SEQ ID NO:4 or SEQ ID NO:6;
   (b) forming a diol lactone from the triol acid by lactonization;
   (c) acylating the 4-position (4'-OH) and 8-position (8'-OH) on the lactone ring of the diol lactone by chemical acylation to form a 4,8-diacetyl lactone; and
   (d) removing selectively the acyl group at the 4' position by enzymatic hydrolysis, thereby making simvastatin.

2. A method for preparing 4-acetyl lactone comprising enzymatic hydrolysis of lovastatin with an esterase enzyme to make a triol acid or a salt of a triol acid, followed by lactonization of the triol acid to make a diol lactone, followed by regioselective enzymatic acylation of the diol lactone on the 4-position (4'-OH) of the lactone ring to make 4-acetyl lactone,
   wherein the esterase has a sequence having at least about 90% sequence identity to SEQ ID NO:2, SEQ ID NO:4 or SEQ ID NO:6.

3. A method for preparing 4-acetyl-simvastatin comprising enzymatic hydrolysis of lovastatin with an esterase enzyme to make a triol acid or a salt of a triol acid, followed by lactonization of the triol acid to make a diol lactone, followed by regioselective enzymatic acylation of the diol lactone on the 4-position (4'-OH) of the lactone ring to make 4-acetyl lactone, followed by regioselective enzymatic acylation of the 4-acetyl lactone on the 8-position (8'-OH) of the lactone to make 4-acetyl-simvastatin,
   wherein the esterase has a sequence having at least about 90% sequence identity to SEQ ID NO:2, SEQ ID NO:4 or SEQ ID NO:6.

4. A method for the preparation of a triol acid or a salt of a triol acid from lovastatin with an esterase enzyme comprising:
   (a) providing a lovastatin, lovastatin or a salt of lovastatin, and an esterase enzyme; and
   (b) contacting the lovastatin, lovastatin or a salt of lovastatin with the esterase under conditions wherein the esterase catalyzes the hydrolysis of the lovastatin to a triol acid or a salt of a triol acid,
   wherein the esterase has a sequence having at least about 90% sequence identity to SEQ ID NO:2, SEQ ID NO:4 or SEQ ID NO:6.

5. A kit comprising (a) reagents and at least one esterase enzyme for practicing the methods of claim 1, wherein the esterase has a sequence having at least about 90% sequence identity to SEQ ID NO:2, SEQ ID NO:4 or SEQ ID NO:6; and
   (b) instructions for practicing the methods of claim 1.

6. The method of claim 1, wherein at least one step is performed in a separate reaction vessel.

7. The method of claim 6, wherein at least two steps are performed in separate reaction vessels.

8. The method of claim 1, wherein at least one step is performed with a cell extract, or at least one step is performed in a whole cell.

9. The method of claim 1, further comprising crystallization of the simvastatin.

10. The method of claim 9, further comprising re-crystallization of the simvastatin.

11. The method of claim 1, further comprising re-lactonization to provide simvastatin with a desired purity.

12. The method of claim 1, wherein at least one hydrolysis reaction is carried out by an esterase:
    (a) encoded by a nucleic acid having at least sequence identity to SEQ ID NO:1, or enzymatically active fragments thereof;
    (b) encoded by a nucleic acid having at least sequence identity to SEQ ID NO:3, or enzymatically active fragments thereof; or
    (c) encoded by a nucleic acid having at least sequence identity to SEQ ID NO:5, or enzymatically active fragments thereof.

13. The method of claim 1, wherein at least one hydrolysis reaction is carried out by an esterase having a sequence at least about sequence identity to SEQ ID NO:2, SEQ ID NO:4 or SEQ ID NO:6, or enzymatically active fragments thereof.

14. The method of claim 1, wherein the method further comprises enzymatic hydrolysis of lovastatin to make a triol acid or a salt of a triol acid.

15. The method of claim 14, wherein the method further comprises lactonization of the triol acid and enzymatic acylation of the 4-postion (4'-OH) of the lactone ring to make a 4-acyl lactone.

16. The method of claim 15, wherein the method further comprises enzymatic acylation of the 4-acyl lactone to make a 4-acetyl-simvastatin.

17. The method of claim 16, wherein the method further comprises regioselective enzymatic hydrolysis of the 4-acetyl-simvastatin to make simvastatin.

18. The method of claim 4, wherein the esterase has a sequence at least about sequence identity to SEQ ID NO:2, SEQ ID NO:4 or SEQ ID NO:6.

19. The method of claim 1, wherein enzymatic hydrolysis reaction is carried out by an esterase having a sequence as set forth in SEQ ID NO:2, SEQ ID NO:4 or SEQ ID NO:6.

20. The method of claim 2, wherein enzymatic hydrolysis reaction is carried out by an esterase having a sequence as set forth in SEQ ID NO:2, SEQ ID NO:4 or SEQ ID NO:6.

21. The method of claim 3, wherein enzymatic hydrolysis reaction is carried out by an esterase having a sequence as set forth in SEQ ID NO:2, SEQ ID NO:4 or SEQ ID NO:6.

22. The method of claim 4, wherein enzymatic hydrolysis reaction is carried out by an esterase having a sequence as set forth in SEQ ID NO:2, SEQ ID NO:4 or SEQ ID NO:6.

* * * * *